US012622896B2

(12) United States Patent
Grierson et al.

(10) Patent No.: US 12,622,896 B2
(45) Date of Patent: May 12, 2026

(54) ANTIVIRAL COMPOUNDS, COMPOSITIONS AND METHODS OF USE

(71) Applicants: THE UNIVERSITY OF BRITISH COLUMBIA, Vancouver (CA); THE GOVERNING COUNCIL OF THE UNIVERSITY OF TORONTO, Toronto (CA); SOCIETE DE COMMERCIALISATION DES PRODUITS DE LA RECHERCHE APPLIQUEE SOCPRA SCIENCES SANTE ET HUMAINES S.E.C., Sherbrooke (CA)

(72) Inventors: David Scott Grierson, Vancouver (CA); Maryam Zamiri, Vancouver (CA); Peter K. Cheung, Burnaby (CA); Benoit Chabot, Magog (CA); Alan Walter Cochrane, Toronto (CA)

(73) Assignees: The University of British Columbia, Vancouver (CA); The Governing Council of the University of Toronto, Toronto (CA); Societe de Commercialisation des Produits de la Recherche Appliquee Socpra Sciences Sante et Humaines S.E.C., Sherbrooke (CA)

( * ) Notice: Subject to any disclaimer, the term of this patent is extended or adjusted under 35 U.S.C. 154(b) by 907 days.

(21) Appl. No.: 17/785,394

(22) PCT Filed: Dec. 15, 2020

(86) PCT No.: PCT/CA2020/051724
§ 371 (c)(1),
(2) Date: Jun. 14, 2022

(87) PCT Pub. No.: WO2021/119808
PCT Pub. Date: Jun. 24, 2021

(65) Prior Publication Data

US 2023/0105935 A1 Apr. 6, 2023

Related U.S. Application Data

(60) Provisional application No. 62/948,672, filed on Dec. 16, 2019.

(51) Int. Cl.
*A61K 31/428* (2006.01)
*A61P 31/18* (2006.01)

(52) U.S. Cl.
CPC ............ *A61K 31/428* (2013.01); *A61P 31/18* (2018.01)

(58) Field of Classification Search
CPC ........ A61K 31/428; A61P 31/12; A61P 31/18; C07D 417/12
See application file for complete search history.

(56) References Cited

FOREIGN PATENT DOCUMENTS

| | | | |
|---|---|---|---|
| EP | 3 290 417 | A1 | 3/2018 |
| WO | 01/97786 | A2 | 12/2001 |

(Continued)

OTHER PUBLICATIONS

Anderson (Chem and Biol 10:787-797, 2003) (Year: 2003).*

(Continued)

*Primary Examiner* — Savitha M Rao
(74) *Attorney, Agent, or Firm* — Christensen O'Connor Johnson Kindness PLLC

(57) ABSTRACT

Provided herein are antiviral compounds having the structure of Formula (I) and compositions thereof for use in the treatment of viral infection. In particular, the compounds of Formula (I) are capable of interfering with the export of viral mRNA processing as reflected in the altered accumulation of viral RNA isoforms as well as transport from the nucleus to (Continued)

the cytoplasm. Such compounds show a reduction of HIV, adenovirus and coronavirus infection of cells. The invention provides compounds that may be suitable for the treatment of HIV/AIDS.

12 Claims, 34 Drawing Sheets

(56) References Cited

FOREIGN PATENT DOCUMENTS

| | | | |
|---|---|---|---|
| WO | 2005/037845 | A1 | 4/2005 |
| WO | 2007/029035 | A2 | 3/2007 |
| WO | 2009/019504 | A1 | 2/2009 |

OTHER PUBLICATIONS

Thiel (Nature Biotechnol 2:513-519, 2004) (Year: 2004).*
International Preliminary Report on Patentability mailed May 17, 2022, issued in corresponding International Application No. PCT/CA2020/051724, filed Dec. 15, 2020, 9 pages.
McDonald, K., et al., "In-Gel Protein Quantitation Using the Criterion Stain Free Gel Imaging System," Imaging, Bulletin 5782, 2008 Bio-Rad Laboratories, Inc., 6 pages.
Wong, R., et al., "Differential effect of CLK SR Kinases on HIV-1 gene expression: potential novel targets for therapy," Retrovirology 2011, 8:47, 12 pages.
Wong, R.W., et al., "Characterization of novel inhibitors of HIV-1 replication that function via alteration of viral RNA processing and rev function," Nucleic Acids Research, 2013, vol. 41, No. 20, pp. 9471-9483.
Zamiri, M., et al., "A Trimethylsilylamine-Acyl Fluoride Amide Bond Forming Protocol for Weakly Nucleophilic Amines that is Amenable to the Parallel Synthesis of Di(hetero)arylamides," Synthesis 2017, 49, pp. 571-578.
Chemical Abstracts - Registry Nos. STN (file REGISTRY): RN's of exemplified compounds: 328038-47-7 (ED Mar. 19, 2001); 306290-25-5 (ED Dec. 4, 2000); 905681-62-1 (ED Sep. 1, 2006); 722471-77-4 (ED Aug. 5, 2004); 1024245-70-2 (ED Jun. 1, 2008); 325987-93-7 (ED Mar. 7, 2001); 878084-63-0 (ED Mar. 27, 2006) RN's - Other compounds: 1386336-81-7 (ED Aug. 3, 2012); 1318490-75-3 (ED Aug. 16, 2011); 1241332-76-2 (ED Sep. 15, 2010); 1023509-40-1 (ED May 29, 2008); 905681-62-1 (ED Sep. 1, 2006); 905673-45-2 (ED Sep. 1, 2006); 892856-59-6 (ED Jul. 16, 2006); 862807-34-9 (ED Sep. 9, 2005); 862807-12-3 (ED Sep. 9, 2005); 560996-45-4 (ED Aug. 5, 2003); 325741-10-4 (ED Mar. 5, 2001); 1421839-61-3 (ED Feb. 26, 2013); 219619-26-8 (ED Feb. 11, 1999); 875286-88-7 (ED Feb. 27, 2006); 905690-42-8 (ED Sep. 1, 2006); 797776-58-0 (ED Dec. 15, 2004); 438474-53-4 (ED Jul. 12, 2002); 545364-79-2 (ED Jul. 10, 2003); 862807-43-0 (ED Sep. 9, 2005); 1071839-15-0 (ED Nov. 10, 2008); 15864-24-1 (ED Nov. 16, 1984); 301236-19-1 (ED Nov. 3, 2000); 308294-61-3 (ED Dec. 13, 2000); 361197-59-3 (ED Oct. 9, 2001); 476297-75-3 (ED Dec. 15, 2002); 956182-41-5 (ED Nov. 28, 2007); 862829-39-8 (ED Sep. 9, 2005): 445015-13-4 (ED Aug. 27, 2002): 339219-85-1 (ED Jun. 1, 2001): 328090-12-6 (ED Mar. 20, 2001); 328090-11-5 (ED Mar. 20, 2001).
Ohba, Mai, et al. "Discovery and synthesis of heterocyclic carboxamide derivatives as potent anti-norovirus agents." Chemical and Pharmaceutical Bulletin 64.5 (2016): 465-475.
Ismail, M. A. H., et al. "Molecular design, synthesis and cell based HCV replicon assay of novel benzoxazole derivatives." Drug research 63 (2013): 109-120.
Saraswat, Pankaj, et al. "Design, synthesis and biological evaluation of benzothiazole-thiophene hybrids: A new class of potent antimicrobial agents." Anti-Infective Agents 16.1 (2018): 57-63.
Wang, Xuesong, et al. "Synthesis and antifungal activity evaluation of new heterocycle containing amide derivatives." Natural Product Research 30.6 (2016): 682-688.
International Search Report and Written Opinion mailed Feb. 16, 2021, issued in corresponding International Application No. PCT/CA2020/051724, filed Dec. 15, 2020, 15 pages.
International Preliminary Report on Patentability mailed May 17, 2022, issued in corresponding International Application No. PCT/CA2020/051724, filed Dec. 15, 2020, 9 pages.

* cited by examiner

Figrue 3A
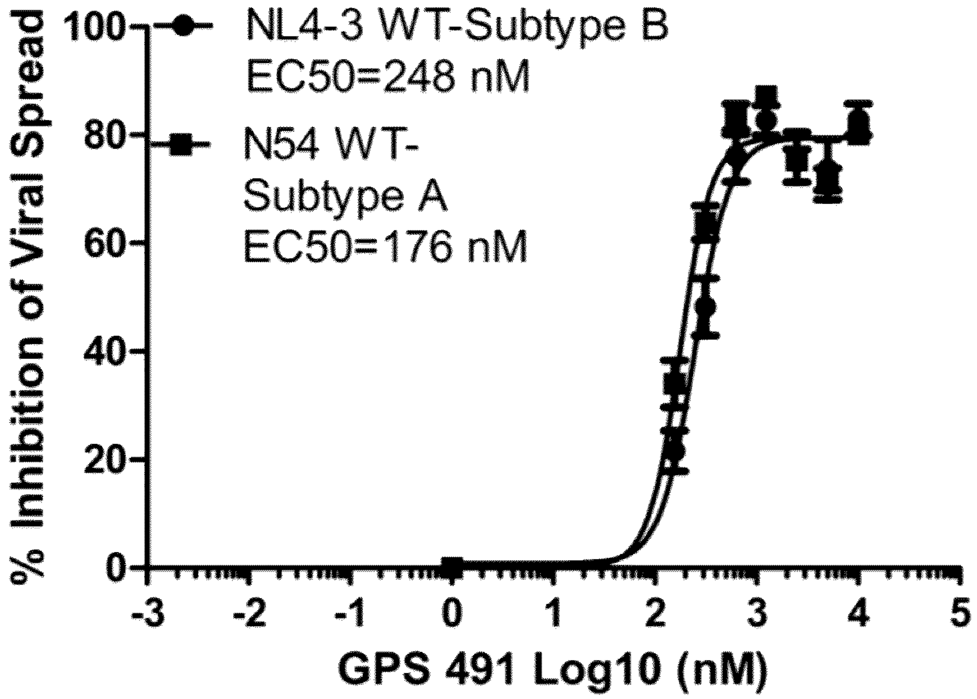
FIG. 3B
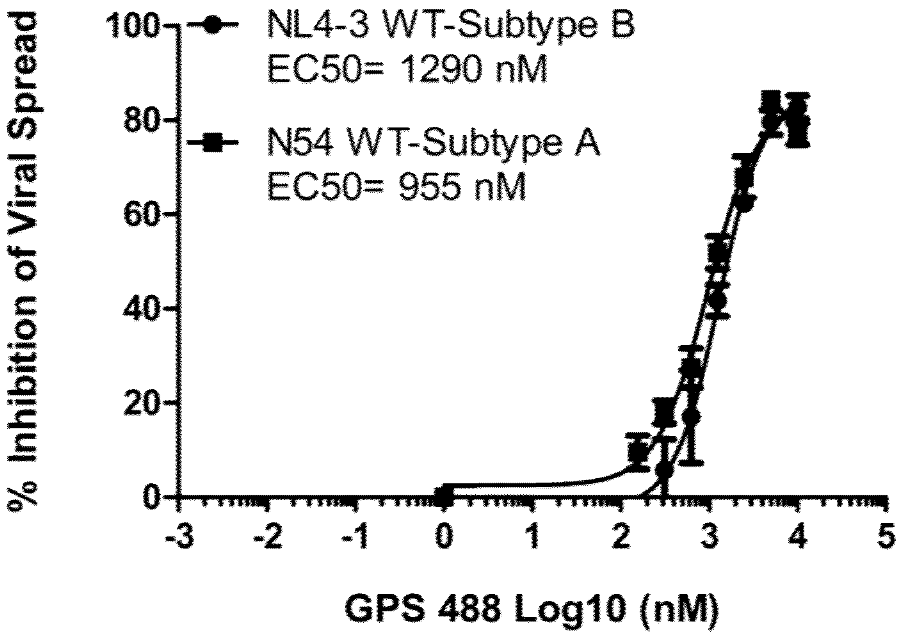

A

B $n \geq 3$

ANTIVIRAL COMPOUNDS, COMPOSITIONS AND METHODS OF USE

CROSS REFERENCE TO RELATED APPLICATION

This application is a National Stage of International Application No. PCT/CA2020/051724 filed Dec. 15, 2020, which claims the benefit of U.S. Provisional Patent Application Ser. No. 62/948,672 filed Dec. 16, 2019, the disclosure of each of which is expressly incorporated herein by reference in its entirety.

TECHNICAL FIELD

This invention relates to therapeutic compounds, their uses and methods for the treatment of viral infection. The viral infection may be a retroviral infection or ones whose replication is dependent upon host cell RNA processing factors (for example, adenovirus, herpes, influenza, SARS, coronavirus). The compounds are shown to interfere with the RNA processing of both HIV-1 and adenovirus, as evidenced by changes in accumulation of viral RNA spliced forms and the modification of cellular proteins involved in regulating RNA processing. The invention provides compounds that may be suitable for the treatment of HIV AIDS as well as other viral infections (adenovirus, influenza, hepatitis B, herpes, coronavirus) dependent upon the activity of the RNA processing factors modified.

BACKGROUND

Acquired Immunodeficiency Syndrome (AIDS) is a disease of the immune system resulting from infection with Human Immunodeficiency Virus (HIV). The HIV virus is a retrovirus, which is a type of RNA virus that inserts a copy of its genome into the DNA of an infected host cell to change the genome of the host cell. Once inside the host cell's cytoplasm, the virus reverse-transcribes DNA from its RNA genome using a reverse transcriptase enzyme. The viral DNA is then incorporated into the host cell genome by an integrase enzyme to form a provirus. Both the reverse transcriptase enzyme and the integrase enzyme form part of the HIV virion. When the host cell transcribes and translates its own genomic DNA, the viral genes of the provirus are made into viral proteins suitable for assembly into new viruses.

HIV are found as two species of Lentivirus: HIV-1 and HIV-2. Each type may be transmitted through direct contact with HIV-infected body fluids. The HIV virus is effective at disrupting the human immune system. Particular targets for HIV are helper T cells (especially, CD4+ T cells), macrophages, and dendritic cells. Following host infection levels of CD4+ T cells usually drop below a critical level whereby cell-mediated immunity is lost and the body becomes progressively more susceptible to opportunistic infections and cancers. To be diagnosed with AIDS, a person with HIV must have an AIDS-defining condition or have a CD4 count less than 200 cells/$mm^3$.

Highly active antiretroviral therapy (HAART), which is also sometimes referred to as combined Antiretroviral Therapy (cART) or Antiretroviral Therapy (ART), targets multiple viral proteins or processes, including: viral entry; reverse transcription; integration; transcription; and virus assembly and production. HAART is capable of reducing the viral load to below 50 copies and replenished the number of CD4+ T cells. However, despite increased survival rates, AIDS is now a chronic condition resulting in complications from long-term HAART (i.e. disrupted lipid metabolism). Despite the obvious benefits of HAART the treatment has low specificity, is highly toxic and expensive. Furthermore, HAART is thought to promote selection of viral mutants that are less susceptible to HAART. Lastly, HARRT does not address the problem of HIV reservoir, where dormant virus may reside in resting T cells.

Recently, it was determined that the stilbene-based compound, 2-(2-(5-nitro-2-thienyl)vinyl)quinolone (known as 5350150), blocked HIV replication, through a mode of action that involved interference with the export of HIV mRNAs from the nucleus to the cytoplasm (Wong, Balachandran et al. 2013). Although 5350150 manifested its activity at concentrations below its toxicity threshold, the known photolabile/toxic properties of related thiophene substituted stilbene compounds strongly suggested that any effort to exploit the anti-HIV properties of this system would have to begin with replacement of the central stilbene double bond.

SUMMARY

This invention is based in part on the discovery that compounds described herein modulate viral infection. Fortuitously, it was found that the compounds described herein are capable of interfering with the processing and export of viral mRNAs from the nucleus to the cytoplasm. Such compounds show an inhibition of HIV, adenovirus and coronavirus replication post-entry. The invention provides compounds that may be suitable for the treatment of HIV AIDS and other viral diseases.

In a first aspect, there is provided, a compound having the structure of Formula I:

I

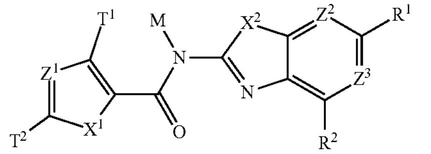

wherein, $X^1$ may be selected from S, O and N-$J^1$; $X^2$ may be selected from S, O and N-$J^2$; $Z^1$ may be selected from CH, N and CE; $Z^2$ may be selected from CH, N and $CR^4$; $Z^3$ may be selected from CH, N and $CR^3$; E may be selected from an optionally substituted 1-6 carbon linear, branched or cyclic alkyl, where optionally, one or more carbons may be substituted with a N or O or both, an optionally substituted aryl, an optionally substituted pyridine, $CH_2OH$, $CH_2CH_2OJ^3$, and $CH_2CH_2$-Q, wherein the optionally substituted alkyl, aryl and the pyridine have one or more H atoms independently substituted with OH, $CH_3$, $CH_2CH_3$, $CH_2CH_2CH_3$, $CH_2CH(CH_3)CH_3$, $CH(CH_3)CH_3$, $OCH_3$, $OCH_2CH_3$, $OCH_2CH_2CH_3$, $OCH_2CH(CH_3)CH_3$, $OCH(CH_3)CH_3$, CN, F, Cl, Br, I, and $CF_3$; $T^1$ may be selected from H, 1-6 carbon linear, branched or cyclic alkyl, where one or more alkyl carbons may be optionally substituted with a N or O or both and where one or more alkyl hydrogens may be optionally substituted with $J^8$, $CH_2OH$, $CH_2OJ^4$, $CH_2CH_2OJ^4$, $CH_2CH_2$-Q, $CO_2J^4$, $CONH(J^4)$, $CON(J^4)_2$, $NO_2$, CN, $CF_3$, $OCF_3$, $SO_2NH(J^4)$, $SO_2N(J^4)_2$ and $NJ^4J^4$; $T^2$ may be selected from H, 1-6 carbon linear, branched or cyclic alkyl, where one or more alkyl carbons may be optionally substituted with a N or O or both, and where one or more alkyl hydrogens may be optionally substituted with $J^9$, $NO_2$, $CF_3$, $OCF_3$, CN, $CH_2OH$, $CH_2OJ^5$, $CH_2CH_2OJ^5$, $CH_2CH_2$-Q, $CO_2J^5$, $CONH(J^5)$, $CON(J^5)_2$, $SO_2NH(J^5)$, $SO_2N(J^5)_2$ and $NJ^5J^5$; M may be selected from H, 1-6 carbon linear, branched or cyclic alkyl, where one or more alkyl carbons may be optionally substituted with a N or O or both, and where one or more alkyl hydrogens may be optionally substituted with $J^{10}$, $CH_2OH$, $CH_2CH_2OH$, CN, F, Cl, Br, I, $CF_3$, $NHCH_2CH_2Q$, $NH(J^6)$, $N(J^6)_2$, $CH_2CH_2OJ^6$, $CO_2J$ and $CON(J^6)_2$; Q may be selected from

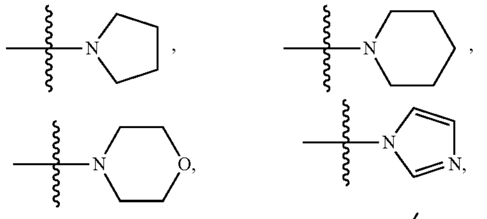

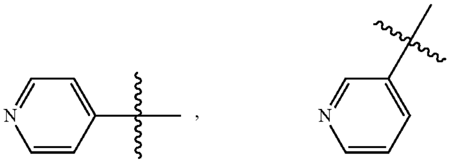

and

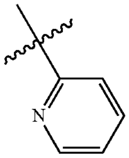

;

$R^1$ may be selected from H, 1-6 carbon linear, branched or cyclic alkyl, where one or more alkyl carbons may be optionally substituted with a N or O or both, $CH_2OH$, $CH_2CH_2OJ^7$, $CH_2CH_2$-Q, $CO_2J^7$, $CON(J^7)_2$, $NO_2$, CN, F, Cl, Br, I, $CF_3$, $OCF_3$, $SO_2J^7$, $SO_2N(J^7)_2$, $NJ^7J^7$ and $N_3$; $R^2$ may be selected from H, 1-6 carbon linear, branched or cyclic alkyl, where one or more alkyl carbons may be optionally substituted with a N or O or both, $CH_2OH$, $CH_2CH_2OJ^7$, $CH_2CH_2$-Q, $CO_2J^7$, $CON(J^7)_2$, $NO_2$, CN, F, Cl, Br, I, $CF_3$, $OCF_3$, $SO_2J^7$, $SO_2N(J^7)_2$, $NJ^7J^7$ and $N_3$; $J^1$ may be selected from H, 1-6 carbon linear, branched or cyclic alkyl, wherein one or more alkyl hydrogens are optionally independently substituted with $NH_2$ or NH (2-4 carbon linear or branched alkyl), $CH_2CH_2OH$, $CH_2CH_2OMe$, CN, $NH_2$, Q, $OCF_3$ and $CF_3$; $J^2$ may be selected from H, 1-6 carbon linear, branched or cyclic alkyl, wherein one or more alkyl hydrogens are optionally independently substituted with $NH_2$ or NH (2-4 carbon linear or branched alkyl), $CH_2CH_2OH$, CN, $NH_2$, Q, $OCF_3$ and $CF_3$; $J^3$ may be selected from H, 1-6 carbon linear, branched or cyclic alkyl, wherein one or more alkyl hydrogens are optionally independently substituted with $NH_2$ or NH (2-4 carbon linear or branched alkyl), $CH_2CH_2OH$, $CH_2CH_2OMe$, CN, $NH_2$, Q, $OCF_3$ and $CF_3$; $J^4$ may be selected from H, 1-6 carbon linear, branched or cyclic alkyl, wherein one or more alkyl hydrogens are optionally independently substituted with $NH_2$ or NH (2-4 carbon linear or branched alkyl), $CH_2CH_2OH$, $CH_2CH_2OMe$, CN, $NH_2$, Q, $OCF_3$ and $CF_3$; $J^5$ may be selected from H, 1-6 carbon linear, branched or cyclic alkyl, wherein one or more alkyl hydrogens are optionally independently substituted with $NH_2$ or NH (2-4 carbon linear or branched alkyl), $CH_2CH_2OH$, $CH_2CH_2OMe$, CN, $NH_2$, Q, $OCF_3$ and $CF_3$; $J^6$ may be selected from H, 1-6 carbon linear, branched or cyclic alkyl, wherein one or more alkyl hydrogens are optionally independently substituted with $NH_2$ or NH (2-4 carbon linear or branched alkyl), $CH_2CH_2OH$, $CH_2CH_2OMe$, CN, $NH_2$, Q, $OCF_3$ and $CF_3$; $J^7$ may be selected from H, 1-6 carbon linear, branched or cyclic alkyl, wherein one or more alkyl hydrogens are optionally independently substituted with $NH_2$ or NH (2-4 carbon linear or branched alkyl), $CH_2CH_2OH$, $CH_2CH_2OMe$, CN, $NH_2$, Q, $OCF_3$ and $CF_3$; $J^8$ may be selected from a 1-4 carbon linear or branched alkyl, a 1-4 carbon linear or branched O-alkyl, OH, $CH_2OH$, $CH_2OJ^4$, $CH_2CH_2OJ^4$, $CH_2CH_2$-Q, $CO_2J^4$, $CONH(J^4)$, $CON(J^4)_2$, $SO_2NH(J^4)$, $SO_2N(J^4)_2$, $NO_2$, CN, $NH_2$, $NJ^4J^4$, F, $CF_3$ and $OCF_3$; $J^9$ may be selected from a 1-4 carbon linear or branched alkyl, a 1-4 carbon linear or branched O-alkyl, OH, $CH_2OH$, $CH_2OJ^5$, $CH_2CH_2OJ^5$, $CH_2CH_2$-Q, $CO_2J^5$, CONH ($J^5$), $CON(J^5)_2$, $SO_2NH(J^5)$, $SO_2N(J^5)_2$, $NO_2$, CN, $NH_2$, $NJ^5J^5$, F, $CF_3$ and $OCF_3$; and $J^{10}$ may be selected from a 1-4 carbon linear or branched alkyl, a 1-4 carbon linear or branched O-alkyl, OH, $CH_2OH$, CN, $NH_2$, $NJ^6J^6$ and $CF_3$.

In a further aspect, there is provided, a compound having the structure of Formula II:

II

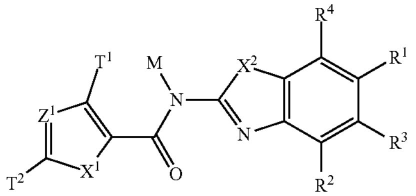

wherein, $X^1$ may be selected from S, O and N-$J^1$; $X^2$ may be selected from S, O and N-$J^2$; $Z^1$ may be selected from CH, N and CE; E may be selected from an optionally substituted 1-6 carbon linear, branched or cyclic alkyl, where optionally, one or more carbons may be substituted with a N or O or both, an optionally substituted aryl, an optionally substituted pyridine, $CH_2OH$, $CH_2CH_2OJ^3$, and $CH_2CH_2$-Q, wherein the optionally substituted alkyl, aryl and the pyridine have one or more H atoms independently substituted with OH, $CH_3$, $CH_2CH_3$, $CH_2CH_2CH_3$, $CH_2CH(CH_3)CH_3$, $CH(CH_3)CH_3$, $OCH_3$, $OCH_2CH_3$, $OCH_2CH_2CH_3$, $OCH_2CH(CH_3)CH_3$, $OCH(CH_3)CH_3$, CN, F, Cl, Br, I, and $CF_3$; $T^1$ may be selected from H, 1-6 carbon linear, branched or cyclic alkyl, where one or more alkyl carbons may be optionally substituted with a N or O or both and where one or more alkyl hydrogens may be optionally substituted with $J^8$, $CH_2OH$, $CH_2OJ^4$, $CH_2CH_2OJ^4$, $CH_2CH_2$-Q, $CO_2J^4$, $CONH(J^4)$, $CON(J^4)_2$, $NO_2$, CN, $CF_3$, $OCF_3$, $SO_2NH(J^4)$, $SO_2N(J^4)_2$ and $NJ^4J^4$; $T^2$ may be selected from H, 1-6 carbon linear, branched or cyclic alkyl, where one or more alkyl carbons may be optionally substituted with a N or O or both, and where one or more alkyl hydrogens may be optionally substituted with $J^9$, $NO_2$, $CF_3$, $OCF_3$, CN, $CH_2OH$, $CH_2OJ^5$, $CH_2CH_2OJ^5$, $CH_2CH_2$-Q, $CO_2J^5$, $CONH(J^5)$, $CON(J^5)_2$, $SO_2NH(J^5)$, $SO_2N(J^5)_2$ and $NJ^5J^5$; M may be selected from H, 1-6 carbon linear, branched or cyclic alkyl, where one or more alkyl carbons may be optionally substituted with a N or O or both, and where one or more alkyl hydrogens may be optionally substituted with $J^{10}$, $CH_2OH$, $CH_2CH_2OH$, CN, F, Cl, Br, I, $CF_3$, $NHCH_2CH_2Q$, $NH(J^6)$, $N(J^6)_2$, $CH_2CH_2OJ^6$, $CO_2J$ and $CON(J^6)_2$; Q may be selected from

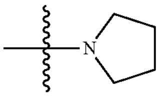 , 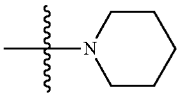 ,

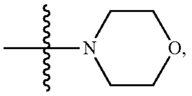 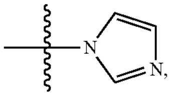

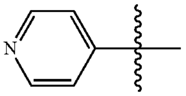 , 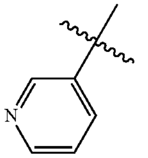 and

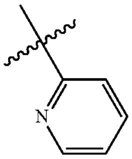 ;

$R^1$ may be selected from H, 1-6 carbon linear, branched or cyclic alkyl, where one or more carbons may be substituted with a N or O or both, $CH_2OH$, $CH_2CH_2OJ^7$, $CH_2CH_2$-Q, $CO_2J^7$, $CON(J^7)_2$, $NO_2$, CN, F, Cl, Br, I, $CF_3$, $OCF_3$, $SO_2J^7$, $SO_2N(J^7)_2$, N $J^7J^7$ and $N_3$; $R^2$ may be selected from H, 1-6 carbon linear, branched or cyclic alkyl, where one or more carbons may be substituted with a N or O or both, $CH_2OH$, $CH_2CH_2OJ^7$, $CH_2CH_2$-Q, $CO_2J^7$, $CON(J^7)_2$, $NO_2$, CN, F, Cl, Br, I, $CF_3$, $OCF_3$, $SO_2J^7$, $SO_2N(J^7)_2$, N $J^7J^7$ and $N_3$; $R^3$ may be selected from H, 1-6 carbon linear, branched or cyclic alkyl, where one or more carbons may be substituted with a N or O or both, $CH_2OH$, $CH_2CH_2OJ^7$, $CH_2CH_2$-Q, $CO_2J^7$, $CON(J^7)_2$, $NO_2$, CN, F, Cl, Br, I, $CF_3$, $OCF_3$, $SO_2J^7$, $SO_2N(J^7)_2$, N $J^7J^7$ and $N_3$; $R^4$ may be selected from H, 1-6 carbon linear, branched or cyclic alkyl, where one or more carbons may be substituted with a N or O or both, $CH_2OH$, $CH_2CH_2OJ^7$, $CH_2CH_2$-Q, $CO_2J^7$, $CON(J^7)_2$, $NO_2$, CN, F, Cl, Br, I, $CF_3$, $OCF_3$, $SO_2J^7$, $SO_2N(J^7)_2$, N $J^7J^7$ and $N_3$; $J^1$ may be selected from H, 1-6 carbon linear, branched or cyclic alkyl, $CH_2CH_2OH$, $CH_2CH_2OMe$, CN and $CF_3$, wherein one or more alkyl hydrogens may be optionally substituted with $NH_2$, $NHJ^{10}$, Q, $OCF_3$ and $CF_3$; $J^2$ may be selected from H, 1-6 carbon linear, branched or cyclic alkyl, $CH_2CH_2OH$, $CH_2CH_2OMe$, CN and $CF_3$, wherein one or more alkyl hydrogens may be optionally substituted with $NH_2$, $NHJ^{10}$, Q, $OCF_3$ and $CF_3$; $J^3$ may be selected from H, 1-6 carbon linear, branched or cyclic alkyl, $CH_2CH_2OH$, $CH_2CH_2OMe$, CN and $CF_3$, wherein one or more alkyl hydrogens may be optionally substituted with $NH_2$, $NHJ^{10}$, Q, $OCF_3$ and $CF_3$; $J^4$ may be selected from H, 1-6 carbon linear, branched or cyclic alkyl, $CH_2CH_2OH$, $CH_2CH_2OMe$, CN and $CF_3$, wherein one or more alkyl hydrogens may be optionally substituted with $NH_2$, $NHJ^{10}$, Q, $OCF_3$ and $CF_3$; $J^5$ may be selected from H, 1-6 carbon linear, branched or cyclic alkyl, $CH_2CH_2OH$, $CH_2CH_2OMe$, CN and $CF_3$, wherein one or more alkyl hydrogens may be optionally substituted with $NH_2$, $NHJ^{10}$, Q, $OCF_3$ and $CF_3$; $J^6$ may be selected from H, 1-6 carbon linear, branched or cyclic alkyl, $CH_2CH_2OH$, $CH_2CH_2OMe$, CN and $CF_3$, wherein one or more alkyl hydrogens may be optionally substituted with $NH_2$, $NHJ^{10}$, Q, $OCF_3$ and $CF_3$; and $J^7$ may be selected from H, 1-6 carbon linear, branched or cyclic alkyl, $CH_2CH_2OH$, $CH_2CH_2OMe$, CN and $CF_3$, wherein one or more alkyl hydrogens may be optionally substituted with $NH_2$, $NHJ^{10}$, Q, $OCF_3$ and $CF_3$; $J^8$ may be selected from a 1-4 carbon linear or branched alkyl, a 1-4 carbon linear or branched O-alkyl, OH, $CH_2OH$, $CH_2OJ^4$, $CH_2CH_2OJ^4$, $CH_2CH_2$-Q, $CO_2J^4$, $CONH(J^4)$, $CON(J^4)_2$, $SO_2NH(J^4)$, $SO_2N(J^4)_2$, $NO_2$, CN, $NH_2$, $NJ^4J^4$, F, $CF_3$ and $OCF_3$; $J^9$ may be selected from a 1-4 carbon linear or branched alkyl, a 1-4 carbon linear or branched O-alkyl, OH, $CH_2OH$, $CH_2OJ^5$, $CH_2CH_2OJ^5$, $CH_2CH_2$-Q, $CO_2J^5$, $CONH(J^5)$, $CON(J^5)_2$, $SO_2NH(J^5)$, $SO_2N(J^5)_2$, $NO_2$, CN, $NH_2$, $NJ^5J^5$, F, $CF_3$ and $OCF_3$; and $J^{10}$ may be selected from a 1-4 carbon linear or branched alkyl, a 1-4 carbon linear or branched O-alkyl, OH, $CH_2OH$, CN, $NH_2$, $NJ^6J^6$ and $CF_3$.

In a further aspect, there is provided, a pharmaceutical composition for treating a viral infection, comprising a compound described herein and a pharmaceutically acceptable carrier.

In a further aspect, there is provided, a use of a compound described herein, for treating a viral infection.

In a further aspect, there is provided, a use of a compound described herein in the manufacture of a medicament for treating a viral infection.

In a further aspect, there is provided, a method of treating a viral infection, the method comprising administering to a subject in need thereof, a compound described herein or a pharmaceutical composition thereof.

$X^1$ may be selected from S and O; $X^2$ may be selected from S and O; and $Z^1$ may be selected from CH and N. $X^1$ may be selected from S and O. $X^2$ may be selected from S and O. $Z^1$ may be selected from CH and N. T may be selected from H or 1-6 carbon linear, branched or cyclic alkyl; and $T^2$ may be selected from H, $NO_2$, $CF_3CN$, or a 1-6 carbon linear, branched or cyclic alkyl. $T^1$ may be selected from H or 1-6 carbon linear, branched or cyclic alkyl. $T^2$ may be selected from H, $NO_2$, $CF_3CN$, or a 1-6 carbon linear, branched or cyclic alkyl. M may be selected from H or $CH_3$. $R^1$ may be selected from H, $CH_3$, $CO_2J^7$, $CON(J^7)_2$, $NO_2$, CN, F, Cl, Br, I, $CF_3$, $OCF_3$, $SO_2J^7$ and $N_3$; $R^2$ may be selected from H, $CH_3$, 1-6 carbon linear, branched or cyclic alkyl, $CH_2OH$, $NO_2$, CN, F, Cl, Br, I, $CF_3$, $OCF_3$ and $N_3$; $R^3$ may be selected from H, 1-6 carbon linear, branched or cyclic alkyl, $CH_2OH$, $NO_2$, CN, F, Cl, Br, I, $CF_3$, $OCF_3$ and $N_3$; and $R^4$ may be selected from H, 1-6 carbon linear, branched or cyclic alkyl, $CH_2OH$, $NO_2$, CN, F, Cl, Br, I, $CF_3$, $OCF_3$ and $N_3$. $R^1$ may be selected from H, $CH_3$, $CO_2J^7$, $CON(J^7)_2$, $NO_2$, CN, F, Cl, Br, I, $CF_3$, $OCF_3$, $SO_2J^7$ and $N_3$. $R^2$ may be selected from H, $CH_3$, 1-6 carbon linear, branched or cyclic alkyl, $CH_2OH$, $NO_2$, CN, F, Cl, Br, I, $CF_3$, $OCF_3$ and $N_3$. $R^3$ may be selected from H, 1-6 carbon linear, branched or cyclic alkyl, $CH_2OH$, $NO_2$, CN, F, Cl, Br, I, $CF_3$, $OCF_3$ and $N_3$. $R^4$ may be selected from H, 1-6 carbon linear, branched or cyclic alkyl, $CH_2OH$, $NO_2$, CN, F, Cl, Br, I, $CF_3$, $OCF_3$ and $N_3$. Alternatively, $T^2$ may be selected from H, $NO_2$, $CF_3$, $CO_2J^5$, CN, or a 1-6 carbon linear, branched or cyclic alkyl.

$X^1$ may be S; $X^2$ may be selected from S and O; and $Z^1$ may be selected from CH and N. $X^1$ may be S. $X^2$ may be S. $X^2$ may be O. $Z^1$ may be N. $Z^1$ may be CH. $T^2$ may be selected from $CF_3$ and CN. $T^1$ may be H. $T^2$ may be $CF_3$. $T^2$ may be CN. M may be H. $R^1$ may be selected from H, $CO_2J^7$, $NO_2$, F, Cl, Br, I, $CF_3$, $OCF_3$, $SO_2J^7$ and $N_3$. $R^2$ may be H. $R^2$ may be Cl. $R^3$ may be H. $R^3$ may be Br. $R^4$ may be H. $R^1$ may be selected from H, $CH_3$, $CO_2J^7$, $CON(J^7)_2$, $NO_2$, CN, F, Cl, Br, I, $CF_3$, $OCF_3$, $SO_2J^7$ and $N_3$. $R^2$ may be selected from H, $CH_3$, 1-6 carbon linear, branched or cyclic alkyl, $CH_2OH$, $NO_2$, CN, F, Cl, Br, I, $CF_3$, $OCF_3$ and $N_3$. $R^3$ may be selected from H, 1-6 carbon linear, branched or cyclic alkyl, $CH_2OH$, $NO_2$, CN, F, Cl, Br, I, $CF_3$, $OCF_3$ and $N_3$. $R^4$ may be selected from H, 1-6 carbon linear, branched or cyclic alkyl, $CH_2OH$, $NO_2$, CN, F, Cl, Br, I, $CF_3$, $OCF_3$ and $N_3$.
The compound may be selected from one or more of:
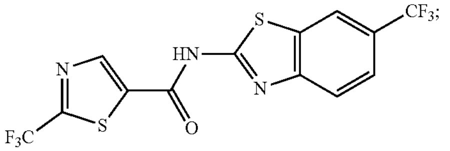 [SMILES: O=C(Nc1nc2ccc(C(F)(F)F)cc2s1)c1cnc(C(F)(F)F)s1]
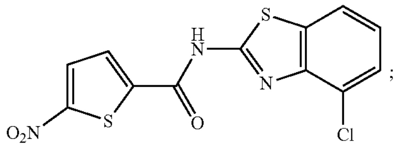
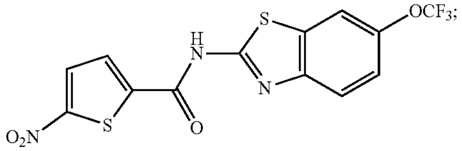
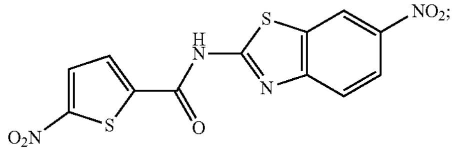
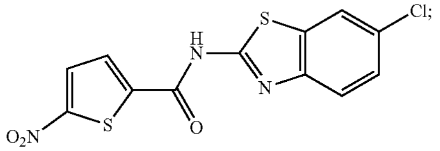
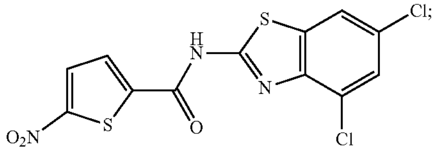
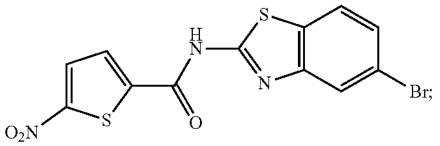
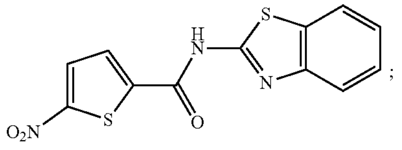
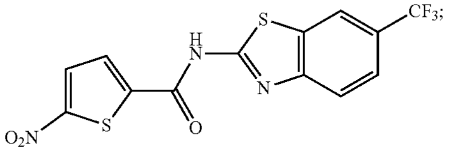
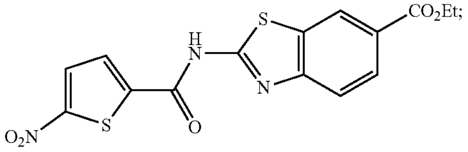
-continued
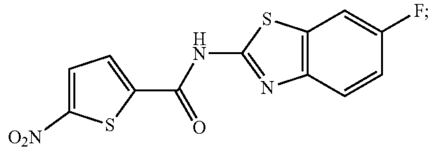
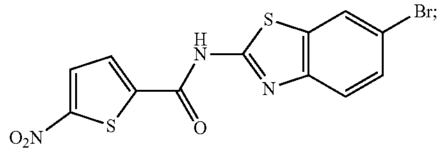
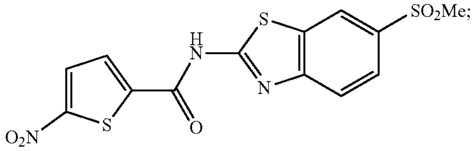
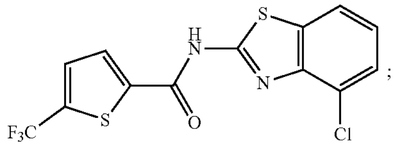
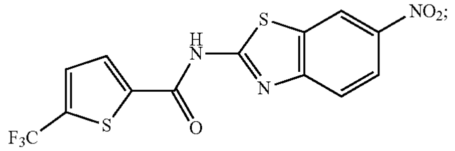
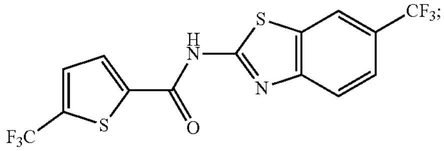
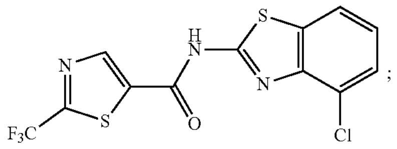
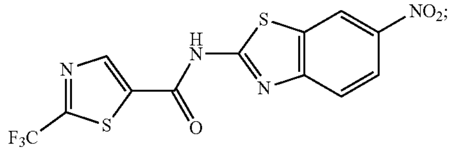
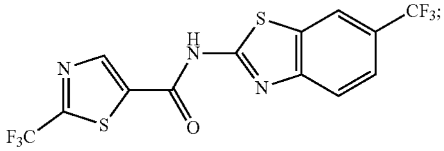 [SMILES: O=C(Nc1nc2ccc(C(F)(F)F)cc2s1)c1cnc(C(F)(F)F)s1]
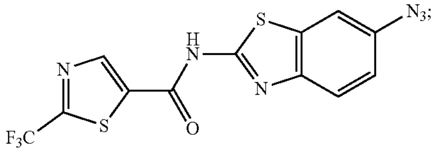
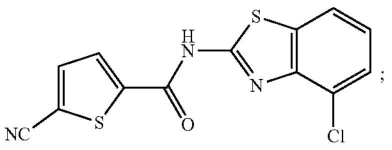

-continued

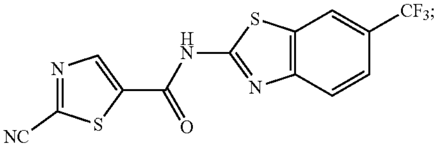

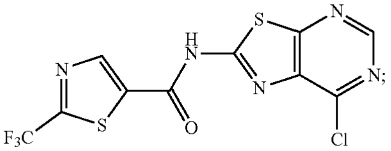

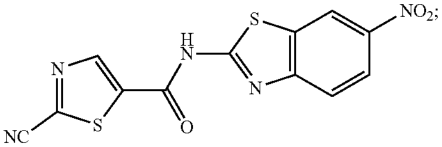

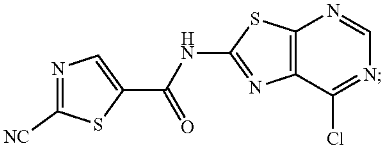

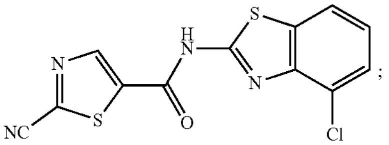

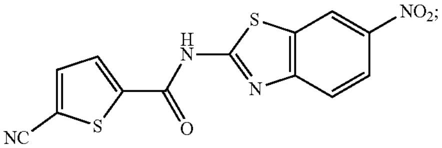

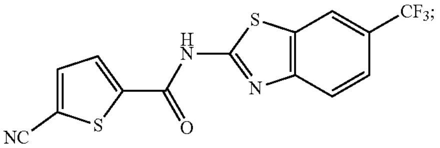

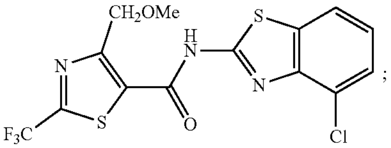

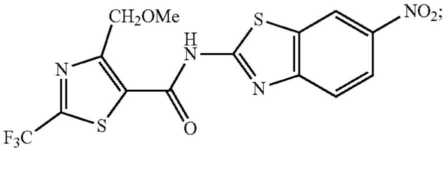

and

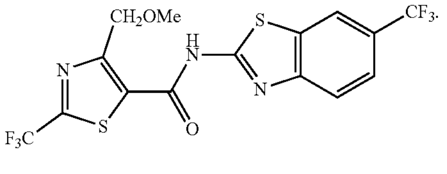

Alternatively, the compound may be selected from one or more of:

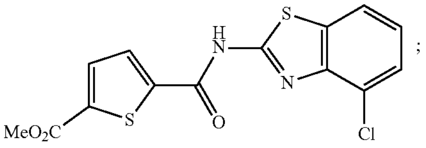

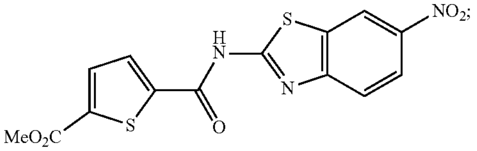

and

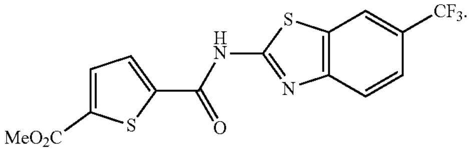

The compound may be

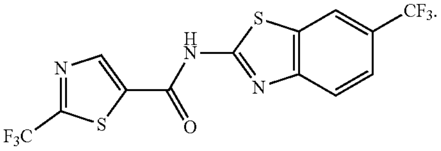

The viral infection may be selected from one or more of the following: HIV and adenoviral. Alternatively, the infection may be a coronavirus infection.

BRIEF DESCRIPTION OF DRAWINGS

FIG. 3: (A) plots of the anti-HIV-1 activity of GPS491 (12c) at increasing concentrations in CEM-GXR cells against wild-type subtype A (N54 WT Subtype A) and subtype B (NL4-3 WT Subtype B); (B) plots of the anti-HIV-1 activity of GPS488 (12a) at increasing concentrations in CEM-GXR cells against wild-type subtype A (N54 WT Subtype A) and subtype BNL4-3 WT Subtype B).

DETAILED DESCRIPTION

Figure 1A:
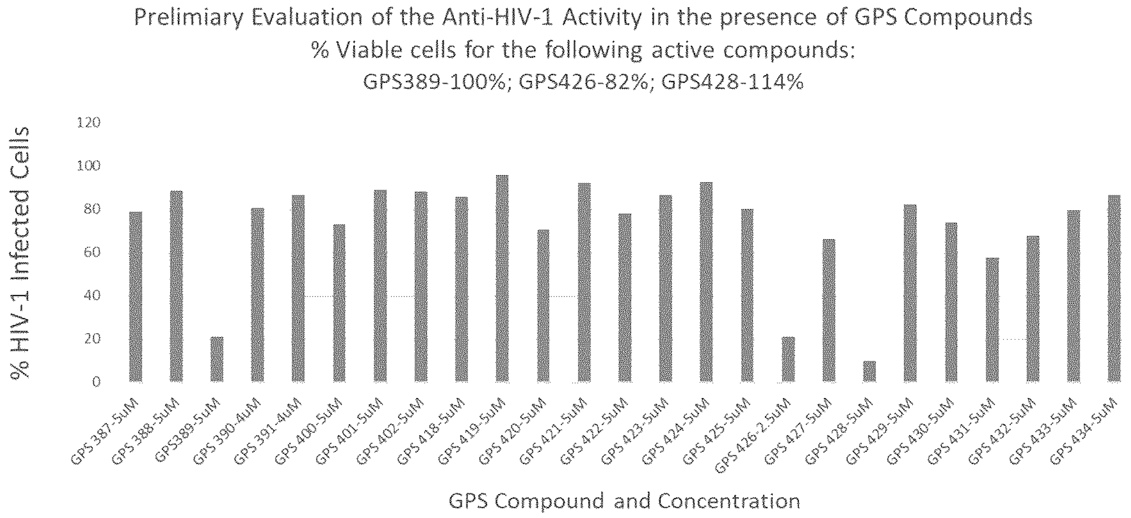
FIG. 1: (A) Preliminary evaluation of the first group GPS compounds (387-434) on anti-HIV-1 activities; (B) Preliminary evaluation of the second group GPS compounds (435-495) on anti-HIV-1 activities.

The following detailed description will be better understood when read in conjunction with the appended figures. For the purpose of illustrating the invention, the figures demonstrate embodiments of the present invention. However, the invention is not limited to the precise arrangements, examples, and instrumentalities shown.

Any terms not directly defined herein shall be understood to have the meanings commonly associated with them as understood within the art of the invention.

It will be understood by a person of skill that COOH and NR2 may include the corresponding ions, for example carboxylate ions and ammonium ions, respectively. Alternatively, where the ions are shown, a person of skill in the art will appreciate that the counter ion may also be present.

Those skilled in the art will appreciate that the point of covalent attachment of the moiety to the compounds as described herein may be, for example, and without limitation, cleaved under specified conditions. Specified conditions may include, for example, and without limitation, in vivo enzymatic or non-enzymatic means. Cleavage of the moiety may occur, for example, and without limitation, spontaneously, or it may be catalyzed, induced by another agent, or a change in a physical parameter or environmental parameter, for example, an enzyme, light, acid, temperature or pH. The moiety may be, for example, and without limitation, a protecting group that acts to mask a functional group, a group that acts as a substrate for one or more active or passive transport mechanisms, or a group that acts to impart or enhance a property of the compound, for example, solubility, bioavailability or localization.

In some embodiments, compounds as described herein, may be used for the treatment of viral infection. Alternatively, the compounds described herein may be used to interfere with viral RNA processing including splicing, polyadenylation, and export to the cytoplasm. Alternatively, the compounds that may be suitable for the treatment of HIV AIDS.

Compounds as described herein may be in the free form or in the form of a salt thereof. In some embodiment, compounds as described herein may be in the form of a pharmaceutically acceptable salt, which are known in the art (Berge S. M. et al., J. Pharm. Sci. $(1977)_{66}$(1):1-19). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid.

Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, i-ephenamine, N,N'-dibenzylethylenediamine or polyamine resins. In some embodiments, compounds as described herein may contain both acidic and basic groups and may be in the form of inner salts or zwitterions, for example, and without limitation, betaines.

Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formulas illustrated for the sake of convenience.

In some embodiments, pharmaceutical compositions as described herein may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents (used interchangeably herein) are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein micro-particles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in Remington: the Science & Practice of Pharmacy by Alfonso Gennaro, 20th ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene polyoxypropylene copolymers may be used to control the release of the compounds. Other potentially useful parenteral delivery systems for modulatory compounds include ethylene vinyl acetate copolymer particles, osmotic pumps, implantable infusion systems, and liposomes. Formulations for inhalation may contain excipients, for example, lactose, or may be aqueous solutions containing, for example, polyoxyethylene 9 lauryl ether, glycocholate and deoxycholate, or may be oily solutions for administration in the form of nasal drops, or as a gel.

Compounds or pharmaceutical compositions as described herein or for use as described herein may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition as described herein includes a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to an androgen independent form. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In general, compounds as described herein should be used without causing substantial toxicity. Toxicity of the compounds as described herein can be determined using standard techniques, for example, by testing in cell cultures or experimental animals and determining the therapeutic index, i.e., the ratio between the $LD_{50}$ (the dose lethal to 50% of the population) and the $LD_{100}$ (the dose lethal to 100% of the population). In some circumstances however, such as in severe disease conditions, it may be appropriate to administer substantial excesses of the compositions. Some compounds as described herein may be toxic at some concentrations. Titration studies may be used to determine toxic and non-toxic concentrations. Animal studies may be used to provide an indication if the compound has any effects on other tissues.

Compounds as described herein may be administered to a subject. As used herein, a "subject" may be a human, non-human primate, rat, mouse, cow, horse, pig, sheep, goat, dog, cat, etc. The subject may be suspected of having or at risk for having a viral infection, such as HIV AIDS and adenoviral infection. Alternatively, the infection may be a coronavirus infection. Diagnostic methods for various viral infections, are known to those of ordinary skill in the art.

Various alternative embodiments and examples are described herein. These embodiments and examples are illustrative and should not be construed as limiting the scope of the invention.

Materials and Methods

Cell Lines and Viruses

Indicator cell lines CEM-GXR were obtained from Dr. Mark Brockman (Simon Fraser University). (N)NRTI-resistant virus (E00443) was obtained from Dr. Zabrina Brumme (Simon Fraser University). HIV-1 CXCR4-tropic laboratory-adapted strain NL4-3, and IIIB, HIV-1 CCR5-tropic BaL, integrase inhibitor resistant virus (cat. #. 11845), protease inhibitor resistant virus (cat. #. 2948), and HIV-1 subtype A (cat. #. 4114) were obtained through the NIH AIDS Research and Reference reagent program, Division of AIDS, NIAID, NIH). Adenovirus C5 (HAdV-C5) and A549 cells were obtained from Dr. M. Brown (University of Toronto). Coronavirus strains 229E and OC43, HEK293 and Huh7 cell lines were obtained from ATCC. HeLa B2 cells (HeLa rtTA HIV-1Δmls) were previously described (Wong, Balachandran et al. 2011).

Synthesis and Characterization of Compounds

All chemicals were purchased from Sigma-Aldrich™ or Oakwood Chemicals™, and they were used without purification unless mentioned. All solvents were dried and kept under $N_2$. $^{1}H$, $^{13}C$, and $^{19}F$ NMR spectra were recorded at 400, 100, and 400 MHz, respectively, on a Bruker AC 400 Ultrashield™ 10 spectrophotometer. Chemical shifts are expressed in ppm, (δ scale).

When peak multiplicities are reported, the following abbreviations are used: s (singlet), d (doublet), dd (doublet of doublet), ddd (doublet of doublet of doublet), t (triplet) td (triplet of doublet), q (quartet), m (multiplet). Coupling constants are reported in Hz. All high-resolution mass spectra were recorded on a Thermo Scientific™ Q Exactive Orbitrap™ High Resolution Mass Spectrometer. Flash column chromatography was performed using silica gel (Silicycle™, Siliaflash™ F60, 40-63 μm, 230-400 mesh) or on a Biotage Isolera™ purification system, (PartnerTechAtvidaberg™ AB) using prepacked silica gel columns (Biotage™, part no. FSKO-1107-0010, FSKO-1107-0025, or FSKO-1107-0050).

Anti-HIV-1 Assays

The anti-HIV activity of the compounds was measured by a human T-cell reporter assay based on CEM-GXR cells. These cells express GFP due to the activation of the tat-dependent promoter upon HIV-1 infection, and the level of infection was monitored using Flow cytometric analysis (Guavasoft 2.2™ software, Guava HT8, Millipore™). Antiviral activity was evaluated in an assay that measures the inhibition of HIV-1 spread in a co-culture of CEM-GXR cells containing one percent of HIV-1 infected (GFP positive) cells. Infection was performed in a 96-well plate containing serial dilutions of the test compound and the half maximal effective concentration ($EC_{50}$) was determined on day 3.

Isolation of PBMC and Infection with HIV

Peripheral blood mononuclear cells (PBMC) were obtained from healthy HIV-negative donors following written informed consent and maintained in R10+ supplemented with 50 U/mL human IL-2. Study protocols were approved by Institutional Reviews Boards of the University of British Columbia-Providence Health Care Research Institute. PBMC were activated with 5 μg/ml PHA and infected 3 days later with viral stocks at a multiplicity of infection (MOI) of 0.01. At 6 h post-infection, cells were washed and resuspended in R10+ medium supplemented with 50 U/ml of IL-2 in the presence of GPS molecules or FTC as a control compound for an additional 11 days. The accumulation of p24Gag was quantified in culture supernatants at day 11 using an enzyme-linked immunosorbent assay (ELISA; Xpress Bio™), and the increase in p24Gag values was used as the measure of viral replication.

Adenovirus Infection Assay

A549 cells were seeded in 6-well plates at a density of 500,000 cells/well and infected 24 h post seeding at an input MOI of 100-400 of HAdV-C5. After 1 h adsorption period at 37° C., the inoculum was removed and replaced with culture medium containing DMSO or GPS491. Cells and medium are harvested together 24 h p.i. for end-point dilution in HEK293 cells to quantify infectious virus production. The Alamar Blue™ assay was used to determine the toxicity of the GPS491 compound against A549 cells. At 24 h post-seeding in a 96 well plate, the A549 cells were treated with the GPS491 compound or DMSO as the control for a 24 hr incubation period. Cell metabolic rate was measured by AlamarBlue™ as per manufacturer's directions. Cell viability was measured by trypan blue exclusion assay; cells were lifted with 2 mM EDTA and mixed with an equal volume of 0.3% trypan blue. Cells were counted with plastic disposable hemacytometers containing 10 grids; more than 95% of the cells excluded the dye. The metabolic and viability rate is compared to DMSO treated cells as a control. Error bars in all three panels represent standard deviation of three experiments.

Detection of Adenovirus Protein Expression

Protein lysates were analyzed by 10% Stain-Free gel (McDonald et al., 2008) and transferred to a polyvinylidene difluoride (PVDF) membranes using the Bio-Rad TurboBlot™ system according to the manufacturer's protocol. E1A and hexon blots were blocked at room temperature with 5% skim milk diluted in 0.05% Tween20 in ix PBS (PBS-T) for 1 h and then incubated with primary antibody overnight at 4° C. Following three PBS-T washes, the membrane is incubated with secondary antibody at room temperature for 1 h. For E1A analysis, blots were probed with polyclonal E1A primary antibody (Santa Cruz™, sc-430) and secondary anti-rabbit antibody conjugated to horseradish peroxidase (HRP, used a 1:5000 dilution in PBS-T). For hexon analysis, blots were probed with undiluted culture fluid from 2Hx-2 cells, which contain mouse anti-hexon antibodies, and secondary anti-mouse antibody conjugated to horseradish peroxidase (1:5000 dilution in PBS-T). For immunofluorescent detection of viral proteins, cells were fixed for 15 minutes with 4% paraformaldehyde, permeabilized with 0.1% Triton X-100 in PBS (PBT), then blocked with 5% bovine serum albumin (BSA) in PBT (BSA-PBT) at room temperature for 45 minutes. Cells were incubated with primary antibody at 37° C. for 45 minutes, washed three times with PBS, then incubated with secondary antibody for 45 minutes. The stained coverslip is washed twice with PBT and twice with PBS, then mounted in PBS containing DAPI (4',6'-diamidino-2-phenylindole) at 0.25 μg/mL, and stored at 4° C.

ViaCount Viability Assay

The ViaCount™ assay was performed with the Guava easyCyte 8HT™ flow cytometer according to the manufacturer's manual (Guava Technologies™, Inc., Hayward, CA, USA). In brief, CEM-GXR cells were seeded in 96-well plates 80000 cells/well in the absence or presence of compound in various concentrations. Twenty-four hours later, 25 μL of cell suspension was mixed with 225 μL of Guava ViaCount™ reagent, and the mixture was incubated for 5 min at room temperature. Sample acquisition and data analysis were performed with the selection of EasyFit™ analysis feature using the ViaCount™ software module.

Impact of Compounds on Alternative Splicing of the HIV Transcript by qRT-PCR in HeLa B2 Cells Quantitative RT-PCR assays using three different sets of primers located in introns or flanking an exon/intron junction to monitor HIV genomic expression (US, SS, MS pairs of primers) as described previously (Duffy 2012).

Impact of GPS491 Compound on Alternative Splicing of the E1A Transcript by RT-PCR in A549 Cells A549 cells were infected with adenovirus-C5 at a MOI of 100 for 1 h after which virus was removed and replaced with media containing DMSO or GPS491 (2.5 μM or 5 μM). Total RNA was extracted at 8 h, 16 h, or 24 h after virus infection. After cDNA generation, RT-PCR was performed using E1A specific primers.

Impact of GPS491 Compound on Adenovirus Viral DNA Replication in A549 Cells.

For adenovirus DNA analysis, cells were seeded on 6 cm plates at a density of $1\times10^6$ cells per plate. The next day, cells were infected with HAdV-C5 (MOI 100) for 1 h, inoculum was removed and replaced with medium containing DMSO or GPS491 (2.5 μM). At the indicated times post-infection, cells were collected and washed in 1×PBS. Cells were lysed using 200 uL lysis buffer (10 mM Tris-HCl [pH 8.0], 75 mM NaCl, 0.1% SDS, 0.5% NP-40, 0.5% Tween 20, 0.5 mg/ml proteinase K) at 56° C. for 4 to 5 h and the mixture was boiled for 15 min. Samples were centrifuged at 13000×g and supernatant was collected. All samples from a given experiment were processed at the same time. Adenovirus DNA levels were determined by qPCR as previously detailed in Grosso F. et al. (2017). J Virol. 91(3):e01623-16.

Coronavirus Infection Assay

Huh7 cells were infected with either the 229E (MOI 0.1) or the OC43 (MOI 1) strain of coronavirus. After 1 h adsorption period at 37° C., the inoculum was removed and replaced with culture medium containing DMSO or 10 μM GPS491. After either 2 days (229E infected cells) or 4 days (OC43 infected cells), the media was harvested for viral RNA quantitation by RT-qPCR and the infected cells were fixed to measure the presence of viral proteins (spike protein of 229E and nucleocapsid protein of OC43) by immunofluorescence microscopy. To measure the dose response effect of GPS491 on the 229E coronavirus, Huh7 cells were infected with 229E at an M.O.I of 0.1 for 1 h. Virus inoculum was removed and fresh media added containing 1% DMSO or varying doses of GPS491. After 2 days, media was harvested to quantitate viral RNA cells were fixed and 229E S expression was measured by immunofluorescence. All values are expressed relative to values detected in virus infected samples treated with DMSO alone. In some experiments, Huh7 cells were infected at MOI of 1 with either the 229E, OC43 or SARS-CoV2 strain. Cells were infected with viruses for 1 h then media removed and replaced with media containing DMSO or GPS491 at increasing concentrations. At either 4 days (OC43) or 2 days (229E, SARS-CoV2) after infection, media was harvested to measure levels of viral RNA and, in the case of SARS-CoV2, cells were fixed and stained to detect viral antigens (N and S proteins) by immunofluorescence microscopy.

Impacts of Compounds on Viral Protein Levels in HeLa B2 Cells and SR Protein Levels in Hela B2 Cells.

HeLa B2 cells were incubated in the presence of DMSO or indicated concentrations of GPS491 and provirus expression induced by the addition of 2 μg/ml doxycycline. After 24 h of treatment, cells were harvested in 1×PBS, 2 mM EDTA and cell pellet resuspended in RIPA buffer. Proteins levels were detected by western blot using antibodies to HIV-1 Gag (anti-p24), Env (anti-gp120), or Tat. To assess effects on SR protein expression, cells were harvested in RIPA buffer containing phosphatase inhibitors and lysates fractionated on StainFree™ SDS-PAGE gels. Western blots were probed with one of the following antibodies: mouse α-SRSF1 (Life Technologies™, Cat: 32-4500), rabbit α-SRSF2 (BD Pharmingen™, Cat: 556363), mouse α-SRSF3 (Life Technologies™, Cat: 33-4200), rabbit α-SRSF4 (Novus Biologicals™, Cat: 2-04144), rabbit α-SRSF5 (MBL, RN082PW), rabbit α-SRSF6 (Novus Biologicals™, Cat: NBP2-04142), rabbit α-SRSF7 (Abcam™, Cat: ab137247), and rabbit α-SRSF9 (MBL, Cat: RN081PW), rabbit α-Tra2p (Abcam™, Cat: ab31353), and rabbit α-GAPDH (Sigma™, Cat: G9545). The following secondary antibodies were used: α-mouse, horseradish peroxidase (HRP)-conjugated IgG (Jackson Immunoresearch Laboratories™, Cat: 715-036-150) or α-rabbit, HRP-conjugated IgG (Jackson Immunoresearch Laboratories™, Cat: 711-036-152). To test whether changes in protein migration were attributable to altered phosphorylation, extracts were treated with lambda phosphatase (New England Biolabs, Cat: P0753S) prior to running on gels. Following incubation with appropriate secondary antibody, blots were visualized by ECL (Perkin-Elmer), ECL Plus (Perkin-Elmer), or Clarity Western ECL substrate (BioRad). Chemiluminescence was imaged with a BioRad ChemiDoc Imaging System. Blots were subsequently probed for tubulin or GAPDH as loading controls. Quantification of the relative intensity of the detected bands was done using ImageLab software and normalized to corresponding bands of the loading control (GAPDH, tubulin, or total protein).

Reaction Schemes and Experimental Procedures

1. Preparation of diheteroarylamides 5a-l from 5-nitrothiophene-2-carboxylic acid 2

The synthesis of compounds 5a-l involved conversion of 5-nitrothiophene-2-carboxylic acid 2 (itself available by dichromate oxidation of aldehyde 1 in 82%) to acid fluoride 3 through reaction with TFFH-CsF, and reaction of this intermediate with the requisite N-TMS substituted 2-aminobenzothiazole 4a-l in the presence of TBAF (Zamiri and Grierson 2017). Due to their solubility in hexane, acid fluoride 2 was isolated as a 1:1 mixture with the fluorination reaction side-product N,N,N,N-tetramethylurea. However, as the use of acetonitrile as solvent for the coupling step favoured precipitation of the desired amide products 5a-i, the non-polar urea contaminant and other impurities were readily separated from the target amides by simple vacuum filtration. With the exception of compound 5b, whose isolation required a further column chromatography operation, vacuum filtration was sufficient to obtain amides 5a and 5c-l in >95% purity.

Scheme 1

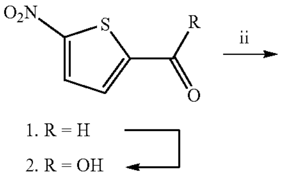

-continued

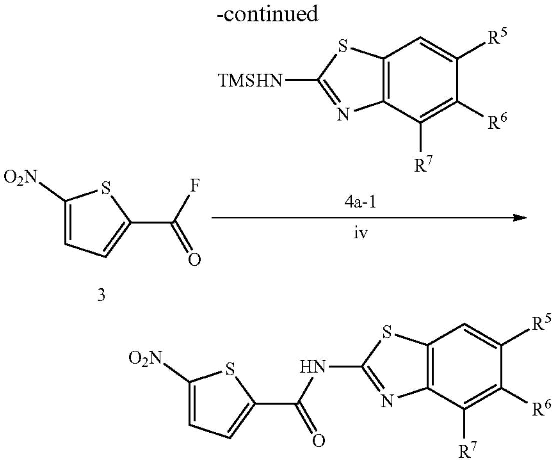

5a (GPS389) $R^5 = R^6 = H, R^7 = Cl$
5b (GPS426) $R^5 = OCF_3, R^6 = R^7 = H$
5c (GPS428) $R^5 = NO_2, R^6 = R^7 = H$
5d (GPS475) $R^5 = Cl, R^6 = R^7 = H$
5e (GPS476) $R^5 = R^7 = Cl, R^6 = H$
5f (GPS478) $R^5 = R^7 = H, R^6 = Br$
5g (GPS445) $R^5 = R^6 = R^7 = H$
5h (GPS484) $R^5 = CF_3, R^6 = R^7 = H$
5I (GPS477) $R^5 = CO_2Me, R^6 = R^7 = H$
5j (GPS474) $R^5 = F, R^6 = R^7 = H$
5k (GPS473) $R^5 = Br, R^6 = R^7 = H$
5l (GPS427) $R^5 = SO_2Me, R^6 = R^7 = H$

Reaction Scheme 1. Reagent and conditions: i) $K_2Cr_2O_7$, 5N $H_2SO_4$, 100° C., 2 h; ii) TFFH, CsF, MeCN, r.t., 12 h; iii) MeCN, TBAF (cat), 50° C., 12 h.

Preparation of 5-Nitrothiophene-2-carboxylic (2)

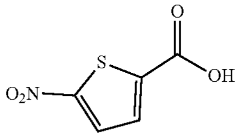 [SMILES: O=C(O)c1ccc([N+](=O)[O-])s1]

To a stirred solution of potassium dichromate (2.8 g, 11.5 mmol) in 5 N $H_2SO_4$ (40 mL) was added 5-nitro-2-thiophenecarboxaldehyde 1 (4 g, 25.5 mmol) and the reaction was heated at 100° C. for 2 h. The mixture was then cooled in an ice bath and diluted with water (40 mL). The resulting precipitate was collected by suction filtration, washed with ice water (5×20 mL), and dried under high vacuum to afford 2 as a green solid (3.6 g, 20.8 mmol, 82% yield).

$^1H$ NMR (400 MHz, DMSO-d6): δ=13.9 (s, 1H), 8.12 (d, J=4.1 Hz, 1H), 7.74 (d, J=4.1 Hz, 1H).

Preparation 5-nitrothiophene-2-carbonyl fluoride 3

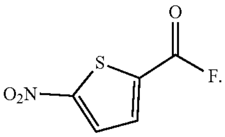

+ Urea contaminant

A mixture of thiophene-2-carboxylic acid 2 (800 mg, 4.64 mmol), TFFH (1.22 g, 4.64 mmol), and CsF (1.36 g, 8.96 mmol) in MeCN (24 mL) was stirred for 12 h at room temperature. The product mixture was then concentrated under reduced pressure, taken up in hexane and filtered to remove the cesium salts. The filtrate was concentrated to give a yellowish oil, which was dried under high vacuum for 5 h. Based on its $^1$H NMR spectrum, the isolated material corresponded to a 1:1 mixture of acid fluoride 3 and the 1,1,3,3-tetramethylurea side product. Peaks for trace amounts of unidentified material were also observed. The product mixture was estimated to contain 714 mg (4.08 mmol, 88% conversion) of acid fluoride 3.

$^1$H NMR (400 MHz, $CD_3CN$): δ=8.01 (m, 1H), 7.94 (m, 1H), 2.73 (s, 12H, NMe).

$^{19}$F NMR (400 MHz, $CD_3CN$): δ=23.74; $^{19}$F NMR (400 MHz, $CDCl_3$): δ=25.55.

General Procedure for the Preparation of N-TS-Amines 4a-l

N-Trimethylsilylated amines 4a-l were prepared by reaction of their corresponding heteroaromatic amine precursors (0.5 mmol) (dried under high vacuum for 12 h before use) in neat TMSCN (0.5 mL), with stirring under nitrogen at 70° C. for the indicated time. The excess TMSCN was removed under high vacuum and the derived N-silylated amine was used without purification in the amide bond forming reaction. The percent conversion of each amine to its N-silylated derivative was determined by $^1$H NMR analysis in $CDCl_3$ (passed through a basic alumina column prior to use).

4-Chloro-N-(trimethylsilyl)benzo[d]thiazol-2-amine (4a)

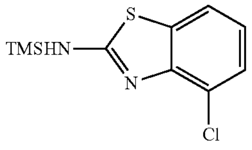

Prepared from 4-chlorobenzo[d]thiazol-2-amine. Heated for 30 min (yellow oil; 100% conversion).

$^1$H NMR (400 MHz, $CDCl_3$): δ=7.37 (d, J=7.7 Hz, 1H), 7.23 (d, J=7.8 Hz, 1H), 6.92 (t, J=7.7 Hz, 1H), 5.22 (s, 1H), 0.30 (s, 9H).

6-(Trifluoromethoxy)-N-(trimethylsilyl)benzo[d]thiazol-2-amine (4b)

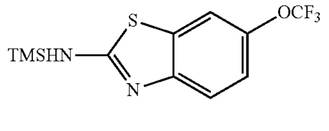

heated for 14 h; Brown oil; 95% conversion.

1H NMR ($CD_3CN$): δ=7.59 (d, 4J=2.2 Hz, 1H), 7.43 (d, 3J=8.8 Hz, 1H), 7.16-7.19 (dd, 3J=8.6 Hz, 4J=2.4 Hz, 1H), 5.97 (s, 1H), 0.33 (s, 9H).

6-Nitro-N-(trimethylsilyl)benzo[d]thiazol-2-amine (4c)

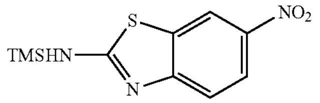

Prepared from 6-nitrobenzo[d]thiazol-2-amine. Heated for 12 h; yellow oil; 100% conversion $^1$H NMR (400 MHz, $CDCl_3$): δ=8.41 (s, 1H), 8.11 (d, J=9.0 Hz, 1H), 7.46 (d, J=8.9 Hz, 1H), 5.28 (s, 1H), 0.34 (s, 9H).

6-Chloro-N-(trimethylsilyl)benzo[d]thiazol-2-amine (4d)

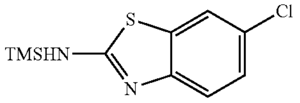

heated for 14 h; Off-white solid; 100% conversion.

1H NMR ($CD_3CN$): δ=7.62 (d, 4J=2.2 Hz, 1H), 7.36 (d, 3J=8.5 Hz, 1H), 7.21-7.24 (dd, 3J=8.4 Hz, 4J=2.1 Hz, 1H), 5.94 (s, 1H), 0.32 (s, 9H).

4,6-dichloro-N,N-bis(trimethylsilyl)benzo[d]thiazol-2-amine (4e)

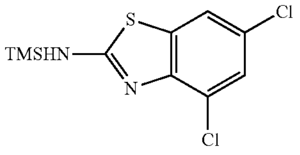

heated for 12 h; orange oil; 100% conversion.

$^1$H NMR (400 MHz, $CDCl_3$): δ=7.36 (d, J=2.1 Hz, 1H), 7.24 (d, J=2.0 Hz, 1H), 5.16 (s, 1H), 0.31 (s, 18H).

5-Bromo-N-(trimethylsilyl)benzo[d]thiazol-2-amine (4f)

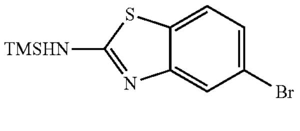

heated for 14 h; White solid; 95% conversion.

1H NMR ($CD_3CN$): 6=7.58 (d, 4J=2.0 Hz, 1H), 7.52 (d, 3J=8.4 Hz, 1H), 7.18-7.21 (dd, 3J=8.3 Hz, 4J=2.0 Hz, 1H), 6.03 (s, 1H), 0.32 (s, 9H).

N-(Trimethylsilyl)benzo[d]thiazol-2-amine (4g)

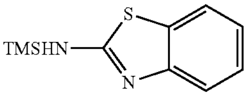

Prepared from benzo[d]thiazol-2-amine. Heated for 30 min (yellow oil; 100% conversion).

$^1$H NMR (400 MHz, $CDCl_3$): δ=7.41 (s, 2H), 7.13 (s, 1H), 6.93 (s, 1H), 4.91 (s, 1H), 0.21 (s, 9H).

6-(Trifluoromethyl)-N-(trimethylsilyl)benzo[d]thiazol-2-amine (4h)

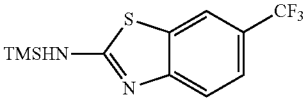

heated for 14 h; Brown oil; 100% conversion.

1H NMR ($CD_3CN$): δ=7.96 (d, 4J=1.8 Hz, 1H), 7.54-7.56 (dd, 3J=8.5 Hz, 4J=1.8 Hz, 1H), 7.47 (d, 3J=8.2 Hz, 1H), 6.13 (s, 1H), 0.34 (s, 9H).

Ethyl 2-((trimethylsilyl)amino)benzo[d]thiazole-6-carboxylate (4i)

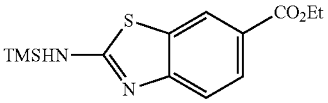

heated for 12 h; brown solid; 100% conversion.

$^1$H NMR (400 MHz, $CDCl_3$): δ=8.22 (s, 1H), 7.92 (d, J=7.2 Hz, 1H), 7.46 (d, J=7.4 Hz, 1H), 5.29 (bs, 1H), 4.30 (bs, 2H), 1.33 (bs, 3H), 0.31 (s, 9H).

6-Fluoro-N-(trimethylsilyl)benzo[d]thiazol-2-amine (4j)

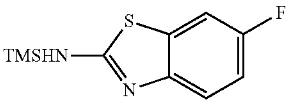

heated for 14 h; White solid; 95% conversion.

1H NMR ($CD_3CN$): 6=7.36-7.41 (m, 2H), 7.00-7.05 (ddd, 3J=9.4 Hz, 3J=8.9 Hz, 4J=2.6 Hz, 1H), 5.84 (s, 1H), 0.32 (s, 9H).

6-Bromo-N-(trimethylsilyl)benzo[d]thiazol-2-amine (4k)

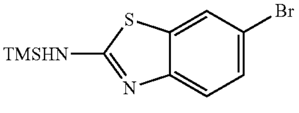

heated for 14 h; White solid; 95% conversion.

1H NMR ($CD_3CN$): δ=7.75 (d, 4J=2.0 Hz, 1H), 7.35-7.38 (dd, 3J=8.3 Hz, 4J=2.0 Hz, 1H), 7.30 (d, 3J=8.5 Hz, 1H), 5.95 (s, 1H), 0.32 (s, 9H).

6-(Methylsulfonyl)-N-(trimethylsilyl)benzo[d]thiazol-2-amine (4l)

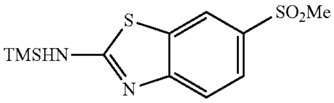

heated for 20 h; brown solid; 100% conversion.

$^1$H NMR (400 MHz, $CDCl_3$): δ=8.10 (s, 1H), 7.75 (d, J=8.0 Hz, 1H), 7.55 (d, J=8.0 Hz, 1H), 5.42 (s, 1H), 3.01 (s, 3H), 0.32 (s, 9H).

General Procedure for the Preparation of di(hetero)arylamides 5a-5l Via Coupling of N-TMS amines 4a-I with 5-nitrothiophene-2-carbonyl fluoride 3

For the coupling experiments, the acid fluoride 3—urea mixture containing 4.08 mmol of 3 was dissolved in MeCN (6 mL). Aliquots (1.5 mL) of this stock solution (containing 179 mg, 1.02 mmol, 1.28 equivalents of 3) were then added to a series of reaction vessels, each containing a different TMS-amine 4 (0.8 mmol). This was quickly followed by the addition of 1 M TBAF in THF (10 μL, 0.01 mmol) to each reaction vessel. The resultant mixtures were stirred at 50° C. for 12 h. The desired amide products 5a-I precipitated from the reaction, and, with the exception of 5b, were isolated pure by simple vacuum filtration.

N-(4-Chlorobenzo[d]thiazol-2-yl)-5-nitrothiophene-2-carboxamide (5a)

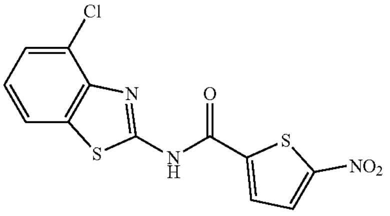 [SMILES: O=C(Nc1nc2c(Cl)cccc2s1)c1ccc([N+](=O)[O-])s1]

From N-TMS amine 4a. The precipitated product was washed with MeCN and then hexanes to afford 5a as a yellow solid; 40% (108 mg, 0.32 mmol).

$^1$H NMR (400 MHz, DMSO-$d_6$): δ=13.73 (s, 1H), 8.32 (d, J=4.2 Hz, 1H), 8.20 (d, J=4.2 Hz, 1H), 8.02 (d, J=8.0 Hz, 1H), 7.57 (d, J=7.8 Hz, 1H), 7.34 (t, J=7.9 Hz, 1H).

$^{13}$C NMR (100 MHz, DMSO-$d_6$): δ=154.7, 133.3, 130.6, 130.2, 126.5, 124.9, 121.0 (5 carbons are missing).

DEPT 135 NMR (100 MHz, DMSO-$d_6$): δ=130.6, 130.2, 126.5, 124.9, 121.0 HRMS (HESI): m/z $[M-H]^-$ calcd for $C_{12}H_5ClN_3O_3S_2$: 337.94663; found: 337.94647.

5-Nitro-N-(6-(trifluoromethoxy)benzo[d]thiazol-2-yl)thiophene-2-carboxamide (5b)

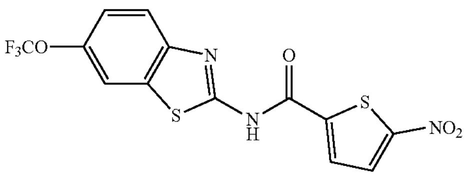 [SMILES: O=C(Nc1nc2ccc(OC(F)(F)F)cc2s1)c1ccc([N+](=O)[O-])s1]

From N-TMS amine 4b. The precipitated product was further purified by flash column chromatography (EtOAc/MeOH 9:1) to remove minor impurities. Compound 5b was obtained as a yellow solid; 22% (70 mg, 0.18 mmol).

$^{1}$H NMR (400 MHz, Acetone-$d_6$): δ=8.19 (d, J=4.2 Hz, 1H), 8.11 (d, J=4.3 Hz, 1H), 8.04 (s, 1H), 7.83 (d, J=8.8 Hz, 1H), 7.45 (d, J=8.8 Hz, 1H).

$^{13}$C NMR (100 MHz, Acetone-$d_6$): δ=162.4, 162.3, 156.1, 146.2, 145.7, 144.7, 133.3, 130.7, 130.2, 121.6 (q, J=255.0 Hz), 121.3, 116.0.

$^{19}$F NMR (400 MHz, Acetone-$d_6$): δ=−58.86.

5-Nitro-N-(6-nitrobenzo[d]thiazol-2-yl)thiophene-2-carboxamide (5c)

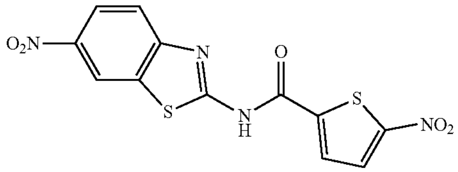 [SMILES: O=C(Nc1nc2ccc([N+](=O)[O-])cc2s1)c1ccc([N+](=O)[O-])s1]

From N-TMS amine 4c. The precipitated product was washed with MeCN and then hexanes to afford 5c as a yellow solid; 45% (126 mg, 0.36 mmol).

$^{1}$H NMR (400 MHz, DMSO-$d_6$): δ=13.91 (s, 1H), 9.07 (s, 1H), 8.30 (dd, J=2.4, 9.0 Hz, 1H), 8.22 (m, 2H), 7.90 (dd, J=8.8 Hz, 1H).

$^{13}$C NMR (100 MHz, DMSO-$d_6$): δ=154.6, 143.3, 130.8, 130.2, 122.2, 119.4, (6 carbons are missing).

DEPT 90 NMR (100 MHz, DMSO-$d_6$): δ=130.8, 130.2, 122.2, 119.4.

HRMS (HESI): m/z $[M-H]^-$ calcd for $C_{12}H_5N_4O_5S_2$: 348.97068; found: 348.97015.

N-(6-Chlorobenzo[d]thiazol-2-yl)-5-nitrothiophene-2-carboxamide (5d)

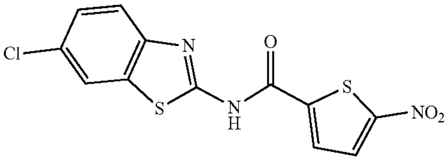 [SMILES: O=C(Nc1nc2ccc(Cl)cc2s1)c1ccc([N+](=O)[O-])s1]

From N-TMS amine 4d. The precipitated product was washed with MeCN and then hexanes to afford 5d as a yellow solid; 80% (218 mg, 0.64 mmol).

$^{1}$H NMR (400 MHz, DMSO-$d_6$): δ=13.60 (s, 1H), 8.13-8.18 (m, 3H), 7.70-7.72 (m, 1H), 7.50 (dd, J=2.21, 8.59 Hz, 1H).

$^{13}$C NMR (100 MHz, DMSO-$d_6$): δ=154.3, 130.3, 130.2, 128.2, 128.0, 127.0, 121.9, (5 carbons are missing).

DEPT 90 NMR (100 MHz, DMSO-$d_6$): δ=130.3, 130.2, 127.0, 121.9.

N-(4,6-Dichlorobenzo[d]thiazol-2-yl)-5-nitrothiophene-2-carboxamide (5e)

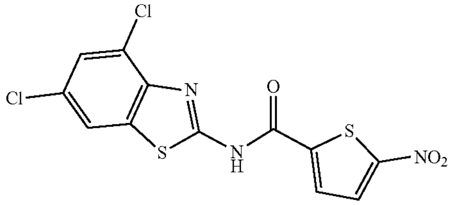 [SMILES: O=C(Nc1nc2c(Cl)cc(Cl)cc2s1)c1ccc([N+](=O)[O-])s1]

From 4e. The precipitated product was washed with MeCN and then hexanes to afford 5e as a greenish yellow solid; 70% (210 mg, 0.56 mmol).

$^{1}$H NMR (400 MHz, DMSO-$d_6$): δ=13.82 (s, 1H), 8.15-8.38 (m, 3H), 7.72 (s, 1H).

N-(5-Bromobenzo[d]thiazol-2-yl)-5-nitrothiophene-2-carboxamide (5f)

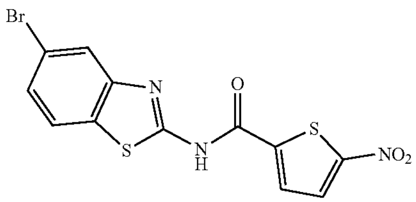 [SMILES: O=C(Nc1nc2cc(Br)ccc2s1)c1ccc([N+](=O)[O-])s1]

From 4f. The precipitated product was washed with MeCN and then hexanes to afford 5f as a yellow solid; 54% (164 mg, 0.43 mmol).

$^{1}$H NMR (400 MHz, DMSO-$d_6$): δ=13.66 (s, 1H), 8.17-8.21 (m, 2H), 8.01 (d, J=8.4 Hz, 1H), 7.93 (s, 1H), 7.52 (dd, J=2.1, 8.5 Hz, 1H).

$^{13}$C DEPT90 NMR (100 MHz, DMSO-$d_6$): δ=130.2, 126.6, 124.0.

N-(Benzo[d]thiazol-2-yl)-5-nitrothiophene-2-carboxamide (5g)

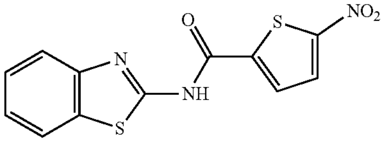 [SMILES: O=C(Nc1nc2ccccc2s1)c1ccc([N+](=O)[O-])s1]

From 4g. The precipitated product was washed with MeCN and then hexanes to afford 5g as a yellow solid; 55% (133 mg, 0.44 mmol).

$^{1}$H NMR (400 MHz, DMSO-$d_6$): δ=13.61 (s, 1H), 7.98-8.18 (m, 3H), 7.69 (s, 1H), 7.49 (t, J=7.6 Hz, 1H), 7.36 (t, J=7.6 Hz, 1H).

$^{13}C$ NMR (100 MHz, DMSO-$d_6$): δ=154.0, 130.2, 130.1, 126.9, 124.1, 122.4, (6 carbons are missing).

DEPT 135 NMR (100 MHz, DMSO-$d_6$): δ=130.2, 130.1, 126.8, 124.1, 122.4.

5-Nitro-N-(6-(trifluoromethyl)benzo[d]thiazol-2-yl) thiophene-2-carboxamide (5h)

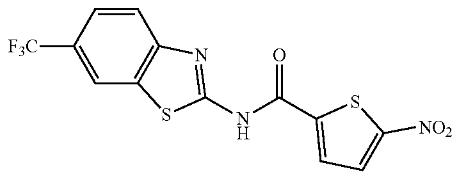 [SMILES: O=C(Nc1nc2ccc(C(F)(F)F)cc2s1)c1ccc([N+](=O)[O-])s1]

From 4h. The precipitated product was washed with MeCN and then hexanes to afford 5h as a yellow solid; 60% (180 mg, 0.48 mmol).

$^1H$ NMR (400 MHz, DMSO-$d_6$): δ=13.77 (s, 1H), 8.51 (s, 1H), 8.18 (d, J=4.2 Hz, 1H), 8.16 (bs, 1H), 7.88 (m, 1H), 7.78 (dd, J=8.6, 1.7 Hz, 1H).

$^{13}C$ NMR (100 MHz, DMSO-$d_6$): δ=154.4, 130.5, 130.2, 128.5, 125.8, 124.5 (q, J=270.4 Hz), 124.2 (q, J=32.1 Hz), 123.4, 120.3, (4 carbons missing).

DEPT 90 NMR (100 MHz, DMSO-$d_6$): δ=130.5, 130.2, 123.4, 120-3.

$^{19}F$ NMR (400 MHz, DMSO-$d_6$): δ=−59.62.

Ethyl 2-(5-nitrothiophene-2-carboxamido)benzo[d] thiazole-6-carboxylate (5i)

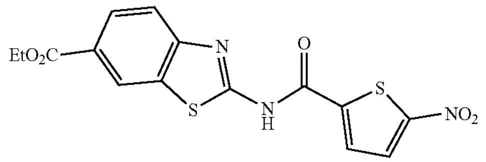 [SMILES: CCOC(=O)c1ccc2nc(NC(=O)c3ccc([N+](=O)[O-])s3)sc2c1]

From 4i. The precipitated product was washed with MeCN and then hexanes to afford 5i as a greenish yellow solid; 88% (264 mg, 0.70 mmol).

$^1H$ NMR (400 MHz, DMSO-$d_6$): δ=13.72 (s, 1H), 8.60 (s, 1H), 8.00-8.16 (m, 3H), 7.75 (m, 1H), 4.32 (q, J=7.1 Hz, 2H), 1.34 (t, J=7.1 Hz, 3H).

$^{13}C$ NMR (100 MHz, DMSO-$d_6$): δ=165.3, 154.2, 130.4, 130.2, 127.6, 125.3, 124.1, 60.9, 14.2, (6 carbons are missing).

DEPT 135 NMR (100 MHz, DMSO-$d_6$): δ=130.4, 130.1, 127.6, 124.1, 60.9, 14.2.

N-(6-Fluorobenzo[d]thiazol-2-yl)-5-nitrothiophene-2-carboxamide (5j)

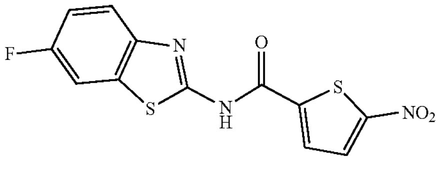 [SMILES: O=C(Nc1nc2ccc(F)cc2s1)c1ccc([N+](=O)[O-])s1]

From 4j. The precipitated product was washed with MeCN and then hexanes to afford 5j as a yellow solid; 79% (205 mg, 0.63 mmol).

$^1H$ NMR (400 MHz, DMSO-$d_6$): δ=13.55 (s, 1H), 8.10-8.18 (m, 2H), 7.92 (dd, J=2.7, 8.7 Hz, 1H), 7.74 (bs, 1H), 7.33 (td, J=2.8, 9.1 Hz, 1H).

$^{13}C$ NMR (100 MHz, DMSO-$d_6$): δ=168.3, 160.1, 157.7, 154.3, 147.4, 130.3, 130.2, 114.9, 114.7, 108.5, (2 carbons missing).

DEPT 90 NMR (100 MHz, DMSO-$d_6$): δ=130.3, 130.2, 114.9, 114.7.

$^{19}F$ NMR (400 MHz, $CDCl_3$): δ=−117.57.

N-(6-Bromobenzo[d]thiazol-2-yl)-5-nitrothiophene-2-carboxamide (5k)

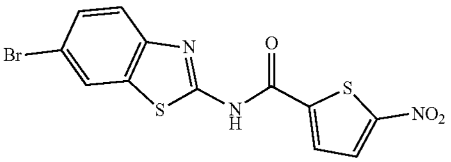

From 4k. The precipitated product was washed with MeCN and then hexanes to afford 5k as a yellow solid; 45% (138 mg, 0.36 mmol).

$^1H$ NMR (400 MHz, DMSO-$d_6$): δ=13.60 (s, 1H), 8.18-8.28 (m, 3H), 7.60-7.6 (m, 2H).

$^{13}C$ NMR (100 MHz, DMSO-$d_6$): δ=154.3, 130.4, 130.2, 129.7, 124.7, 116.1, (6 carbons are missing).

DEPT 135 NMR (100 MHz, DMSO-$d_6$): δ=130.3, 130.2, 129.6, 124.7.

N-(6-(Methylsulfonyl)benzo[d]thiazol-2-yl)-5-nitrothiophene-2-carboxamide (5l-GPS427)

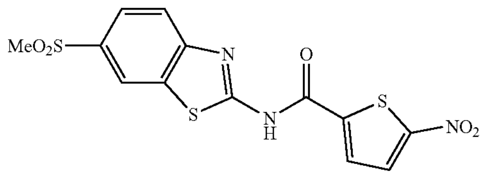 [SMILES: CS(=O)(=O)c1ccc2nc(NC(=O)c3ccc([N+](=O)[O-])s3)sc2c1]

From 4l. The precipitated product was washed with MeCN and then hexanes to afford 5l as a yellow solid; 74% (226 mg, 0.59 mmol).

$^1H$ NMR (400 MHz, DMSO-$d_6$): δ=13.84 (s, 1H), 8.69 (s, 1H), 8.22 (m, 2H), 8.00 (dd, J=1.8, 8.5 Hz, 1H), 7.95 (d, J=8.2 Hz, 1H), 3.26 (s, 3H).

$^{13}C$ NMR (100 MHz, DMSO-$d_6$): δ=154.5, 135.9, 130.6, 130.2, 125.4, 122.5, 44.0, (6 carbons are missing).

DEPT 135 NMR (100 MHz, DMSO-$d_6$): δ=130.6, 130.2, 125.4, 122.5.

2. Preparation of amides 8a-c from 5-trifluoromethylthiophene-2-carboxylic acid To access the target amides 8a-c, the method to prepare compounds 5a-i was modified such that the N-TMS amines 4a, 4b and 4h were reacted with the in situ generated acid fluoride 7. Further, in this "one pot" operation, the presence of CsF in the reaction medium eliminated the need to add TBAF to initiate the coupling reaction.

Scheme 2

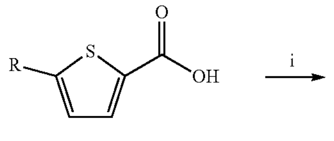

6a R = $CF_3$
6b. R = $CO_2Me$
6c. R = CN

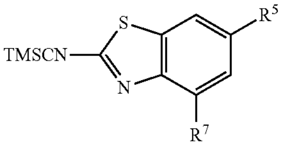

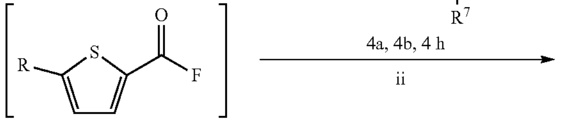

7a R = $CF_3$
7b. R = $CO_2Me$
7c. R = CN

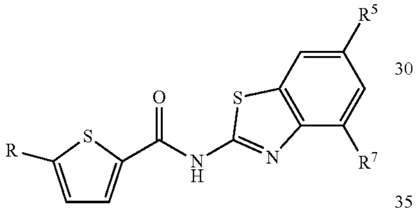

8a. R = CF3, R5 = H, R7 = Cl
8b. R = CF3, R5 = NO2, R7 = H
8c. R = CF3, R = CF3, R7 = H
8d. R = CO2Me, R5 = NO2, R7 = H
8e. R = CN, R5 = CF3, R7 = H
8f R = CN, R5 = H, R7 = Cl

Reagents and conditions: i)) TFFH, CsF, MeCN, r.t., 12 h; iii) MeCN, TBAF (cat), 50° C., 12 h.

N-(4-Chlorobenzo[d]thiazol-2-yl)-5-(trifluoromethyl)thiophene-2-carboxamide (8a)

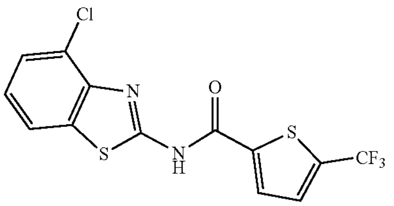 [SMILES: O=C(Nc1nc2c(Cl)cccc2s1)c1ccc(C(F)(F)F)s1]

A mixture of 5-trifluoromethylthiophene-2-carboxylic acid 6a (115 mg, 0.6 mmol), TFFH (160 mg, 0.6 mmol), and CsF (160 mg, 1.05 mmol) in MeCN (3 mL) was stirred for 12 h at room temperature. To the mixture containing the in situ generated acid fluoride 7a was added a solution of TMS-amine 4a (0.4 mmol) in MeCN (3 mL). The resultant mixture was stirred at 50° C. for 48 h. It was then concentrated under reduced pressure and the solid obtained was silica-gel flash column chromatographed (0-100% EtOAc in Hex) to afford 8a as a pale pink solid in 66% (95 mg, 0.26 mmol).

$^1$H NMR (400 MHz, DMSO-$d_6$): δ=13.62 (s, 1H), 8.40 (s, 1H), 8.02 (d, J=7.9 Hz, 1H), 7.90 (d, J=4.1 Hz, 1H), 7.57 (d, J=7.8 Hz, 1H), 7.34 (t, J=7.9 Hz, 1H).

$^{13}$C NMR (100 MHz, DMSO-$d_6$): δ=159.7, 159.2, 145.4, 141.2, 134.7 (q, J=37.8 Hz), 133.3, 131.3, 126.4, 124.8, 124.6, 121.9 (q, J=271.2 Hz), 121.0, (one carbon is missing).

DEPT 135 $^{13}$C NMR (100 MHz, DMSO-$d_6$): δ=131.3, 126.4, 124.8, 121.0.

$^{19}$F NMR (400 MHz, DMSO-$d_6$): δ=−54.73.

N-(6-nitrobenzo[d]thiazol-2-yl)-5-(trifluoromethyl)thiophene-2-carboxamide (8b)

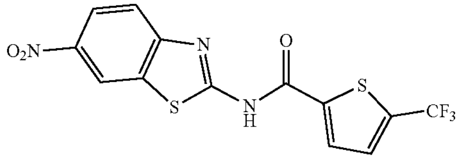 [SMILES: O=C(Nc1nc2ccc([N+](=O)[O-])cc2s1)c1ccc(C(F)(F)F)s1]

A mixture of carboxylic acid 6a (115 mg, 0.6 mmol), TFFH (160 mg, 0.6 mmol), and CsF (300 mg, 2.00 mmol) in MeCN (3 mL) was stirred for 12 h at room temperature. To the mixture containing the in situ generated acid fluoride 7a was added a solution of TMS-amine 4b (0.4 mmol) in MeCN (3 mL). The resultant mixture was stirred at 50° C. for 48 h. It was then concentrated under reduced pressure and the solid obtained was silica-gel flash column chromatographed (Hex/EtOAc 7:3) to afford 8b as a pale yellow solid in 16% (23.5 mg, 0.06 mmol).

$^1$H NMR (400 MHz, DMSO-$d_6$): δ=13.78 (s, 1H), 9.10 (s, 1H), 8.30-8.34 (m, 2H), 7.91-7.94 (m, 2H).

$^{19}$F NMR (400 MHz, DMSO-$d_6$): δ=−54.73.

5-(trifluoromethyl)-N-(6-(trifluoromethyl)benzo[d]thiazol-2-yl)thiophene-2-carboxamide (8c)

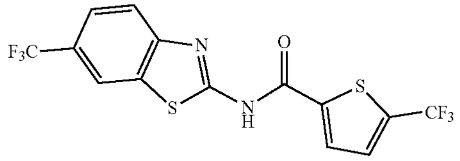 [SMILES: O=C(Nc1nc2ccc(C(F)(F)F)cc2s1)c1ccc(C(F)(F)F)s1]

A mixture of carboxylic acid 6 (115 mg, 0.6 mmol), TFFH (160 mg, 0.6 mmol), and CsF (500 mg, 3.30 mmol) in MeCN (3 mL) was stirred for 12 h at room temperature. To the mixture containing the in situ generated acid fluoride 7 was added a solution of TMS-amine 4h (0.4 mmol) in MeCN (3 mL). The resultant mixture was stirred at 50° C. for 48 h. It was then concentrated under reduced pressure and the solid obtained was silica-gel flash column chromatographed (Hex/EtOAc 7:3) to afford 8c as a pale yellow solid in 48% (76 mg, 0.19 mmol).

$^1$H NMR (400 MHz, acetone-$d_6$): δ=8.43 (bs, 1H), 8.30 (dt, J=1.4, 4.0 Hz, 1H), 7.93 (d, J=8.6 Hz, 1H), 7.79 (m, 2H).

$^{13}$C NMR (100 MHz, acetone-$d_6$): δ=162.7, 161.6, 150.9, 142.7, 136.8 (q, J=38.2 Hz), 133.1, 131.5, 131.3 (q, J=3.6

Hz), 126.1 (q, J=32.7 Hz), 125.6 (q, J=271.2 Hz), 124.1 (q, J=3.1 Hz), 123.0 (q, J=271.2 Hz), 121.4, 120.5 (q, J=3.9 Hz).

DEPT 135 $^{13}$C NMR (100 MHz, acetone-$d_6$): δ=131.5, 131.3 (q, J=3.6 Hz), 124.1 (q, J=3.1 Hz), 121.4, 120.5 (q, J=3.9 Hz).

$^{19}$F NMR (400 MHz, acetone-$d_6$): δ=−56.74, −61.64.

Methyl 5-((6-nitrobenzo[d]thiazol-2-yl)carbamoyl) thiophene-2-carboxylate (8d)

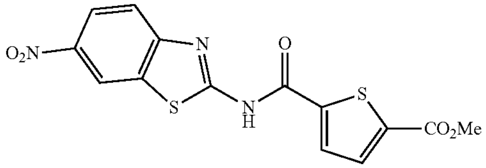 [SMILES: COC(=O)c1ccc(C(=O)Nc2nc3ccc([N+](=O)[O-])cc3s2)s1]

A mixture of 5-(methoxycarbonyl)thiophene-2-carboxylic acid 6b (111.6 mg, 0.6 mmol), TFFH (160 mg, 0.6 mmol), and CsF (160 mg, 1.05 mmol) in MeCN (3 mL) was stirred for 12 h at room temperature. The in situ generated acid fluoride 7b (0.6 mmol) was added in one portion to the reaction vessel containing neat 4b (0.7 mmol) at room temperature. This was quickly followed by addition of 1 M TBAF in THF (10 μL, 0.01 mmol). The reaction mixture was stirred at 50° C. for 48 h. The precipitated product was isolated by suction filtration and washed with MeCN and hexanes. Compound 8d was obtained as a very pale green solid (195 mg, 77%).

$^1$H NMR (400 MHz, DMSO-$d_6$): δ=13.68 (s, 1H), 9.09 (s, 1H), 8.30 (m, 2H), 7.91-7.93 (m, 2H), 3.88 (s, 3H).

5-Cyano-N-(6-(trifluoromethyl)benzo[d]thiazol-2-yl) thiophene-2-carboxamide (8e)

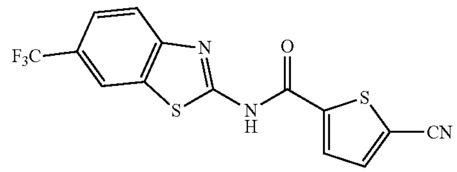 [SMILES: N#Cc1ccc(C(=O)Nc2nc3ccc(C(F)(F)F)cc3s2)s1]

A mixture of carboxylic acid 6c (153 mg, 1.0 mmol), TFFH (264 mg, 1.0 mmol), and CsF (230 mg, 1.5 mmol) in MeCN (3 mL) was stirred for 24 h at room temperature. To the mixture containing the in situ generated acid fluoride 7c was added a solution of TMS-amine 4c (145 mg, 0.67 mmol) in MeCN (3 mL). The resultant mixture was stirred at 50° C. for 48 h. It was then concentrated under reduced pressure and the solid obtained was silica-gel flash column chromatographed (100% EtOAc) to afford 8e as a white solid in 54% (127 mg, 0.36 mmol).

$^1$H NMR (400 MHz, DMSO-$d_6$): δ=13.67 (s, 1H), 8.53 (s, 1H), 8.27 (bs, 1H), 8.09 (d, J=3.8 Hz, 1H), 7.90 (bs, 1H), 7.79 (dd, J=8.3 Hz, 1H).

DEPT 135 $^{13}$C NMR (400 MHz, DMSO-$d_6$): δ=139.9, 131.1, 123.3, 120.2.

N-(4-chlorobenzo[d]thiazol-2-yl)-5-cyanothiophene-2-carboxamide (8f)

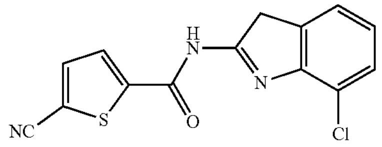 [SMILES: N#Cc1ccc(C(=O)NC2=Nc3c(Cl)cccc3C2)s1]

A mixture of carboxylic acid 6c (153 mg, 1.0 mmol), TFFH (264 mg, 1.0 mmol), and CsF (230 mg, 1.5 mmol) in MeCN (3 mL) was stirred for 24 h at room temperature. To the mixture containing the in situ generated acid fluoride 7c was added a solution of TMS-amine 4a (123 mg, 0.67 mmol) in MeCN (3 mL). The resultant mixture was stirred at 50° C. for 48 h. It was then concentrated under reduced pressure and the solid obtained was silica-gel flash column chromatographed using EtOAc to afford 8f as a yellow solid in 56% (120 mg, 0.375 mmol).

$^1$H NMR (400 MHz, DMSO-$d_6$): δ=13.62 (s, 1H), 8.40 (d, J=3.4 Hz, 1H), 8.09 (d, J=3.8 Hz, 1H), 8.02 (d, J=7.8 Hz, 1H), 7.57 (d, J=7.8 Hz, 1H), 7.35 (dd, J=7.6, 8.2 Hz, 1H).

$^{13}$C NMR (400 MHz, DMSO-$d_6$): δ=159.3, 159.1, 145.3, 143.6, 139.9, 133.2, 131.1, 126.4, 124.8, 124.6, 120.9, 114.1, 113.6.

DEPT 135 $^{13}$C NMR (400 MHz, DMSO-$d_6$): δ=139.9, 131.1, 126.4, 124.8, 120.9.

3. Preparation of amides 12a-c from 2-trifluoromethylthiazole-5-carboxylic acid The protocol used to prepare amides 8a-c was further used to access the 2-trifluoromethylthiazole-based amides 12a-c.

Scheme 3

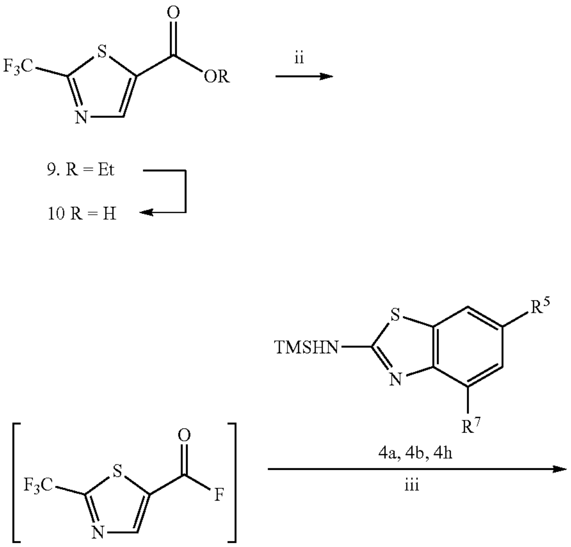

9. R = Et

10 R = H

11

-continued

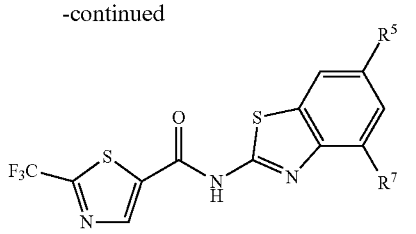

12a. $R_5$ = H, $R_7$ = Cl
12b. $R_5$ = $NO_2$, $R_7$ = H
12c. $R_5$ = $CF_3$, $R_7$ = H

Reagents and conditions: i) LiOH, THF/$H_2O$ (5-3), r.t., 2.5 h; ii) TFFH, CsF, MeCN, r.t., 12 h; iii) MeCN, TBAF (cat), 50° C., 12 h.

2-(trifluoromethyl)thiazole-5-carboxylic acid (10)

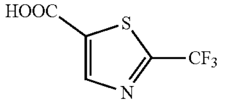 [SMILES: O=C(O)c1cnc(C(F)(F)F)s1]

A mixture of ethyl ester 9 (0.97 g, 4.31 mmol) and LiOH (220 mg, 9.17 mmol) in THF/$H_2O$ (5-3) (80 mL) was stirred for 2.5 h at room temperature. The mixture was then acidified to pH 1 using concentrated HCl. The mixture was extracted with $CH_2CL_2$, and the aqueous layer was washed with $CH_2CL_2$ (4×, 20 mL). The combined organic layers were dried over $Na_2SO_4$, filtrated, and concentrated to afford 10 as a yellow solid 93% (790 mg, 4.01 mmol).

$^1H$ NMR (400 MHz, DMSO-$d_6$): δ=8.61 (s, 1H).

$^{13}C$ NMR (400 MHz, DMSO-$d_6$): δ=161.1, 157.5 (q, J=40.0 Hz), 148.3, 135.6, 119.2 (q, J=272.6 Hz).

$^{19}F$ NMR (400 MHz, DMSO-$d_6$): δ=−60.66.

N-(4-chlorobenzo[d]thiazol-2-yl)-2-(trifluoromethyl)thiazole-5-carboxamide (12a)

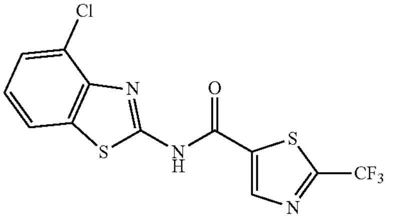 [SMILES: O=C(Nc1nc2c(Cl)cccc2s1)c1cnc(C(F)(F)F)s1]

A mixture of carboxylic acid 10 (300 mg, 1.5 mmol), TFFH (400 mg, 1.5 mmol), and CsF (340 mg, 2.25 mmol) in MeCN (8 mL) was stirred for 12 h at room temperature. To the mixture containing the in situ generated acid fluoride 11 was added a solution of TMS-amine 4a (1 mmol) in MeCN (8 mL). The resultant mixture was stirred at 50° C. for 12 h. It was then concentrated under reduced pressure and the solid obtained was silica-gel flash column chromatographed (Hex/EtOAc 7:3) to afford 12a as a white solid in 58% (210 mg, 0.58 mmol).

$^1H$ NMR (400 MHz, DMSO-$d_6$): δ=13.84 (s, 1H), 9.10 (s, 1H), 8.03 (d, J=7.9 Hz, 1H), 7.58 (d, J=7.7 Hz, 1H), 7.36 (t, J=7.9 Hz, 1H).

$^{13}C$ NMR (400 MHz, DMSO-$d_6$): δ=159.0, 158.6, 158.0 (q, J=40.0 Hz), 146.5, 145.3, 137.9, 133.2, 126.5, 125.0, 124.6, 121.0, 119.2 (q, J=273.3 Hz).

DEPT 135 $^{13}C$ NMR (400 MHz, DMSO-$d_6$): δ=146.5, 126.5, 125.0, 121.1.

$^{19}F$ NMR (400 MHz, DMSO-$d_6$): δ=−60.57.

N-(6-nitrobenzo[d]thiazol-2-yl)-2-(trifluoromethyl)thiazole-5-carboxamide (12b)

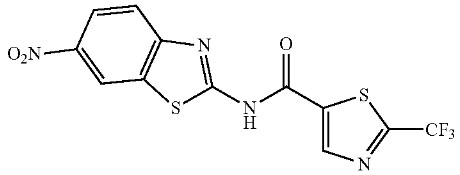 [SMILES: O=C(Nc1nc2ccc([N+](=O)[O-])cc2s1)c1cnc(C(F)(F)F)s1]

A mixture of carboxylic acid 10 (267 mg, 1.35 mmol), TFFH (362 mg, 1.37 mmol), and CsF (500 mg, 3.31 mmol) in MeCN (6 mL) was stirred for 27 h at room temperature. To the mixture containing the in situ generated acid fluoride was added a solution of TMS-amine 4c (0.85 mmol) in MeCN (6 mL). The resultant mixture was stirred at 50° C. for 48 h. It was then concentrated under reduced pressure to afford 12b in pure form as a yellow solid in 119% (380 mg, 1.01 mmol).

$^1H$ NMR (400 MHz, DMSO-$d_6$): δ=11.84 (s, 1H), 8.67 (d, J=2.5 Hz, 1H), 8.41 (s, 1H), 8.11 (dd, J=2.5, 8.9 Hz, 1H), 7.55 (d, J=8.9 Hz, 1H).

$^{19}F$ NMR (400 MHz, DMSO-$d_6$): δ=−60.24

2-(trifluoromethyl)-N-(6-(trifluoromethyl)benzo[d]thiazol-2-yl)thiazole-5-carboxamide (12c)

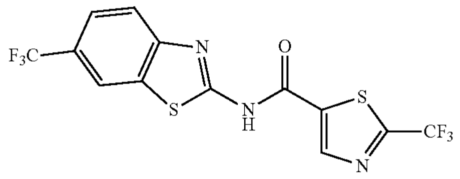 [SMILES: O=C(Nc1nc2ccc(C(F)(F)F)cc2s1)c1cnc(C(F)(F)F)s1]

A mixture of carboxylic acid 10 (250 mg, 1.27 mmol), TFFH (340 mg, 1.28 mmol), and CsF (600 mg, 3.95 mmol) in MeCN (6 mL) was stirred for 12 h at room temperature. To the mixture containing the in situ generated acid fluoride 11 was added a solution of TMS-amine 4h (0.85 mmol) in MeCN (6 mL). The resultant mixture was stirred at 50° C. for 12 h. It was then concentrated under reduced pressure and the solid obtained was silica-gel flash column chromatographed (100% EtOAc) and then recrystallized in EtOAC to afford 12c as a white solid in 55% (184 mg, 0.46 mmol).

$^1H$ NMR (400 MHz, DMSO-$d_6$): δ=13.87 (s, 1H), 8.95 (s, 1H), 8.52 (s, 1H), 7.89 (d, J=8.2 Hz, 1H), 7.78 (d, J=8.7 Hz, 1H).

$^{13}C$ NMR (400 MHz, DMSO-$d_6$): δ=157.7 (q, J=40.1 Hz), 146.5, 138.7, 131.1, 124.5 (q, J=272.7 Hz), 124.2 (q, J=32.1 Hz), 123.5 (2×CH), 120.3, 119.2 (q, J=271.9 Hz), (3 carbons are missing).

DEPT 135 $^{13}C$ NMR (400 MHz, DMSO-$d_6$): δ=146.5, 123.5, 120-3.s $^{19}F$ NMR (400 MHz, DMSO-$d_6$): δ=−60.59, −59.63.

4. Preparation of N-(6-aminobenzo[d]thiazol-2-yl)-2-(trifluoromethyl)thiazole-5-carboxamide (12d) and its conversion to N-(6-azidobenzo[d]thiazol-2-yl)-2-(trifluoromethyl)thiazole-5-carboxamide (12e)

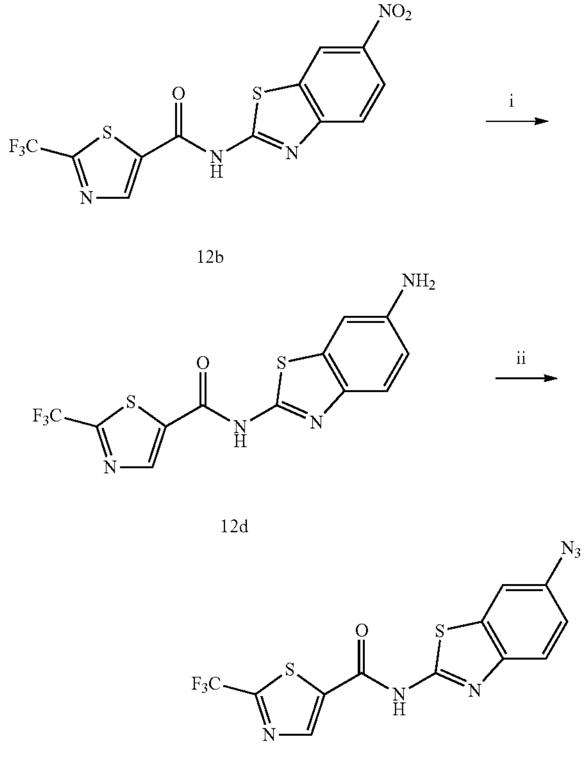

12b

12d

12e

Reaction Scheme: Reagents and conditions: i) $SnCl_2$, $SnCl_4$, HCl, r.t., 4 h; ii) $NaNO_2$, HCl, $NaN_3$, $H_2O$, 0° C., 2 h, r.t., 1 h N-(6-aminobenzo[d]thiazol-2-yl)-2-(trifluoromethyl)thiazole-5-carboxamide (12d)

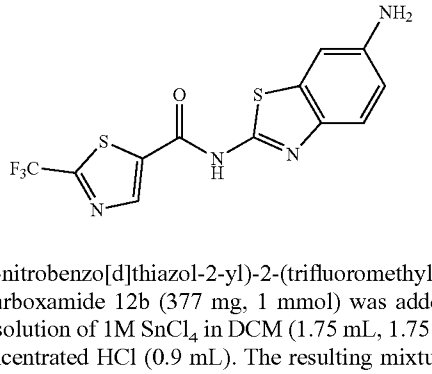

N-(6-nitrobenzo[d]thiazol-2-yl)-2-(trifluoromethyl)thiazole-5-carboxamide 12b (377 mg, 1 mmol) was added to a cooled solution of 1M $SnCl_4$ in DCM (1.75 mL, 1.75 mmol) and concentrated HCl (0.9 mL). The resulting mixture was stirred at 0° C. for 10 minutes before dropwise addition (over 30 minutes) of $SnCl_2$ (682 mg, 3.6 mmol in 0.5 mL concentrated HCl) at 0° C. The resulting mixture was stirred for 30 minutes at 0° C. and then 45 minutes at room temperature. The reaction mixture was then diluted with $Et_2O$ and filtered. The isolated product was passed through a short silica gel column and 100% MeOH was used as eluent. After concentrating the isolated product, it was dissolved in EtOAc and then washed with $H_2O$ to afford 12d in 28% yield (95 mg, 0.28 mmol)

$^1H$ NMR (400 MHz, DMSO-d6): δ=8.97 (bs, 1H), 8.03 (s, 1H), 7.83 (bs, 1H), 7.46 (dd, J=2.1, 8.6 Hz, 1H)

$^{19}F$ NMR (400 MHz, DMSO-$d_6$): δ=−60.44

N-(6-azidobenzo[d]thiazol-2-yl)-2-(trifluoromethyl)thiazole-5-carboxamide (12e)

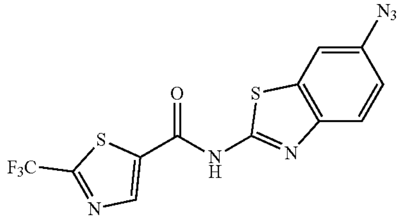 [SMILES: [N-]=[N+]=Nc1ccc2nc(NC(=O)c3cnc(C(F)(F)F)s3)sc2c1]

N-(6-aminobenzo[d]thiazol-2-yl)-2-(trifluoromethyl)thiazole-5-carboxamide (12d) (75 mg, 0.20 mmol) dissolved in 2.36N hydrochloric acid (0.7 mL) and cooled to 0° C. in an ice bath. To this stirred mixture, $NaNO_2$ (16 mg, 40 mmol) in 1.1 mL of water was added and stirred for 30 minutes at room temperature. After that, the reaction mixture was gradually neutralized to pH 6.0-7.0 with sodium acetate. Then, an aqueous solution of sodium azide (0.26 mmol in 1.1 mL of water) was gradually added and the mixture was stirred at −5° C. for 30 minutes. The reaction mixture was then diluted with EtOAc (4.5 mL) and extracted with 3×5 mL of EtOAc. The combined organic layers were dried over sodium sulfate and concentrated under reduced pressure. The isolated crude product was purified by column chromatography (100% EtOAc) to afford 12e in 3% yield (3 mg, 0.008 mmol).

$^1H$ NMR (400 MHz, DMSO-$d_6$): δ=13.68 (s, 1H), 8.94 (bs, 1H), 7.89 (s, 1H), 7.75 (bs, 1H), 7.23 (dd, J=2.5, 8.6 Hz, 1H)

$^{19}F$ NMR (400 MHz, DMSO-$d_6$): δ=−60.51

EXAMPLES

Example 1—Construction and Evaluation of a Library of Compounds Based on the 5350150 Compound Selected examples of molecules fitting the general formula are:

5a

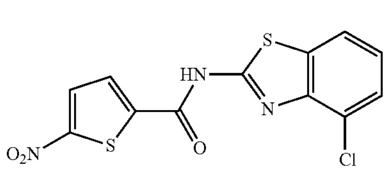

GPS389

-continued
5k
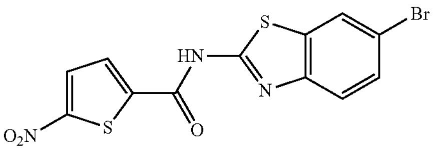
GPS473
12c
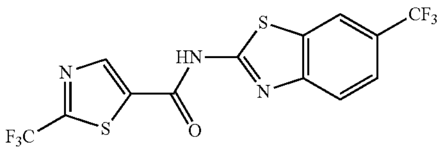
GPS491
5b
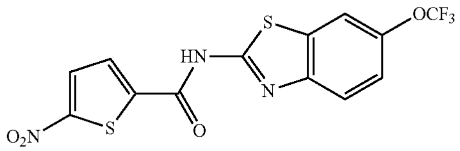
GPS426
5l
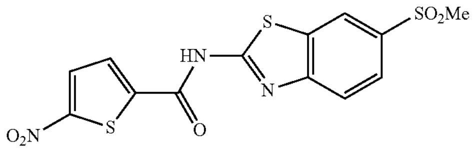
GPS427
13a
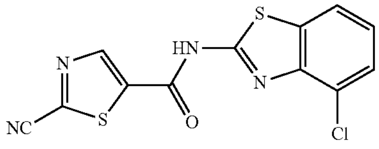
GPS520
5c
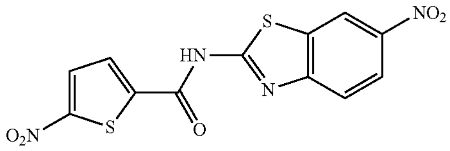
GPS428
8a
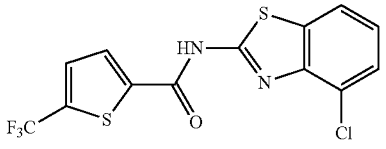
GPS440
-continued
13b
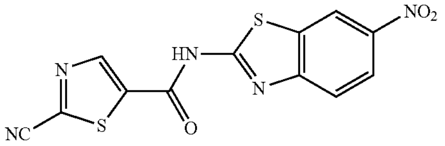
GPS521
5d
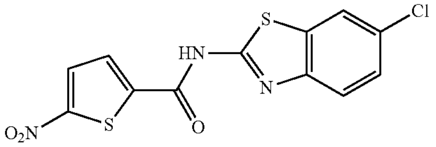
GPS475
8b
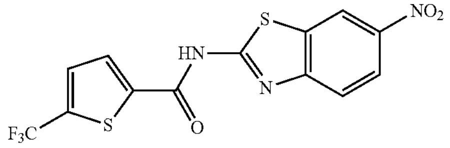
GPS483
13c
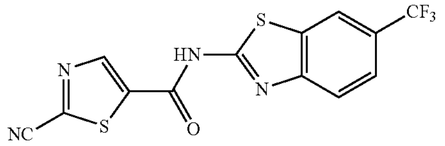
GPS522
5e
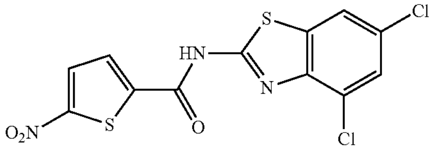
GPS476
8c
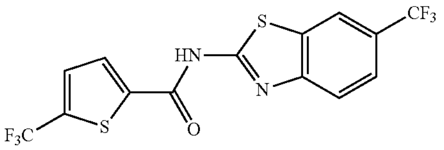
GPS 485
13d
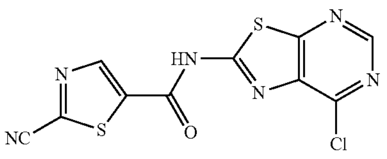
GPS527

-continued

5f

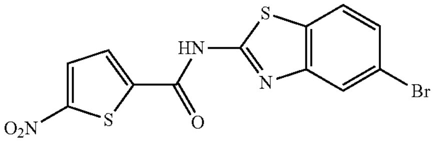

GPS478

8d

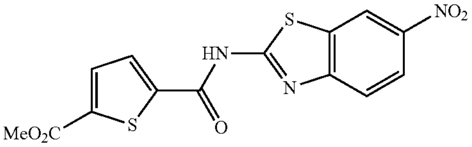

GPS472

12e

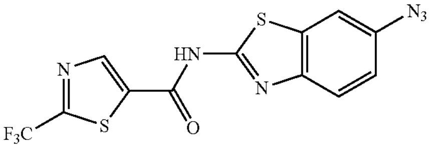

GPS519

5g

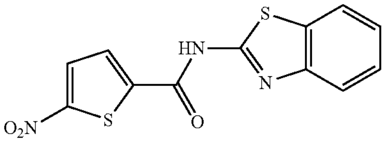

GPS445

8e

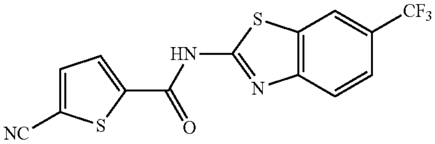

GPS504

12f

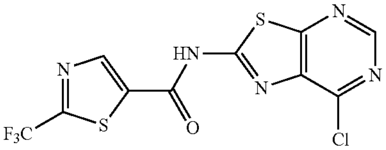

GPS526

5h

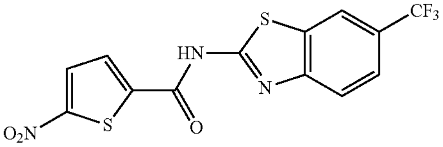

GPS484

8f

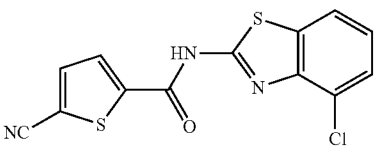

GPS505

-continued

13e

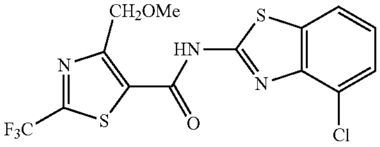

GPS523

5i

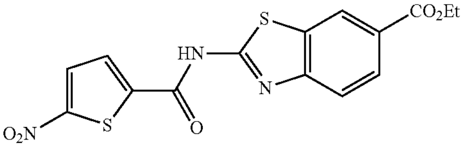

GPS477

12a

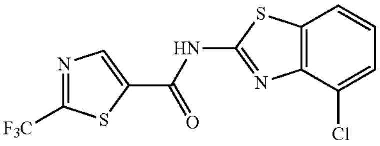

GPS488

13f

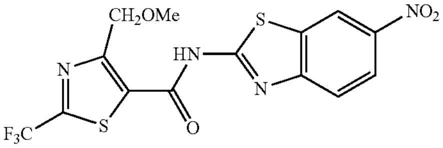

GPS524

5j

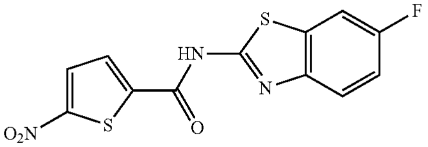

GPS474

12b

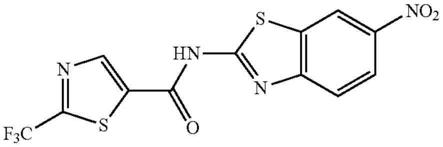

GPS506

13g

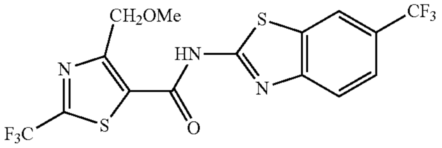

GPS525

To determine whether exchanging the central double bond by an amide in 5350150 would have a negative influence on biological activity, and if it does, what alternative motif on the right side would recover activity, an exploratory library of 5350150-amide analogues was prepared using the acyl fluoride—TMS amine condensation protocol.

A preliminary evaluation of the anti-HIV activity of this library was carried out using a cell-based screen as described previously (Cheung, Horhant et al. 2016). Briefly, CEM- GXR cells are an immortalized CD4+ T-lymphocyte line that expresses GFP due to the activation of the tat-dependent promoter upon HIV-1 infection (Brockman, Tanzi et al. 2006). The reporter CEM-GXR cells were infected by co-culture with one percent HIV-1NL4-3 infected (GFP positive) cells at the start of the assay (day 0). Individual compounds from the library was added in DMSO at varying concentrations to the culture in each microplate well immediately after the inoculation by infected cells. The final library compound concentration ranged from 1.25-10 μM and the final DMSO concentration was less than 0.1%. The percent of infected cells in the culture was determined by flow cytometry on day 3 using GFP expression as a readout. The results determined for a selection of the series of compounds is reported in FIGS. 1A and 1B.

Figure 1B:
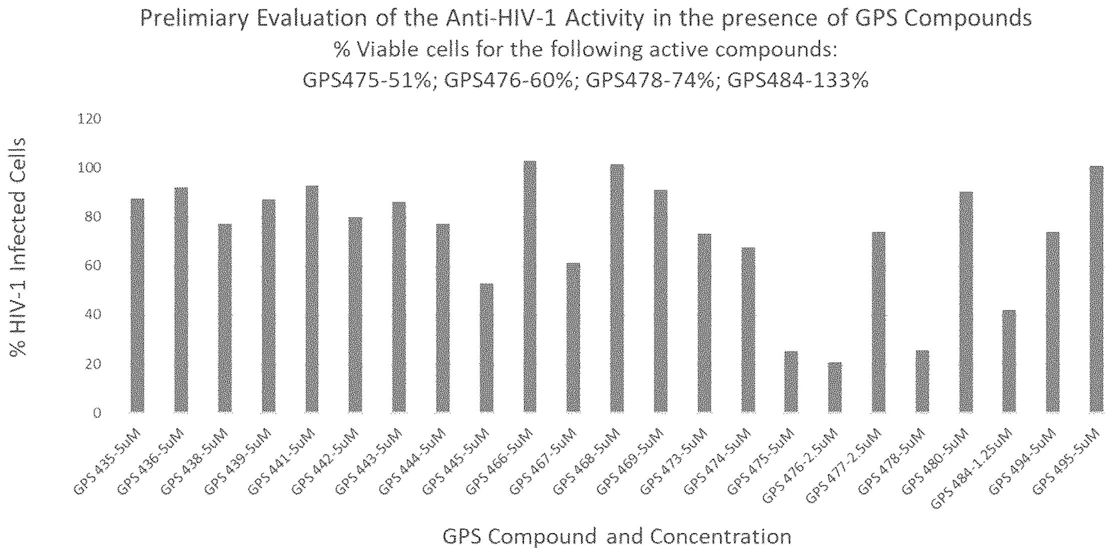
Figure 2A:
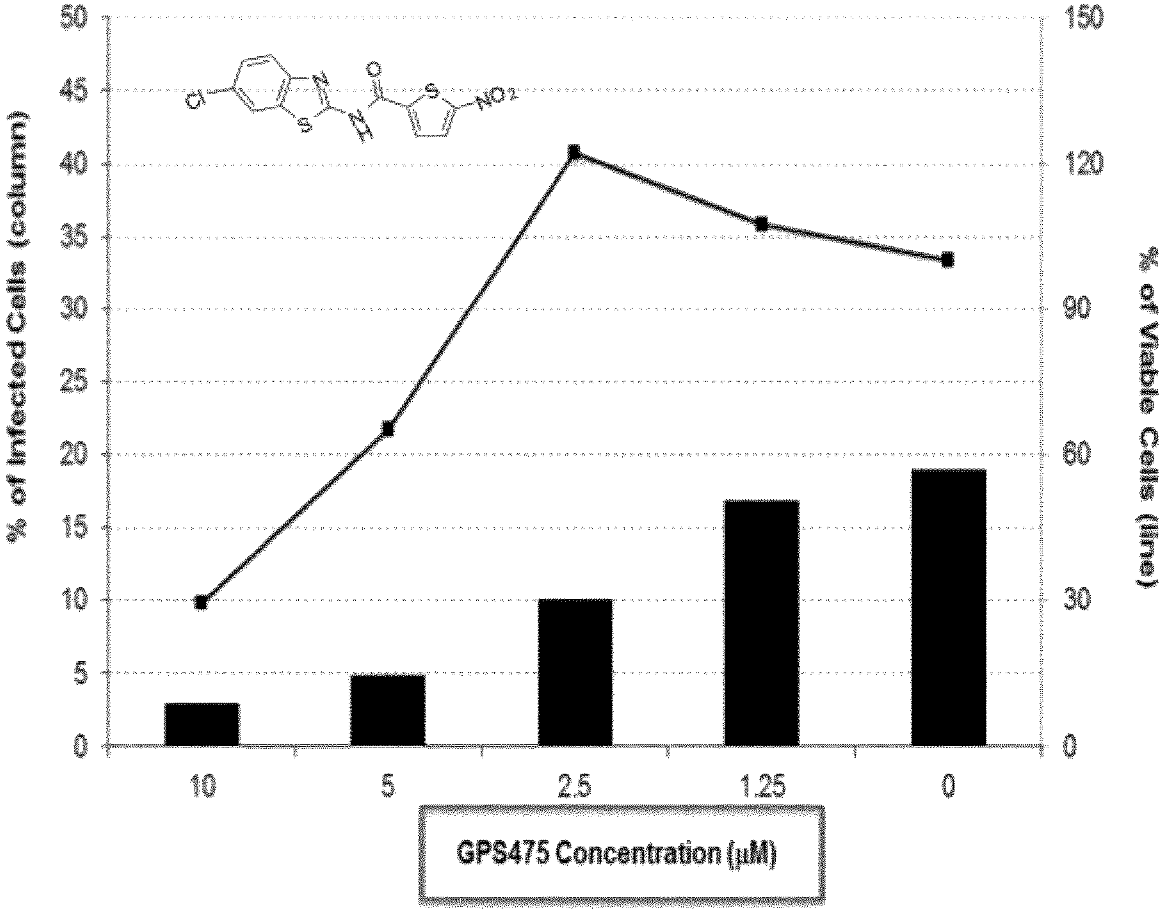
FIG. 2: shows the anti-HIV activity (bar graph) and the cytotoxicity against the CEM-GXR cells (line graph) for a GPS475 (5d) (FIG. 2A), GPS477 (5i) (FIG. 2B), GPS484 (5h) (FIG. 2C), GPS 389 (5a) (FIG. 2D), GPS428 (5c) (FIG. 2E), GPS472 (8d) (FIG. 2F), GPS504 (8e) (FIG. 2G) and GPS505 (80 (FIG. 2H) at increasing concentrations against HIV wild-type subtype B (NL4-3 WT and HIV-1BaL).
Figure 2B:
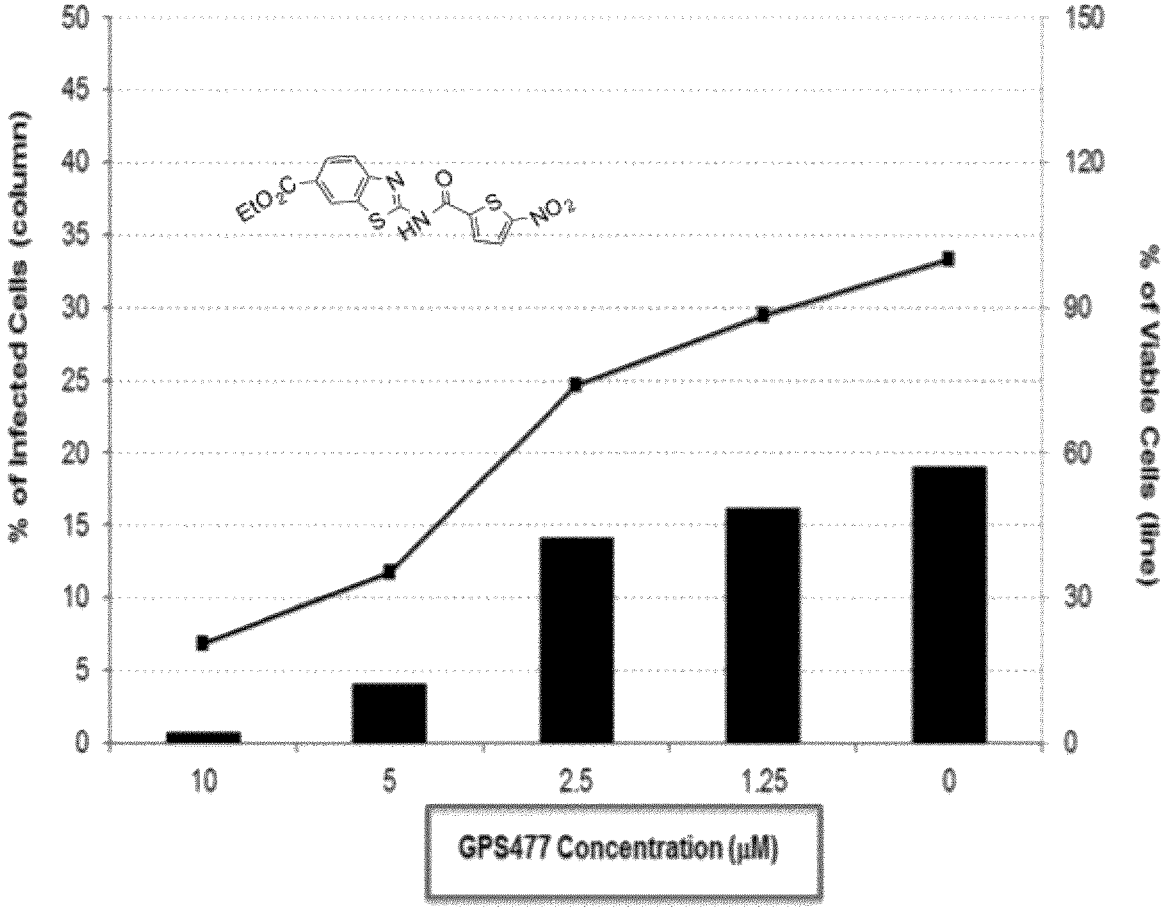
Figure 2C:
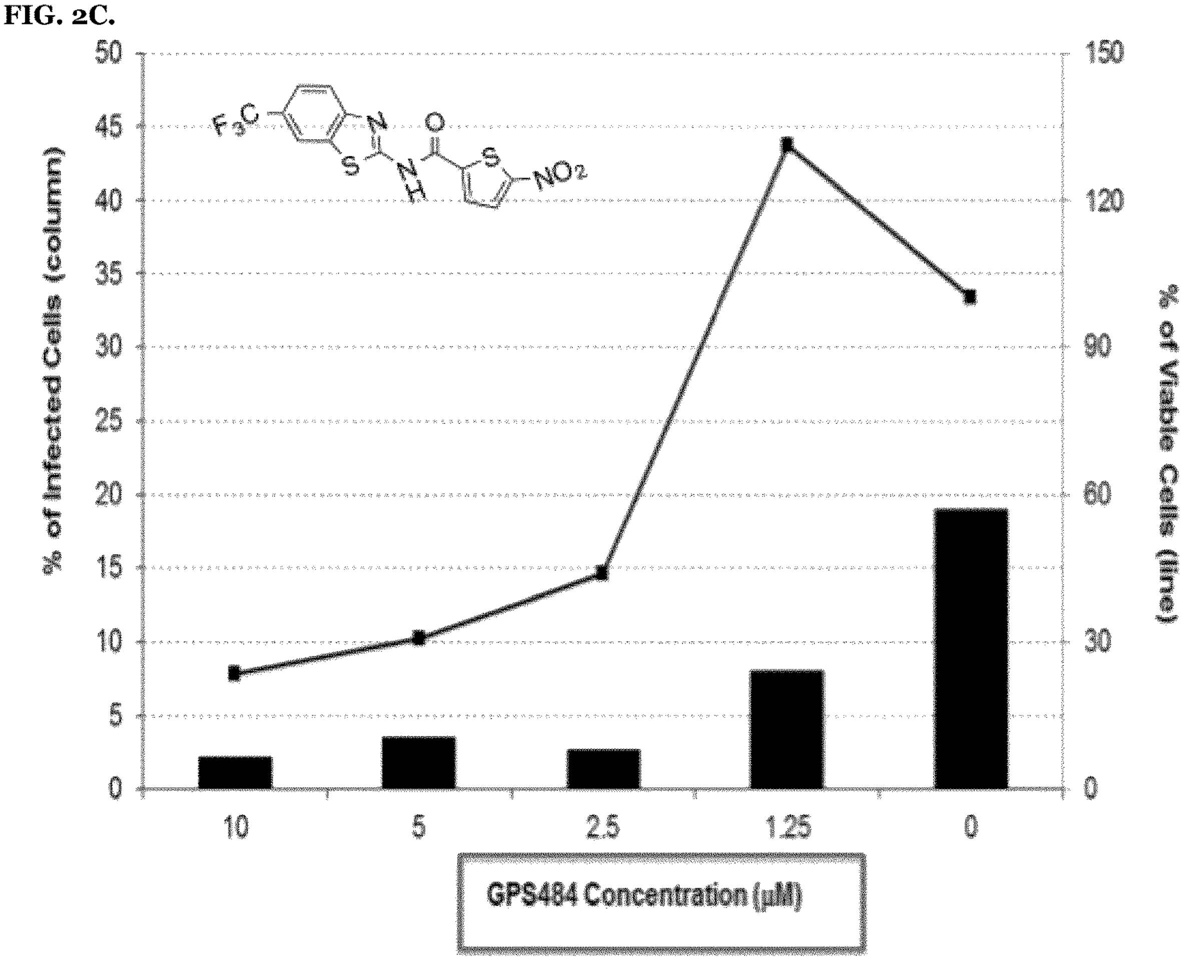
Figure 2D:
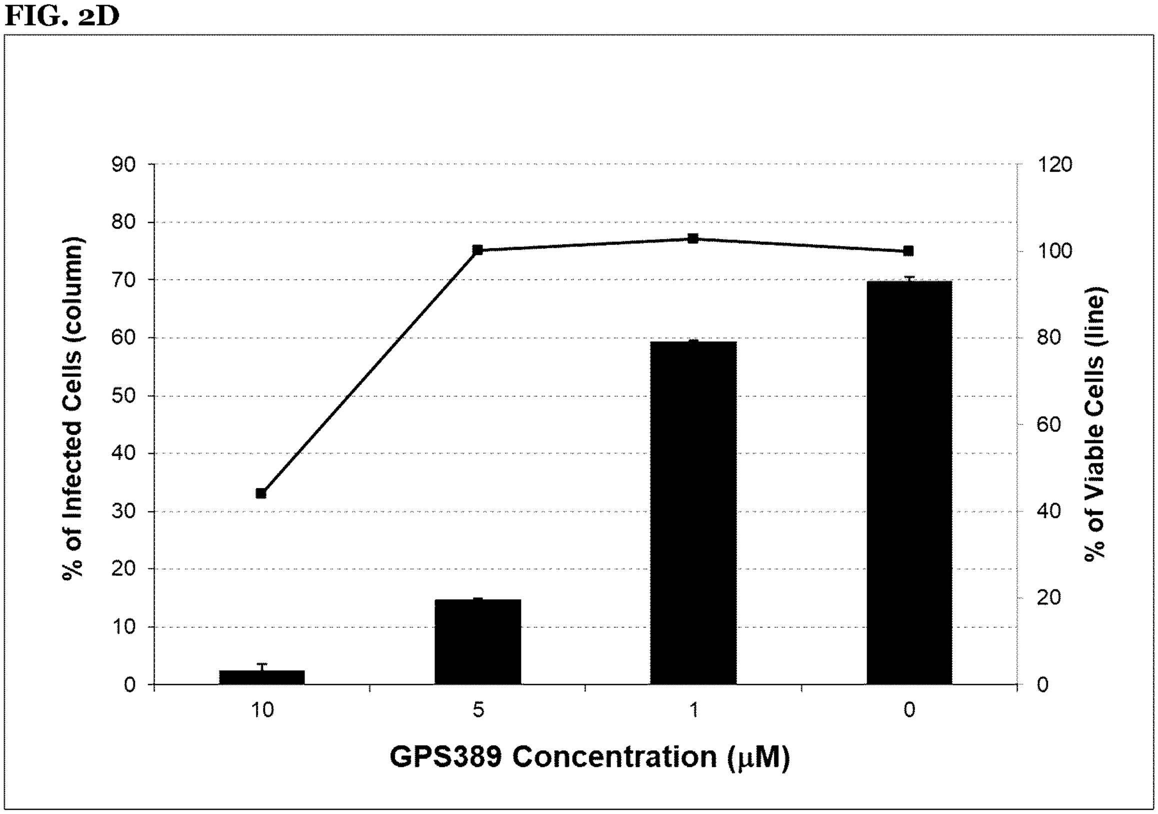
Figure 2E:
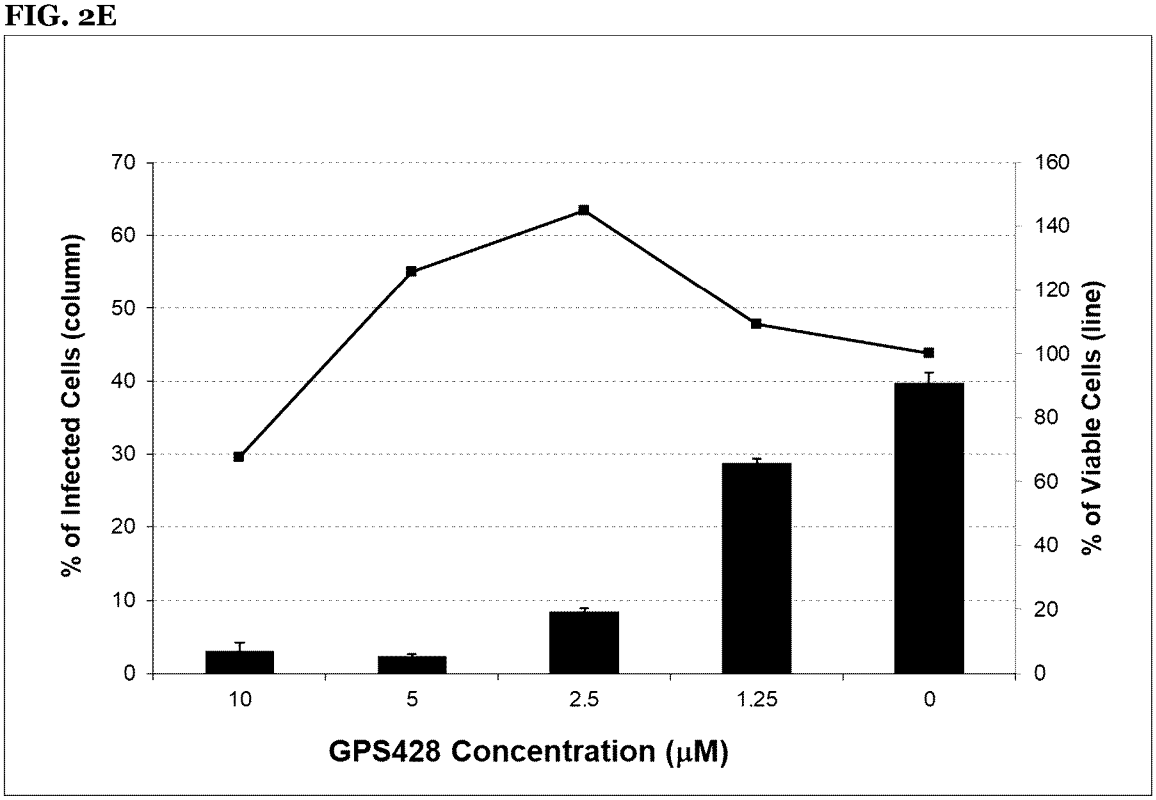
Figure 2F:
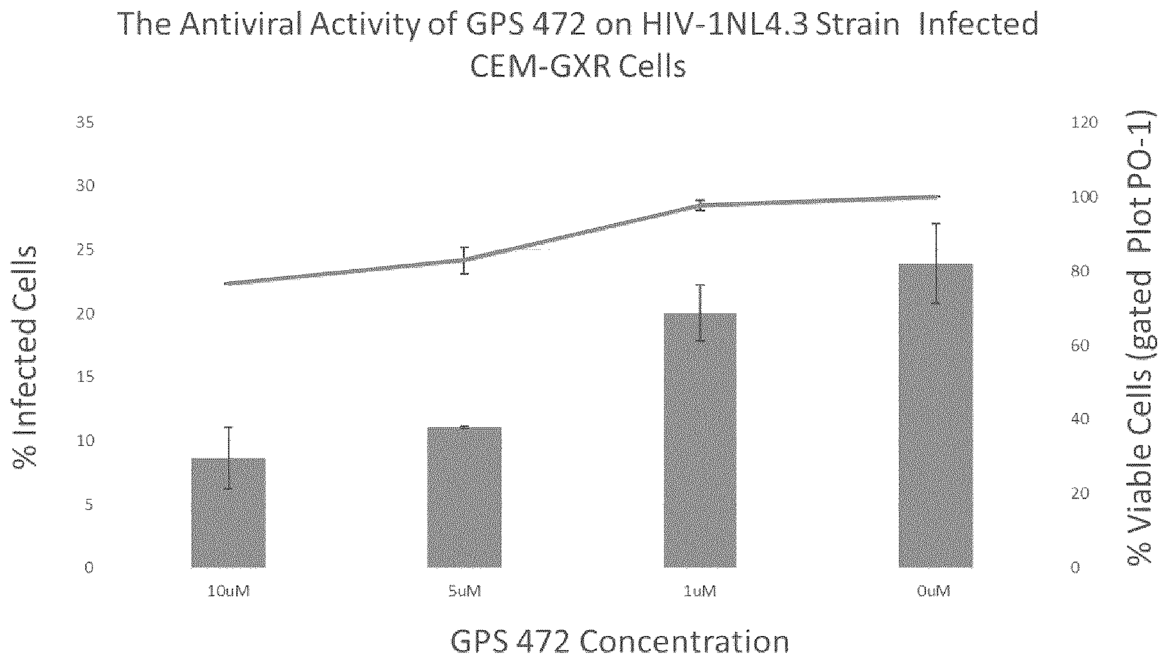
Figure 2G:
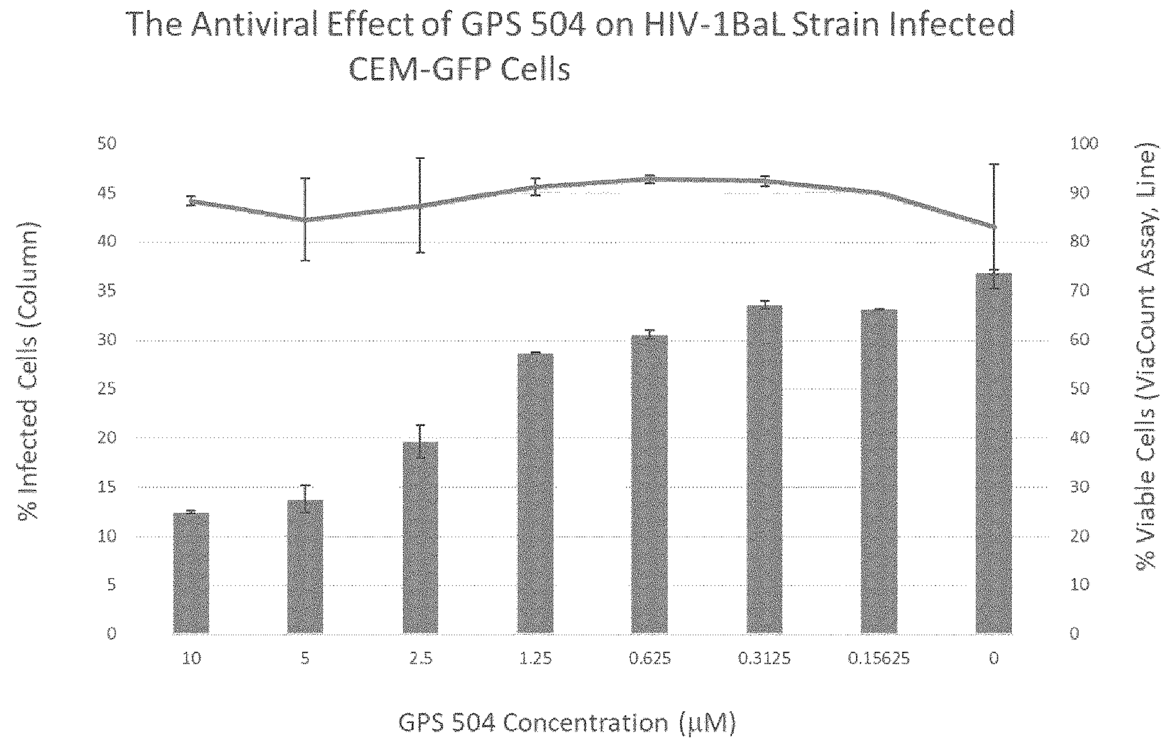
Figure 2G:
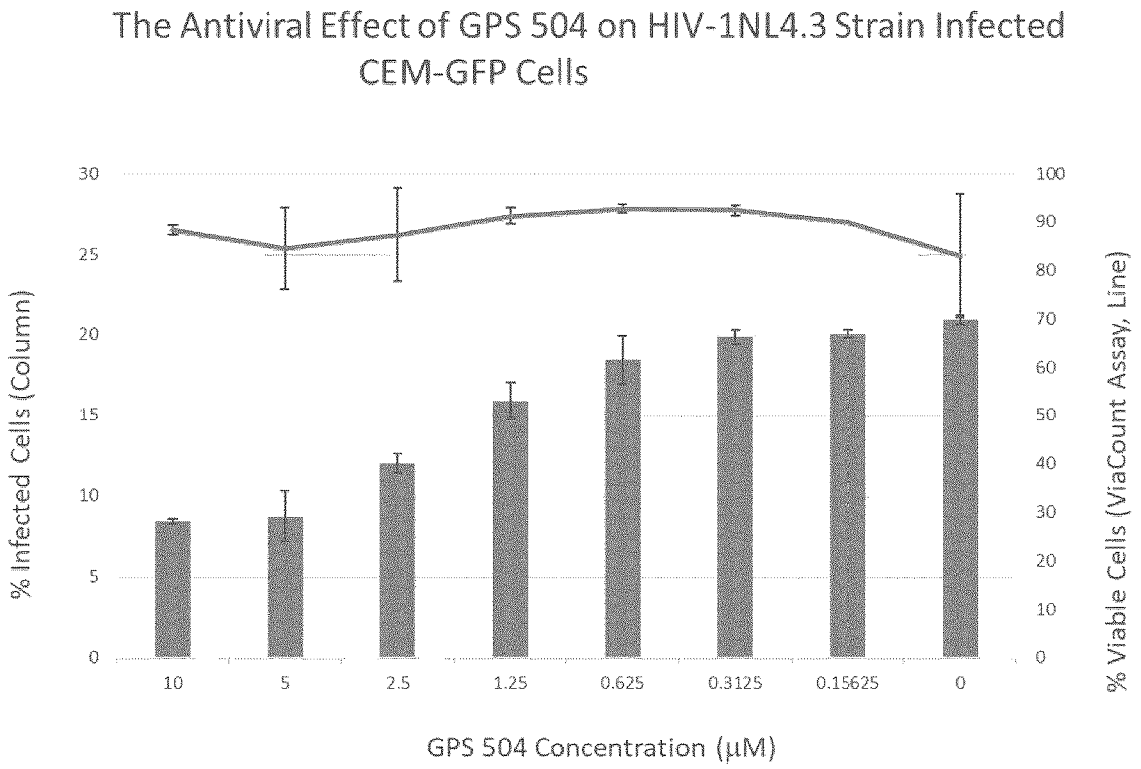
Figure 2H:
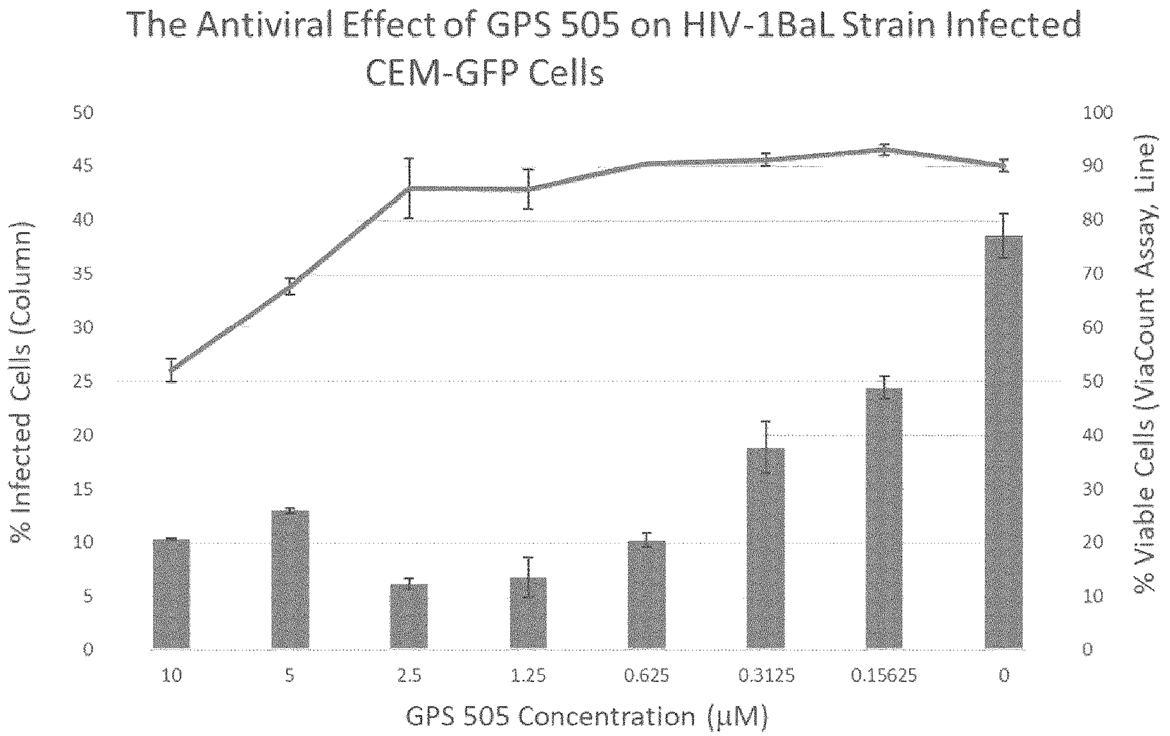
Figure 2H:
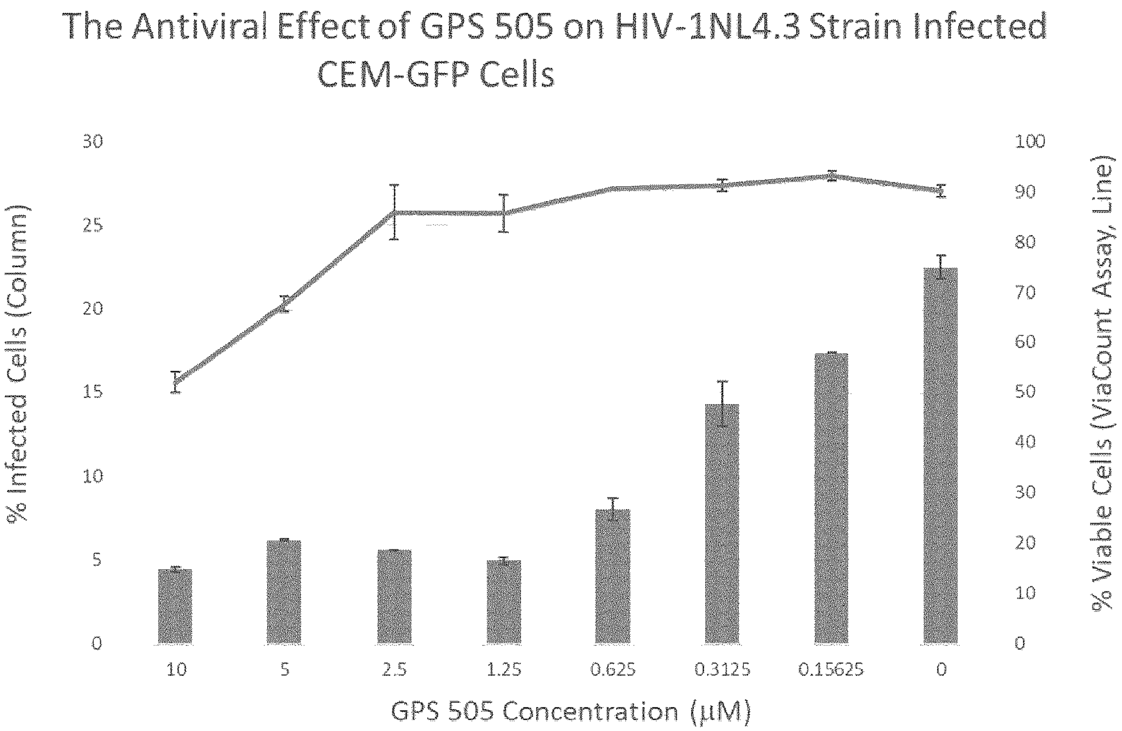

As shown in FIGS. 1A and 1B, anti-HIV activity was found for twelve 5350150 amide analogues bearing a functionalized benzothiazole-2-amine motif on the "right side". Eight of these compounds 5a (GPS389), 5b (GPS426), 5c (GPS428), 5d (GPS475), 5e (GPS476), 5f (GPS478), and 5h (GPS484), showed significant activity in the primary library screen. The other four benzothiazole-based compounds: the unsubstituted benzothiazole 5g (GPS445), the 6-fluoro compound 5j (GPS474), the 6-bromo compound 5k (GPS473), and the 6-methylsulfone 5i (GPS477) showed moderate to weak anti-HIV activity.

The potential cytotoxic effect of the molecules on CEM-GXR cells viability was determined by the Guava ViaCount assay. This assay differentially stains viable and nonviable cells based on their permeability to the DNA-binding dyes and uses the forward scatter (FSC) properties to distinguish free nuclei and cellular debris from intact cells to quantify cell count. CEM-GXR cells were incubated with compound at concentrations ranging between 0.5 and 100 μM for 24 h.

The 6-$OCF_3$ compounds 5b (GPS426), 5e (GPS476) and 5f (GPS478) showed toxicity at 5 μM in the preliminary screen (data not shown), whereas it was determined that for the active benzisothiazole compounds 5a (GPS389), 5c (GPS428), and 5h (GPS484) and the other less active compounds, toxicity followed activity and the selectivity index (ratio of toxicity/activity) was low (data not shown). FIG. 2 shows the anti-HIV activity (bar graph) and the cytotoxicity against the CEM-GXR cells (line graph) for a selection of compounds from the library of 5350150 amide analogues with GPS475 (5d) (FIG. 2A), GPS477 (5i) (FIG. 2B), GPS484 (5h) (FIG. 2C), GPS389 (5a) (FIG. 2D), GPS428 (5c) (FIG. 2E), GPS 472 (8d) (FIG. 2F), GPS504 (8e) (FIG. 2G) and GPS505 (8f) (FIG. 2H) as active compounds representative of benzisothiazole compounds.

Structural changes that were studied to improve the activity/toxicity (Selectivity Index) ratio of the thiophene-based 5350150 amide analogues involved replacing the nitro substituent on the thiophene ring by R1=H, Me, $CF_3$, $CO_2H$, $CO_2Me$, and CN. The thiophene compounds where the C-2 substituent corresponded to H, Me, and $CF_3$ were prepared from commercial thiophene-2-carboxylic acid, 5-methylthiophene-2-carboxylic acid and 5-trifluoromethylthiophene carboxylic acid, respectively. The 5350150 amide analogue 8d bearing a methyl ester function at C-2 of the thiophene ring were prepared by converting thiophene-2,5-dicarboxylic acid 16 to its dimethyl ester derivative 17, followed by hydrolysis to the monoester acid intermediate 18 (Scheme 5 below). To access compounds 8e and 8f, from the C-2 cyano substituted thiophene-2-carboxylic acid 20, monoester 18 was converted to amide 19 through reaction with ammonia under peptide coupling conditions, followed by $CONH_2 \rightarrow CN$ conversion through reaction with $POCl_3$, and subsequent hydrolysis of the ester function.

The C-2 $CF_3$ substituted thiophene analogues 8a (GPS440) (4-Cl benzothiazole motif), 8b (GPS483) (6-nitro benzothiazole unit) and 8c (GPS485) (6-trifluoromethyl benzothiazole motif) were the most active. However, thiophene analogue 8b (GPS483) and 8c (GPS485) exhibited toxicity at low micromolar concentrations.

Scheme 5

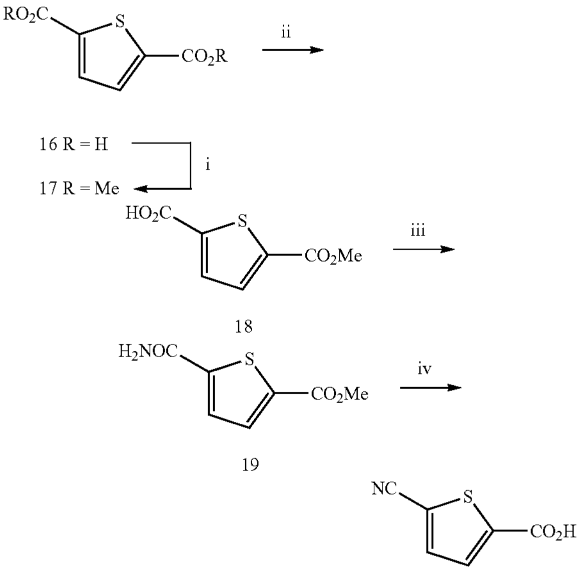

16 R = H

17 R = Me

18

19

20

Reagents and conditions: i)) MeOH-HCl (satd); ii) NaOHaq ( ).5 equiv); iii $NH_3$, DMF, EDC; $POCl_3$, then NaOHaq.

Studies to replace the thiophene ring in the 5350150 amide analogues 8a-c by a thiazole motif and the C-2 $NO_2$ group by R1=$CF_3$ and CN led to preparation of compounds 12a-f and 13a-d, respectively (Example 1). The C-2 $CF_3$ substituted thiazole compounds 12a (GPS488) (4-Cl benzothiazole unit), 12b (GPS506) (6-$NO_2$ substituent), 12c (GPS491) (6-$CF_3$ substituent) and 12e (GPS519) (6-azide substituent) were the most active 5350150-amide analogues in this series.

Within the thiazole series, a further modification was studied involving introduction of a pending $CH_2OMe$ side chain onto C-4 of the 2-trifluoromethylthiazole ring, as in compounds 15a-c (Example 1). The requisite thiazole precursor to these compounds is commercially available, and alternatively can be prepared according to P. Peverallo et al. Eur. Pat. Applic. 3290417 (2018).

Based upon their cell viability profiles the two compounds 12a (GPS488) and 12c (GPS491) were selected as our advanced lead compounds for more detailed biology studies.

Example 2: Calculation of $EC_{50}$ Versus Wild-Type HIV Strains in T Cell Lines and PBMCs Given that the antiviral activity of anti-HIV drugs can vary significantly due to the genetic variation of HIV-1 subtypes and its coreceptor usage, compounds GPS488 (12a) and GPS491 (12c) were evaluated in an anti-HIV screen assay of viral spread using different HIV-1 subtypes and tropisms. In the experiment, the culture contained serial dilutions of molecules GPS488 (12a) and GPS491 (12c) in final concentrations between 100 nM and 10 μM, and the half maximal effective concentration ($EC_{50}$) values were calculated by nonlinear regression with GraphPad Prism™ software. As shown in the FIGS. 3A and 3B, the compound GPS488 (12a) and GPS491 (12c) showed a dose-dependent ability to inhibit viral replication and cell to cell spread for HIV-1IIIB (subtype B, X4-tropic), and HIV-1 97USSN54 (subtype A, R5-tropic), with of $EC_{50}$ of 1290 nM (WT—Subtype B) and 955 nM (WT Subtype A) for compound GPS488 (12a) (FIG. 3B) and an $EC_{50}$ of 248 nM (WT—Subtype B) and 176 nM (WT Subtype A) for compound GPS491 (12c) (FIG. 3A). Note that compound GPS491 (12c) was 4.5 times more potent than GPS488 (12a) in these assays. To validate these $EC_{50}$ values, the anti-HIV drug, emtricitabine (FTC) was included in the anti-HIV assay as a positive control. Serial dilutions of FTC in final concentrations between 1 nM and 10 μM were tested, and $EC_{50}$ values of 33.69 nM (WT Subtype B) and 26.28 nM (WT Subtype A) were determined.

Figure 4:
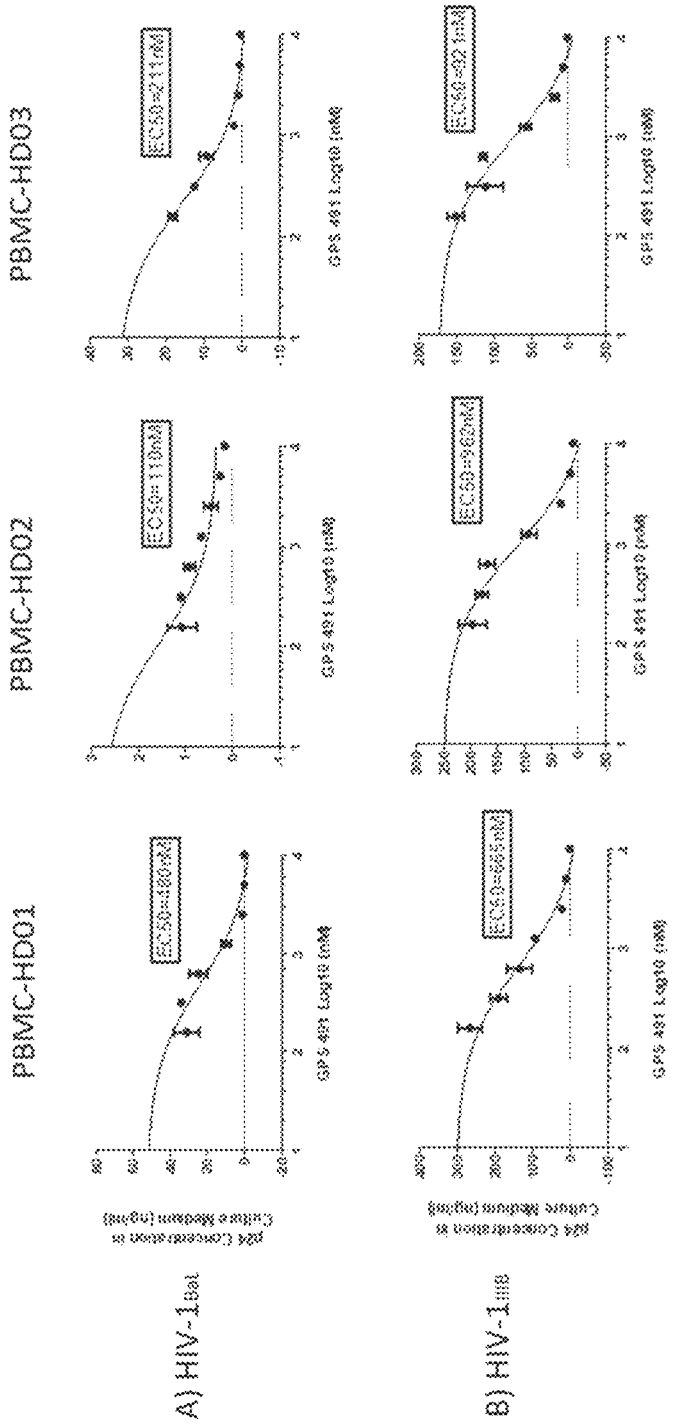
FIG. 4: (A) The Antiviral Effect of GPS491 (12c) at various concentrations against HIV-1BaL virus for three separate PBMC donors. (B) The Antiviral Effect of GPS491 (12c) at various concentrations against HIV-1IIIB virus for three separate PBMC donors. The level of viral infection was determined by the concentration of the p24 viral protein in the cell culture media as on 11 days post-infection. The three PBMC donor cells were labelled as PBMC-HD01, HD02 and HD03.
Figure 5:
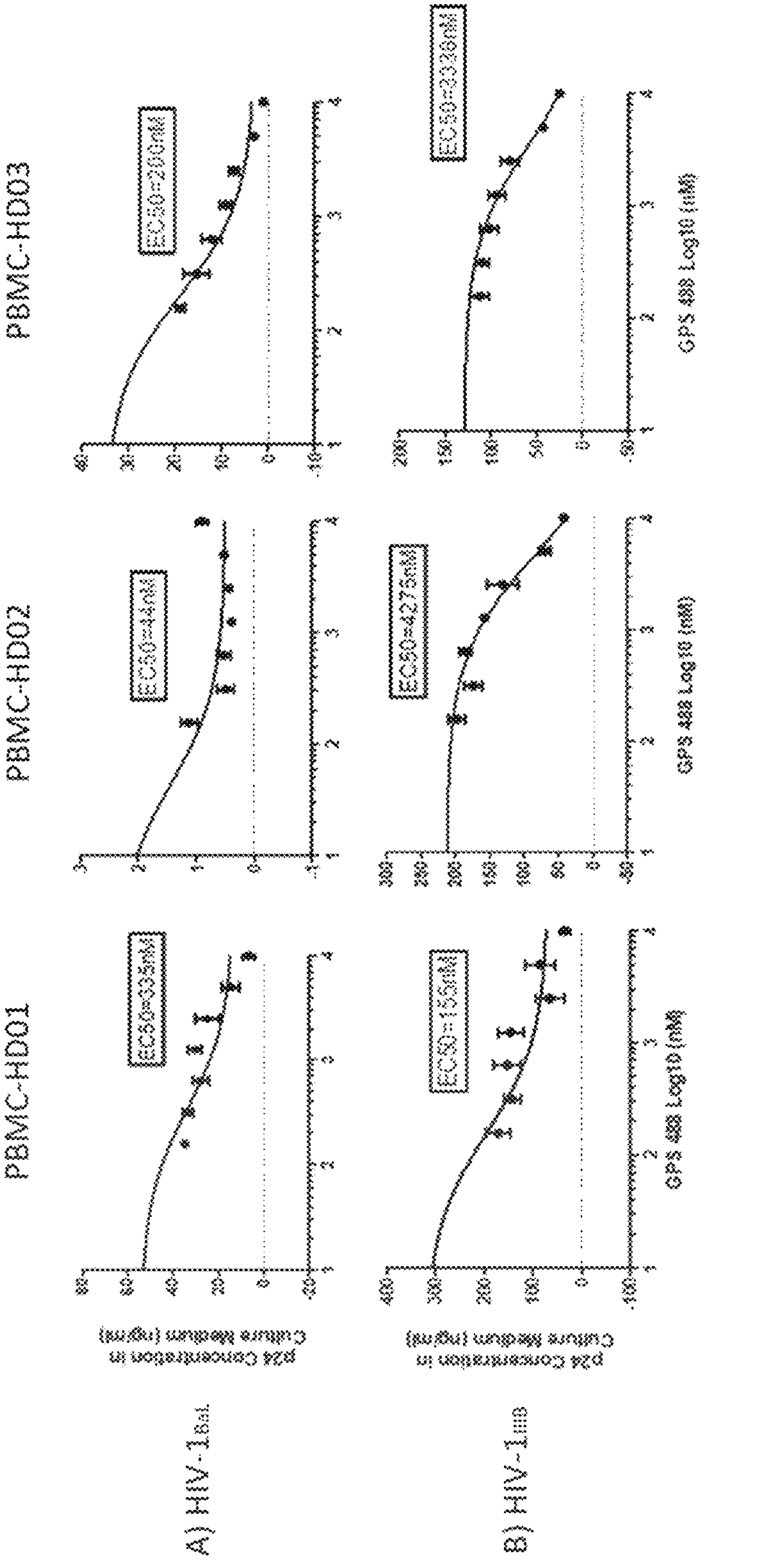
FIG. 5: (A) The Antiviral Effect of GPS488 (12a) at various concentrations against HIV-1BaL virus for three separate PBMC donors. (B) The Antiviral Effect of GPS488 (12a) at various concentrations against HIV-1IIIB virus for three separate PBMC donors. The level of viral infection was determined by the concentration of the p24 viral protein in the cell culture media as on 11 days post-infection. The three PBMC donor cells were labelled as PBMC-HD01, HD02 and HD03.
Figure 6:
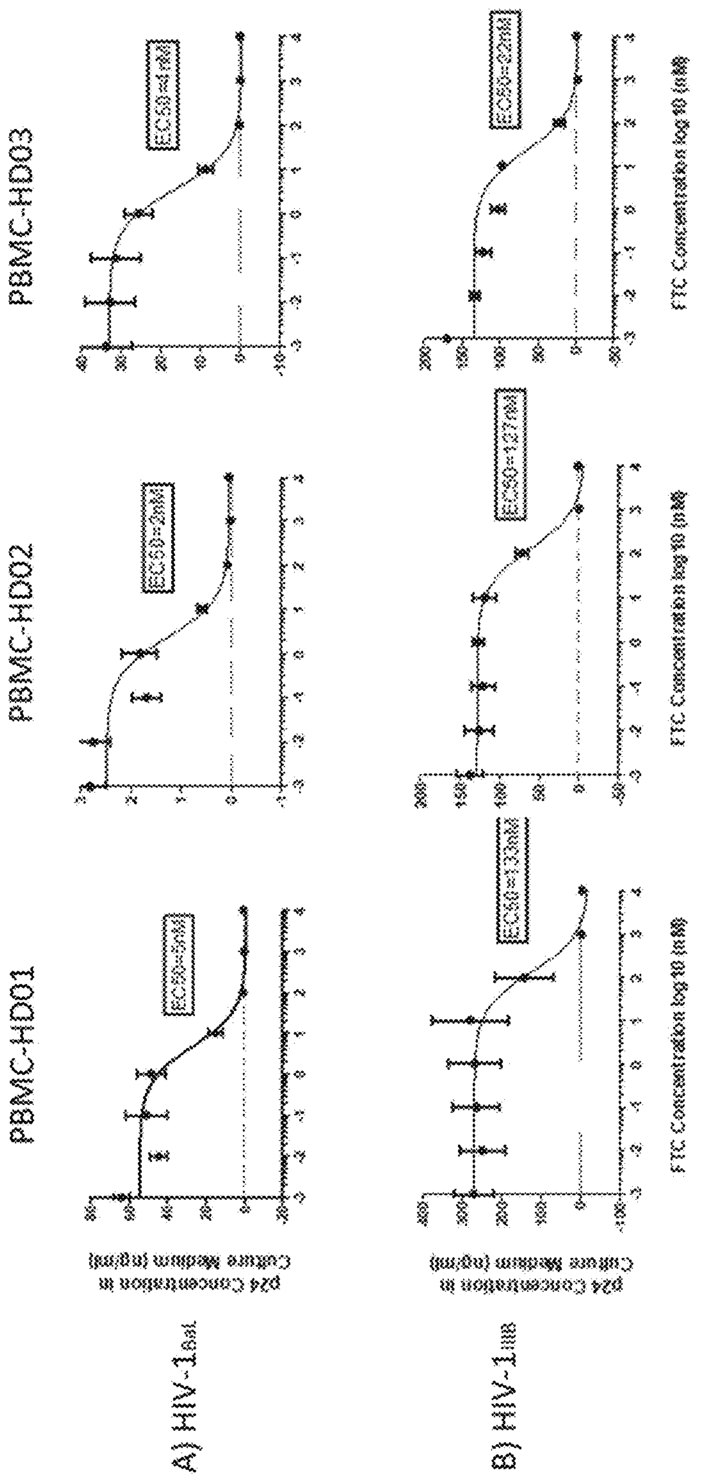
FIG. 6: (A) shows the Antiviral Effect of Emtricitabine (FTC) as a control PBMCs from three separate donors infected with the HIV-1BaL virus; (B) shows the Antiviral Effect of Emtricitabine (FTC) as a control PBMCs from three separate donors infected with the HIV-1IIIB virus. The level of viral infection was determined by the concentration of the p24 viral protein in the cell culture media as on 11 days post-infection, wherein the three PBMC donor cells were labelled as PBMC-HD01, HD02 and HD03.

The antiviral activity of GPS488 (12a) and GPS491 (12c) was also evaluated in peripheral blood monocytes from three separate donors. As shown in FIGS. 4A and 4B, the GPS491 (12c) demonstrated $EC_{50}$ values of 480 nM, 110 nM and 211 nM when tested against the HIV-1Bal strain and $EC_{50}$ values of 655 nM, 962 nM and 921 nM when tested against the HIV-1 IIIB strain. The GPS488 (12a) compound also underwent testing at increasing dose concentrations for its ability to reduce HIV infectivity in peripheral blood monocytes from three separate donors. As shown in FIGS. 5A and 5B, the GPS488 (12a) compound exhibited $EC_{50}$ values of 335 nM, 44 nM, 200 nM when tested against the HIV-1Bal strain and $EC_{50}$ values of 155 nM, 4275 nM and 3338 nM when tested against the HIV-1 IIIB strain. FIG. 6, the $EC_{50}$ values for the anti-HIV drug, emtricitabine (FTC) which was included as a positive control in the peripheral blood monocyte assays.

Figure 7A:
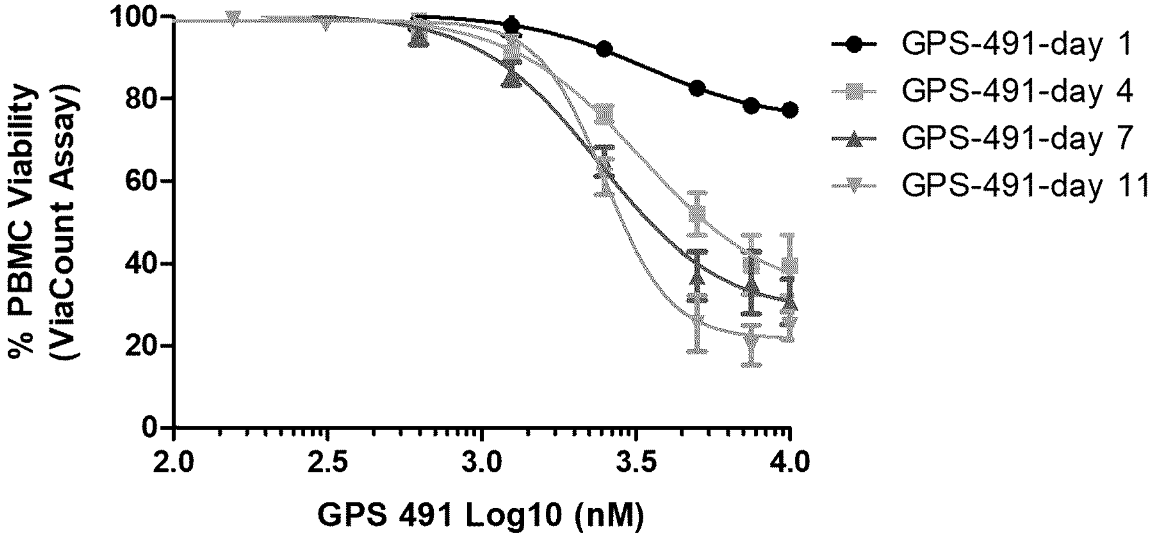
FIG. 7: (A) Evaluation of PBMC viability after 1, 4, 7 or 11 days incubation with GPS491 (12c) at varying concentrations; (B) Evaluation of PBMC viability after 1, 4, 7 or 11 days incubation with GPS488 (12a) at varying concentrations; (C) Evaluation of PBMC viability after 4, 7 or 11 days incubation with FTC; (D) Evaluation of PBMC viability after 4, 7 or 11 days incubation with GPS519 (12e) at varying concentrations. Viability data was measured by the Guava ViaCount assay (data from 3 PBMC donors).
Figure 7B:
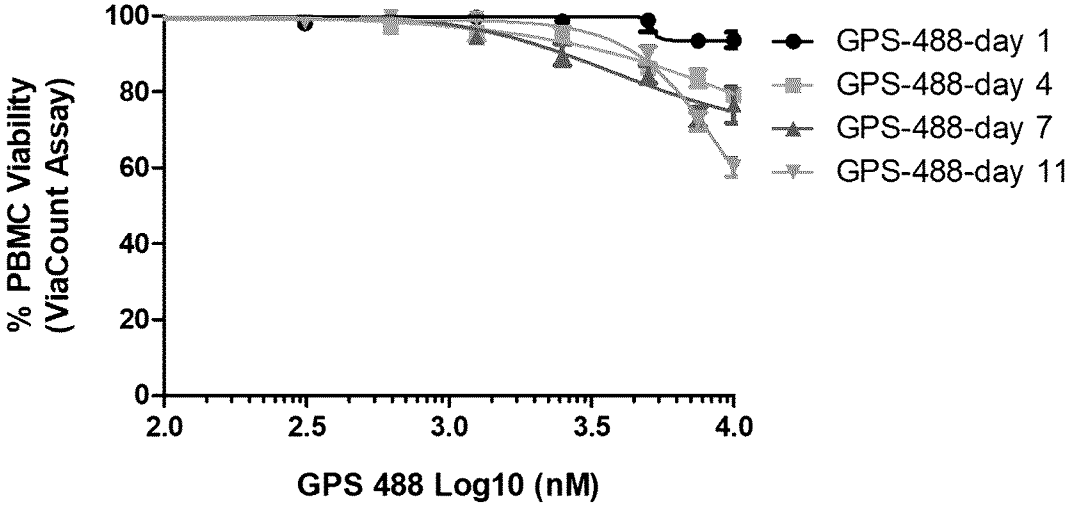
Figure 7C:
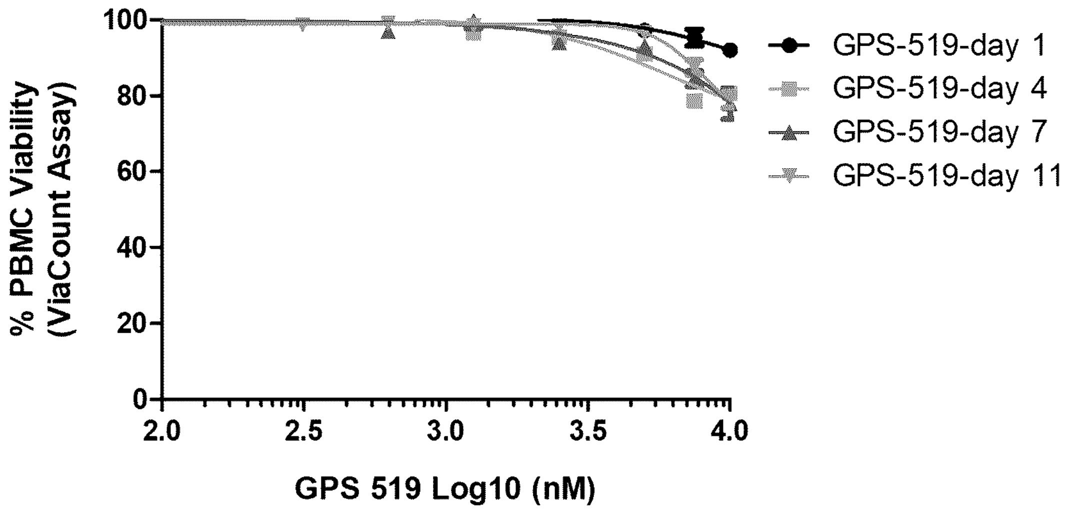
Figure 7D:
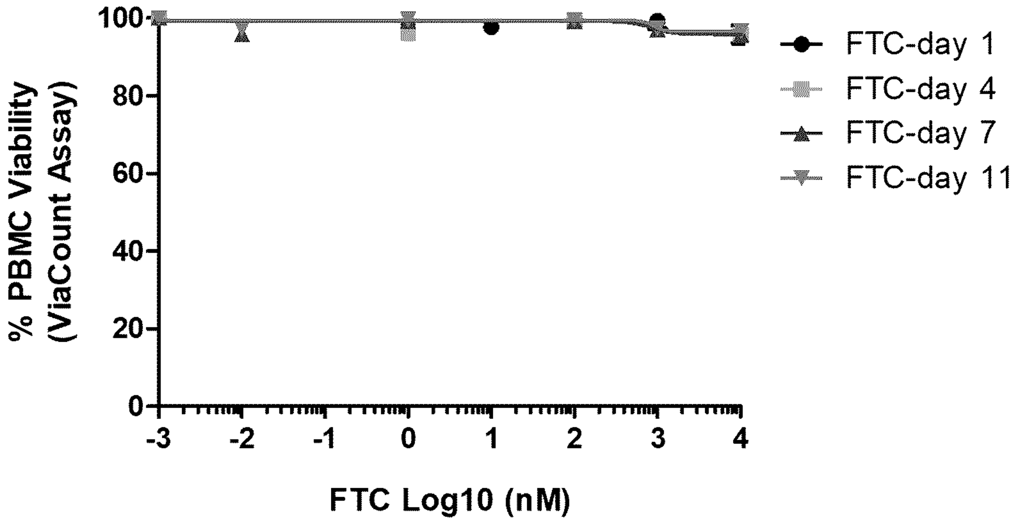

To investigate whether the GPS488 (12a), GPS491 (12c) and GPS519 (12e) exhibited any toxicity toward mammalian cells, cell viability was measured over an 11 day period using the ViaCount assay in PBMCs treated with increasing concentrations of compound. As shown in FIG. 7A-7C, the GPS488 (12a) and GPS491 (12c) showed some cellular toxicity when the cells were exposed in the 0.1-10 μM range, but only minimal toxicity at 1 μM for all three compounds and GPS519 (12e) exhibited minimal toxicity in the same concentration range as compared to the emtricitabine (FTC) control (in FIG. 7D).

Example 3: Calculation of $EC_{50}$ Versus HIV Strains Resistant to the Four Classes of Drugs Currently Used in Antiretroviral Therapy To assess the potential against drug-resistant strains, the antiretroviral activity of the GPS488 (12a) and GPS491 (12c) was tested against key HIV-1 strains that are resistant to at least one of the current four major drug target categories: (non)-nucleoside reverse transcriptase inhibitor (N)NRTI (RTI), protease inhibitor (PI), integrase inhibitor (INI), and CCR5 co-receptor inhibitor (MVC).

Figure 8A:
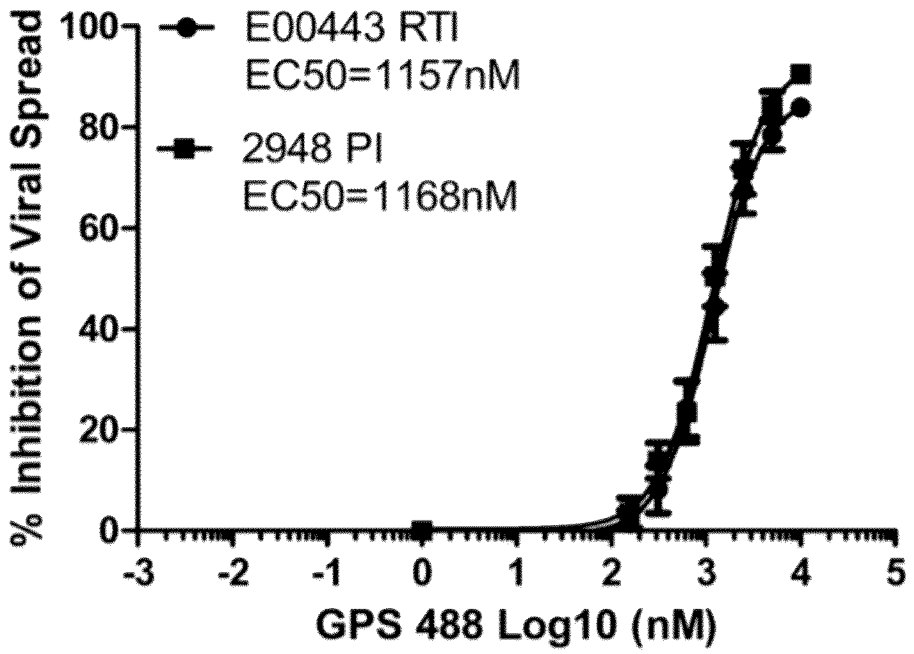
FIG. 8: (A) plots of the anti-HIV-1 activity of GPS488 (12a) against multidrug-resistant clinical isolates; E00443 RTI corresponds to (N)NRTI-resistant isolate and 2948 PI corresponds to a PI-resistant isolate. (B) plots of the anti-HIV-1 activity of GPS488 (12a) against multidrug-resistant clinical isolates; 11845 INI resistance corresponds to an INI-resistant isolate and MVC res entry corresponds to a Maraviroc-resistant R5 strain.
Figure 9A:
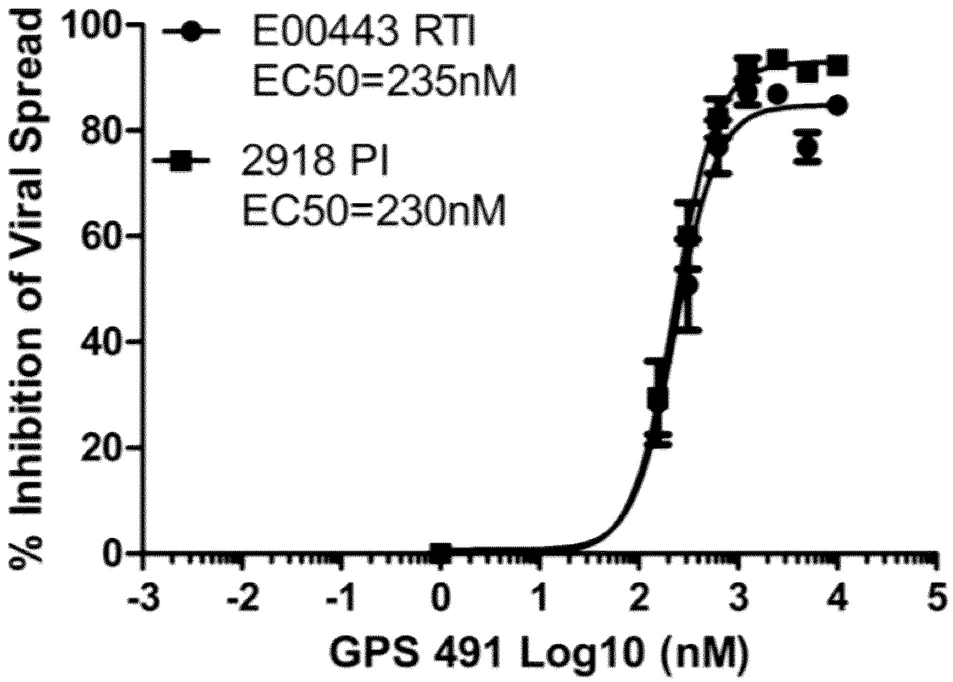
FIG. 9: (A) Shows a series of plots of the anti-HIV-1 activity of GPS491 (12c) against multidrug-resistant clinical isolates; E00443 RTI corresponds to (N)NRTI-resistant isolate and 2918 PI corresponds to a PI-resistant isolate. (N)NRTI-resistant isolate and PI-resistant isolate. (B) Shows a series of plots of the anti-HIV-1 activity of GPS491 (12c) against multidrug-resistant clinical isolates; INI-resistant isolate, MVC-resistant R5 strain.

The Compounds GPS488 (12a) and GPS491 (12c) were evaluated against the isolate (E00443), which has greatly reduced susceptibility to both NNRTI's and NRTI's. Indeed, this isolate harbors a variety of mutations, including the widely recognized NNRTI-resistance mutation K103N that confer high level resistance to Efavirenz™ (EFV) and Nevirapine™ (NVP). This virus also carries the NRTI-resistance mutations D67N, K70R, Y115F, Q151M, M184V, and K219Q, which confer high-level resistance to lamivudine (3TC), Abacavir™ (ABC), Zidovudine™ (AZT), and Emtricitabine™ (FTC). This combination reduces the susceptibility to Atazanavir™ (ATV) and Lopinavir™ (LPV), currently the two of the three most frequently prescribed HIV protease inhibitors. In the assay compounds GPS488 (12a) and GPS491 (12c) remained active, with an $EC_{50}$ of 1157 nM and 235 nM respectively (FIG. 8A, 9A). Compounds GPS488 (12a) and GPS491 (12c) similarly retained its potency ($EC_{50}$ of 1168 nM and 230 nM, respectively) against the PI-resistant isolate (2948), which contains substitutions G48V and L90M (FIGS. 8A and 9A).

Figure 8B:
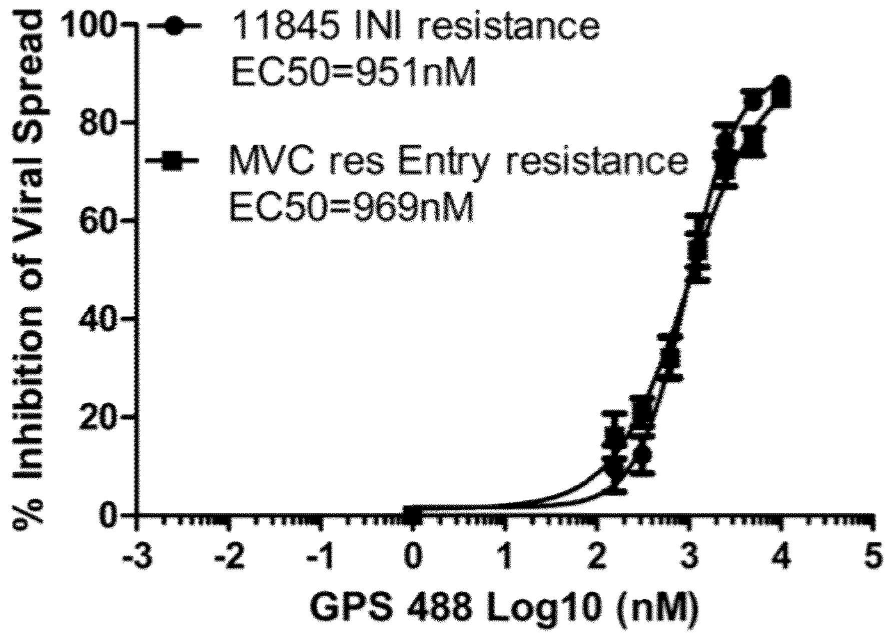
Figure 9B:
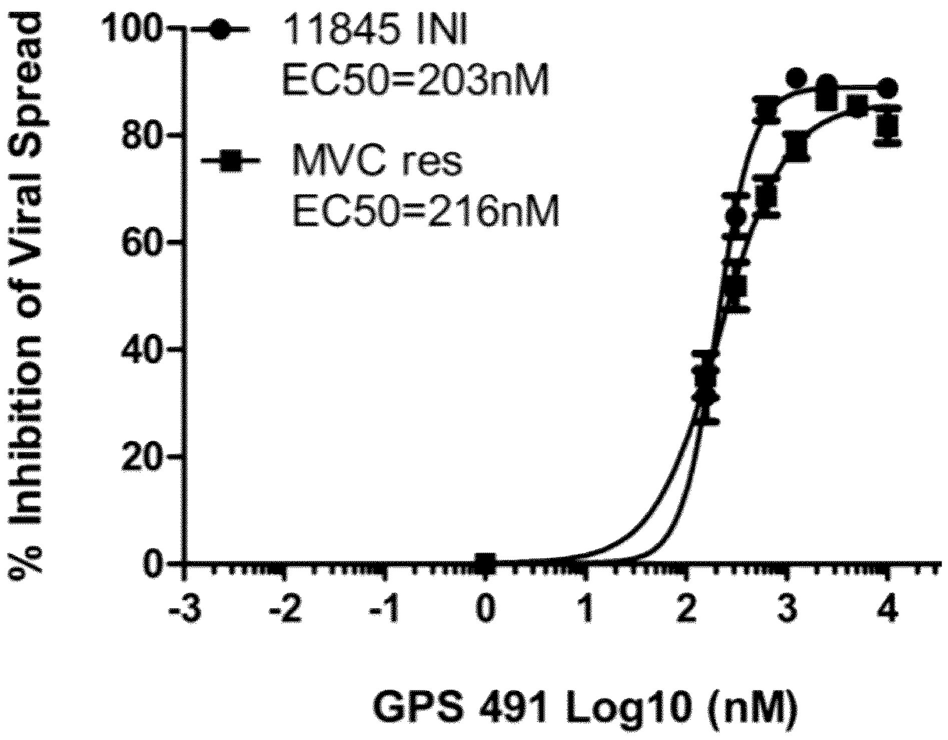

To determine whether GPS488 (12a) and GPS491 (12c) targets HIV-1 integrase, it was tested against a clinical isolate (11845 INI), which harbors G140S and Q148H substitutions that reduce susceptibility to Raltegravir™ (RAL) and Elvitegravir™ (EVG) more than 100-fold and reduce sensitivity toward Dolutegravir™ (DTG) up to 10-fold. As shown in FIGS. 8B and 9B, GPS491 (12c) yielded an $EC_{50}$ of 203 nM and GPS488 (12a) yielded an $EC_{50}$ of 951 nM against the 11845 clinical isolate. As shown in FIGS. 8B and 9B, Compounds GPS488 (12a) and GPS491 (12c) retained activity ($EC_{50}$ of 969 nM and 216 nM, respectively) against an HIV-1 strain that is resistant to the entry inhibitor-based drug Maraviroc™ (MVC). This Maraviroc-resistant variant derived from a R5 strain of HIV-1BaL contains five mutations within the envelope V3 loop: A19T, L20F, T22A, E25D, and I26V.

Figure 10A:
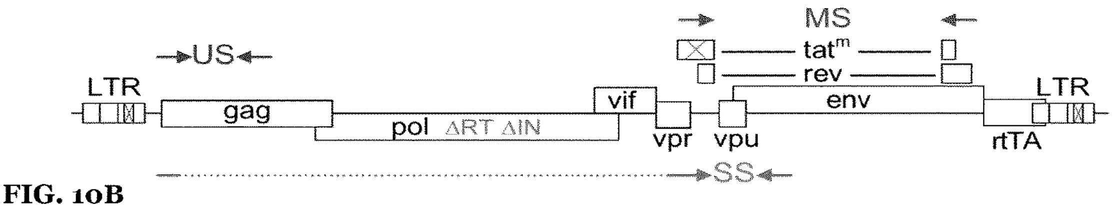
FIG. 10: (A) shows a map of donor and acceptor splice sites used for the production of the major HIV mRNAs (SS—singly spliced; US—unspliced; MS—multiply spliced). (B) shows quantitative RT-qPCR assays from HeLa B2 cells treated with varying concentrations of GPS491 (14c) or left untreated (DMSO (−) Dox) or treated with doxycycline ((+) Dox DMSO) as a positive control to induce the provirus in HeLa B2 cells. Error bars indicate standard deviation, and (*) indicates P<0.001. N=3. (C) shows end-point RT-qPCR assays from HeLa-HIV cells treated with a 10 μM of GPS compounds; GPS389 (5a), GPS428 (5c), GPS440 (8a), or 1.25 μM GPS491 (12c) or left untreated (minus) or treated with doxycycline (Dox) as a positive control. GPS431 is included in the assay as an inactive compound from the library for comparison.
Figure 10B:
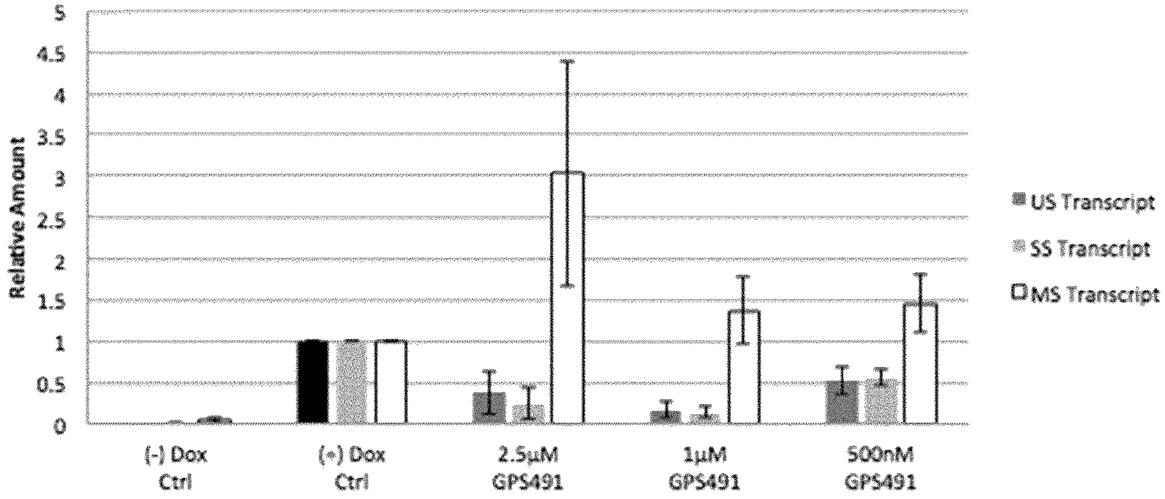
Figure 10C:
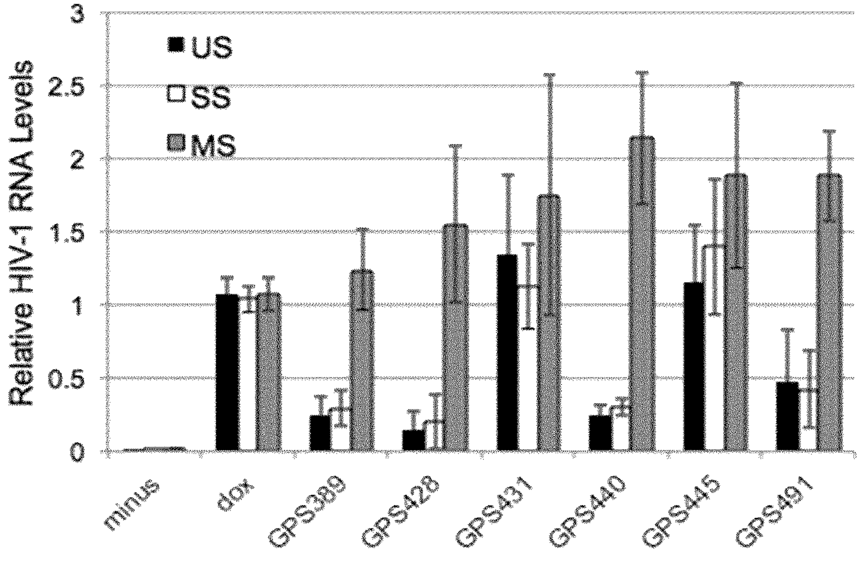

Example 4: Impact of GPS Compounds on the Splicing of HIV Transcripts and Viral Protein Translation Endpoint PCR and quantitative RT-PCR were used to monitor the impact of compounds on the splicing of HIV transcripts using primers (US, SS and MS) as shown in FIG. 10A. As shown in FIG. 10B, various concentrations of GPS491 (12c) (2.5 μM, 1.0 μM, 500 nM) resulted in a reduction in the US and SS transcript levels relative to the Dox control in Hela B2 cells. A similar impact on the generation of the US and SS transcripts was also observed for cells treated with GPS389 (5a), GPS428 (5c), GPS440 (8a), GPS445 (5g) and GPS491 (12c) in the HeLa rtTA-HV-ΔMls (FIG. 10C), where GPS431 is included as an inactive compound for comparison.

Figure 11:
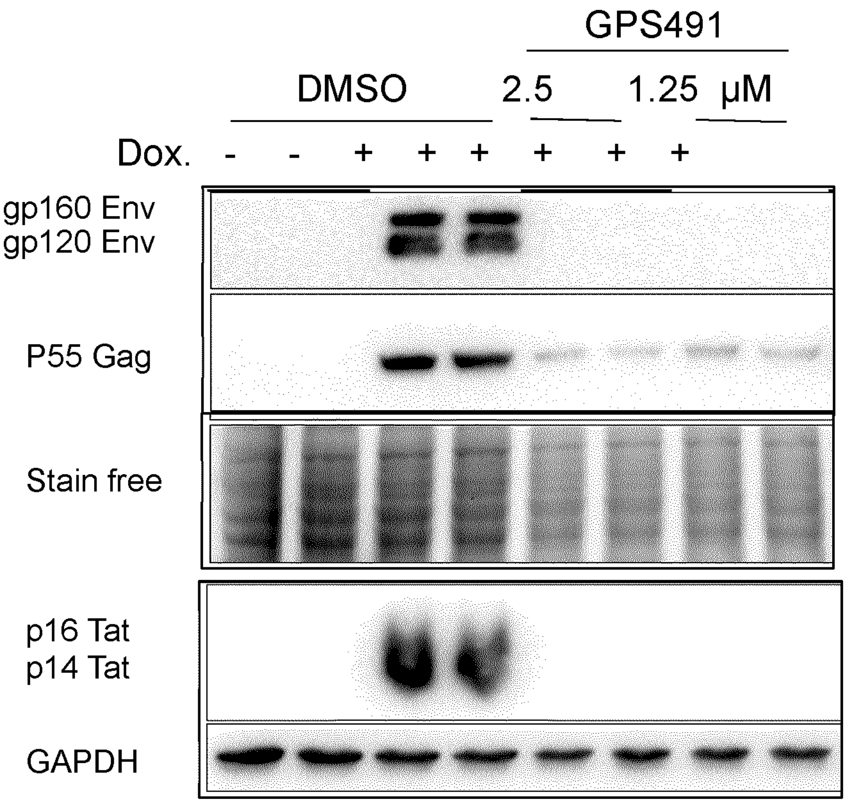
FIG. 11: shows that GPS491 (12c) reduces viral protein levels in B2 HeLa cells. (A) Shows the Western blot data in graphical forms with the average protein levels (Gag, Env and Tat) relative to the doxycycline positive control, error bars are the standard deviation. (*) indicates P<0.001, N=3 HeLa cells B2 were either exposed to Doxycline™ (Dox) or left untreated with DMSO alone and exposed to increasing concentrations of GPS491 (250 nm to 2.5 μM) with doxycycline. Relative Gag, Env and Tat levels were normalized to the total protein loading control. Total protein levels were quantified using BioRad™ Stain-Free Gel system. (B) shows the Tat protein levels normalized to GAPDH loading control by Western blot in HeLa cells B2 either exposed to Dox or left untreated with DMSO alone and exposed to varying concentrations of GPS491 (12c) (250 nm to 2.51M) with Dox. Dox was used to induce the provirus in HeLa B2 cells.
Figure 11:
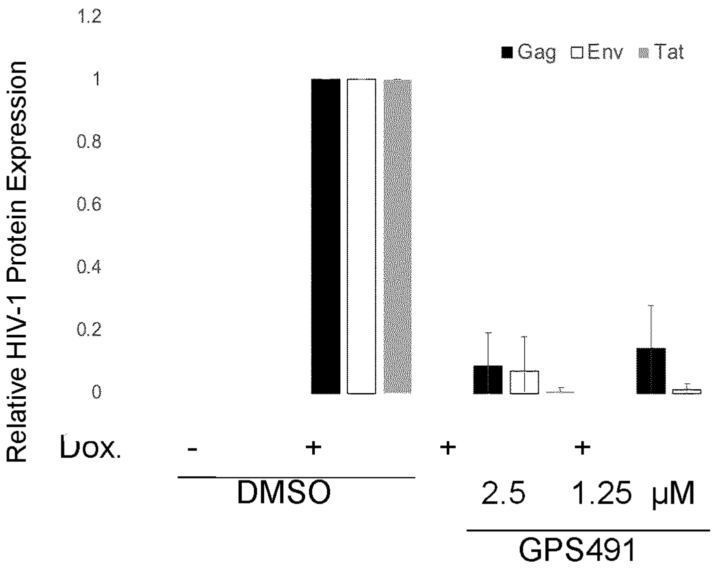
Figure 12A:
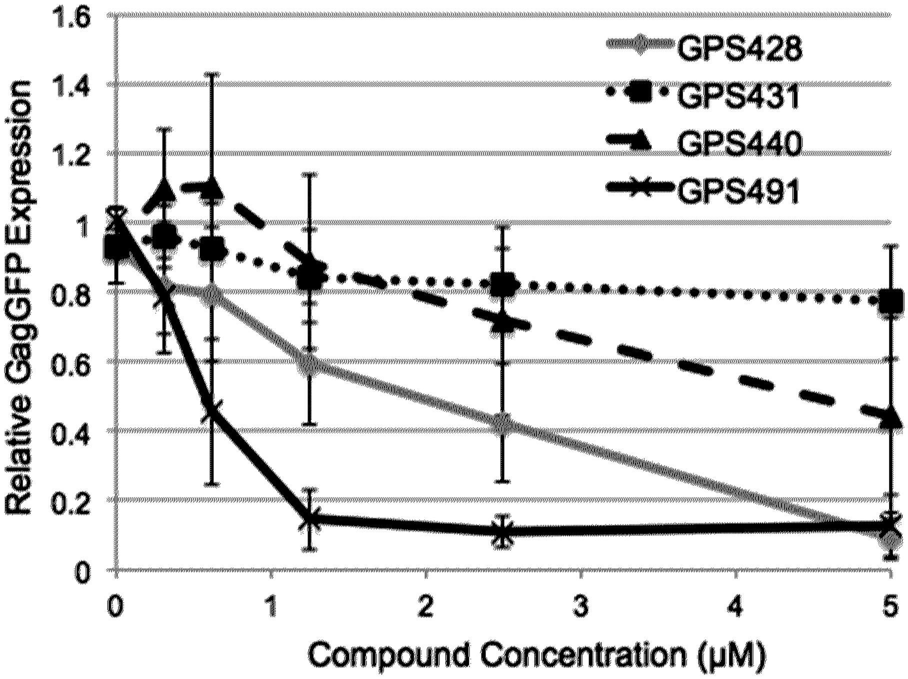
FIG. 12: shows the effect of increasing concentration of selected GPS compounds (GPS428 (5c), GPS440 (8a), GPS491 (12c)) on HIV-1 protein expression in HeLa HIV Δmls rtA cells, where HeLa HIV-1 cells were treated with either DMSO or the test compound for 4 hrs. prior to a 24 hr. incubation with doxycycline (dox) to induce provirus expression, before cells were harvested for viral protein and viral protein levels were assessed. (A) shows the relative expression of HIV Gag(GFP) as assessed by HIVGag(p24) ELISA. (B) shows the relative cell viability as assessed by Alamar Blue of HeLa HIV-1 cells exposed to increasing concentrations of GPS428 (5c), GPS440 (8a), GPS491 (12c) GPS431 is an inactive compound from the library that was included in the assay for comparison.
Figure 12B:
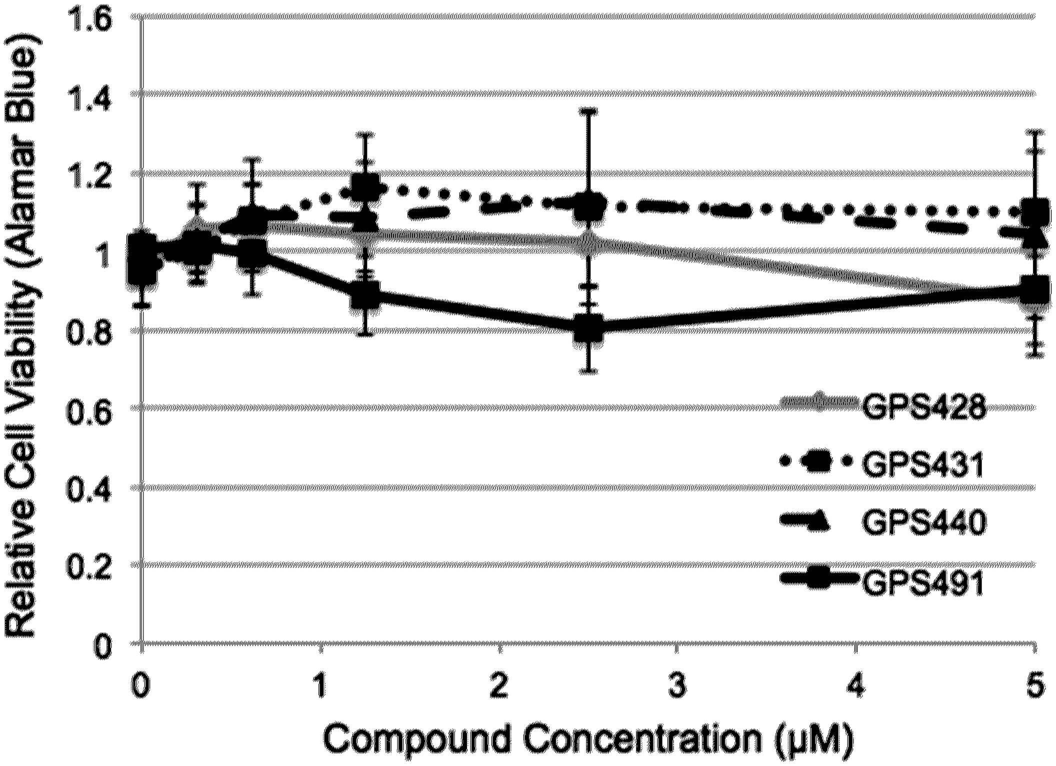

Next the impact of the GPS compounds on viral protein production was determined in Hela B2 cells. As shown in FIG. 11, reduced expression of the Env, Tat and Gag were observed at increased concentrations of GPS491 (12c). FIG. 12A shows the impact of a selection of GPS compounds to impact Gag expression at increasing compound concentration in a HeLa cell line with Gag where the HIV-1 provirus is expressed by doxycycline.

Figure 13A:
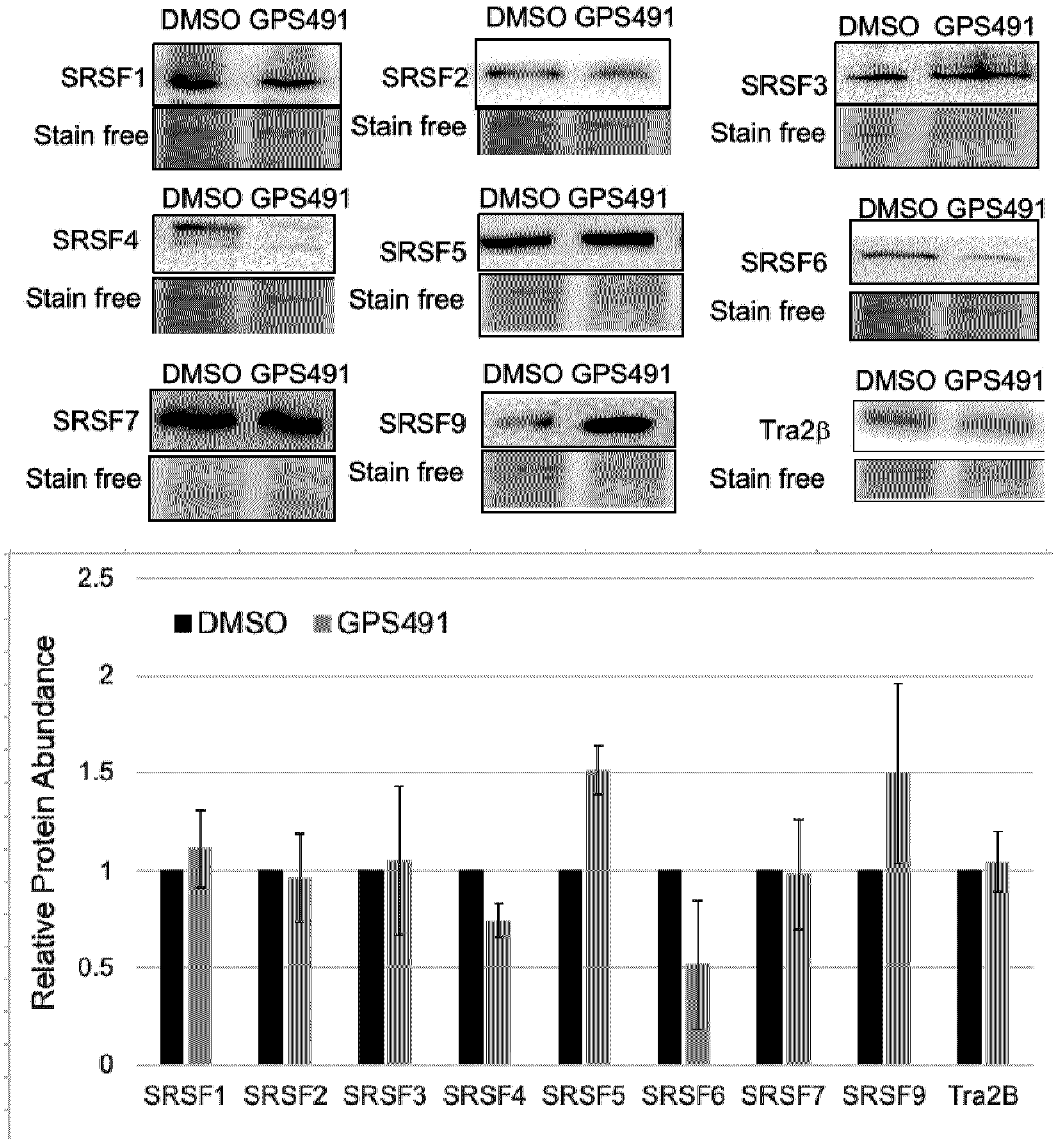
FIG. 13: GPS 491 (12c) alters the expression and phosphorylation of select SR proteins. HeLa rtTA HIVΔmls cells were treated with DMSO or GPS491+ doxycycline for 24 h. Cells were then harvested in RIPA buffer containing phosphatase inhibitors and lysates fractionated on StainFree SDS-PAGE gels. (A) Representative western blots for each SR protein are shown, with a summary of western blots from three independent groups of samples measuring the effect of GPS491 on SR proteins levels relative to DMSO treated cells. (B) Cell lysates were mock treated or treated with alkaline phosphatase (PPase) prior to loading onto Stainfree cells. After transfer onto PVDF, blots were probed for SRSF4. Blots are representative of n>3 independent assays.
Figure 13B:
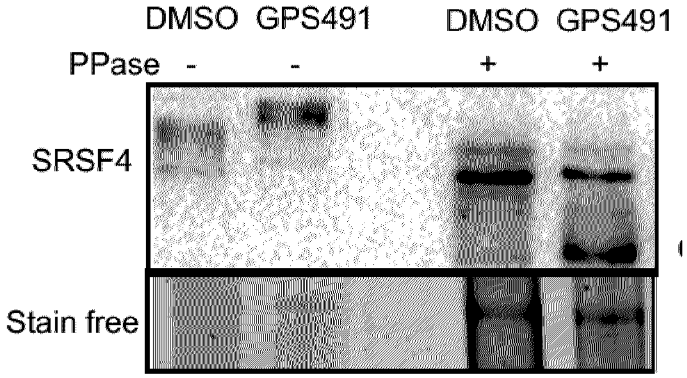

Example 5: Impact of Compounds GPS491 and GPS488 on the Expression/Modification of Host Protein Splicing Factors To determine if the GPS compounds displayed any effect on SR protein abundance or modification, levels of multiple SR proteins was measured in HeLa B2 cells. Briefly, cell lysates from HeLa rtTA HIVΔmls cells treated for 24 h with either DMSO or GPS491 were fractionated on SDS-PAGE gels and individual factors detected by Western blot. As shown in FIG. 13(A), incubation with GPS491 (12c) 2.5 μM selectively altered SR protein abundance, increasing levels of both SRSF5 and SRSF9 1.5 fold while reducing SRSF4 and SRSF6 abundance by 20% and 50%, respectively. Limited changes in the levels of the other SR/SR-related factors examined were observed. However, in addition to changes in SR protein abundance, we also noted a shift in SRSF4 migration consistent with an increase in its extent of phosphorylation. To address whether this was indeed the case, cell extracts were treated with or without alkaline phosphatase prior to SDS-PAGE and western blotting. As indicated in FIG. 13(B), treatment with phosphatase (PPase) increased SRSF4 mobility for all samples and eliminated the mobility difference observed between DMSO and GPS491 treated samples, consistent with the altered mobility being due to increased phosphorylation.

Figure 16A:
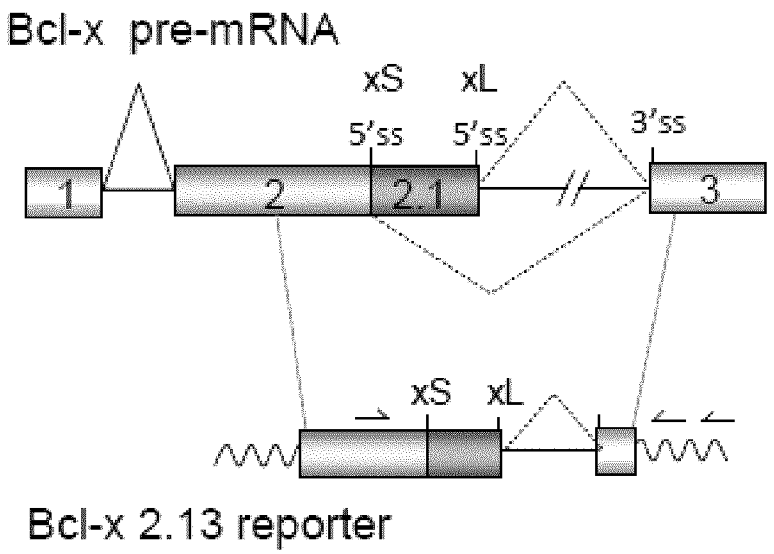
FIG. 16: (A) shows a map depicting the Bcl-x pre-mRNA and the Bcl-x minigene x2.13 and the position of the primers used for RT-PCR $(B)_{293}$ cells treated with 10 μM of GPS488 that were co-transfected a plasmid carrying the Bcl-x minigene X2.13 and a plasmid containing the CMV promoter driving the expression of either myc, SRSF2, SRSF3, SRSF4, Tra2a, Tra2b, SRSF10 or SRSF7 (C) shows the RT-PCR data corresponding to the histograms in (B) showing the relative abundance of the xS and xL transcript splice variants.
Figure 16B:
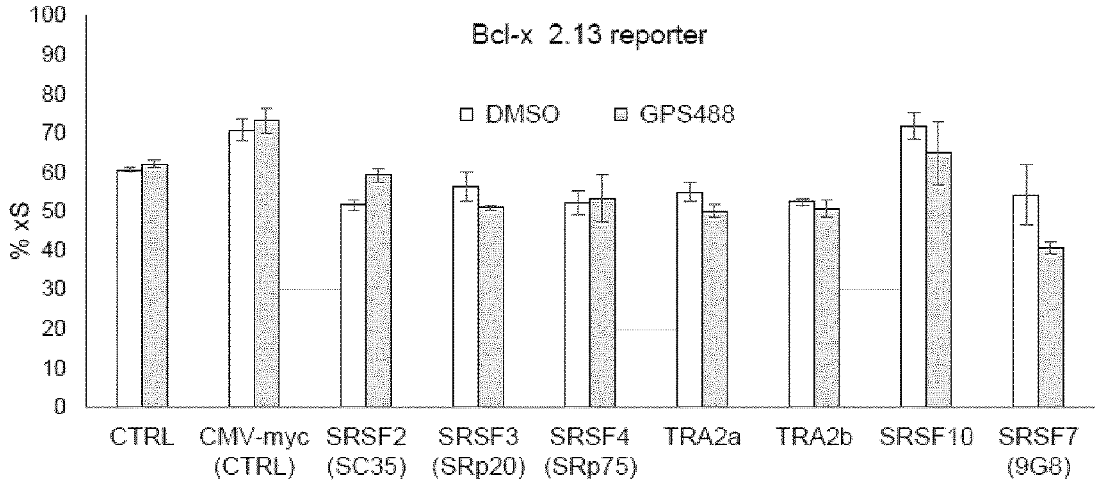
Figure 16C:
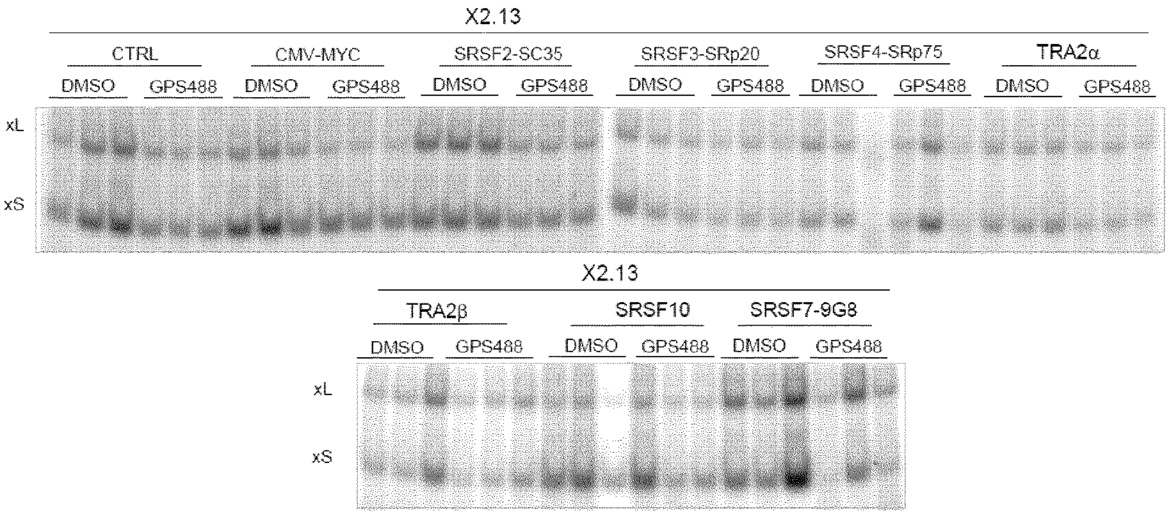
Figure 17A:
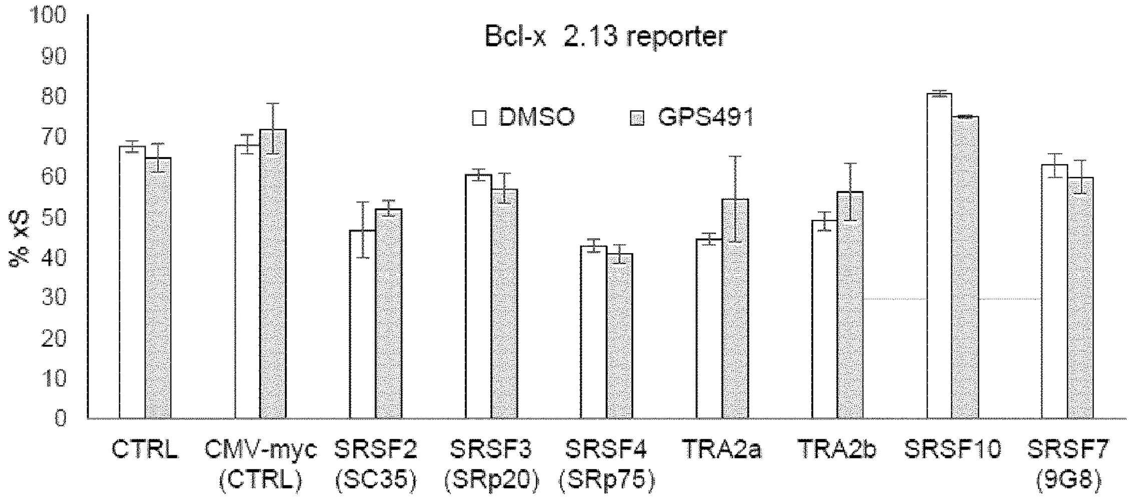
FIG. 17: $(A)_{293}$ cells treated with 10 μM of GPS 491 (12c) that were co-transfected a plasmid carrying the Bel-x minigene X2.13 and a plasmid containing the CMV promoter driving the expression of either myc, SRSF2, SRSF3, SRSF4, Tra2a, Tra2b, SRSF10 or SRSF7 (B) shows the RT-PCR data corresponding to the histograms in (A) showing the relative abundance of the xS and xL transcript splice variants.
Figure 17B:
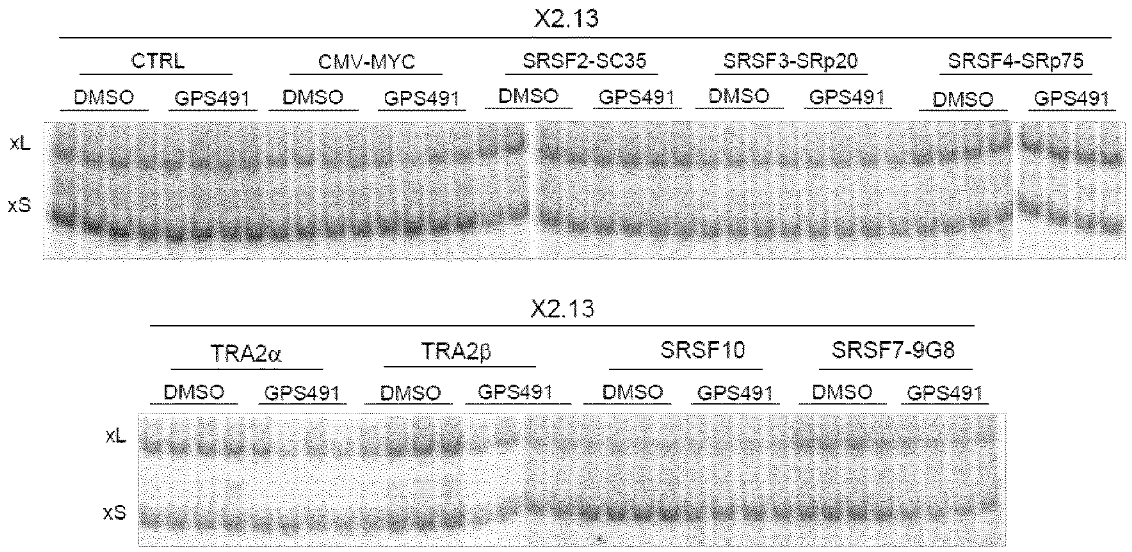
Figure 18A:
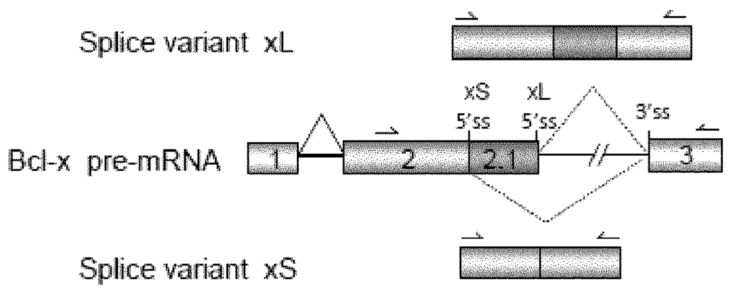
FIG. 18: (A) shows a map of the Bcl-x ENDO construct with the primers used to detect the xL and xS splice variant transcripts. (B) Treatment of 293 cells co-transfected with the Bcl-X endo reporter and the SRSF10 construct with 10 μM of GPS491 (12c) compound shows a shift in the generation of the xS splice variant transcript. (C) Treatment of 293 cells co-transfected with the Bcl-X endo reporter and the SRSF10 construct with 20 μM of GPS491 (12c) compound shows a shift in the generation of the xS splice variant transcript.
Figure 18B:
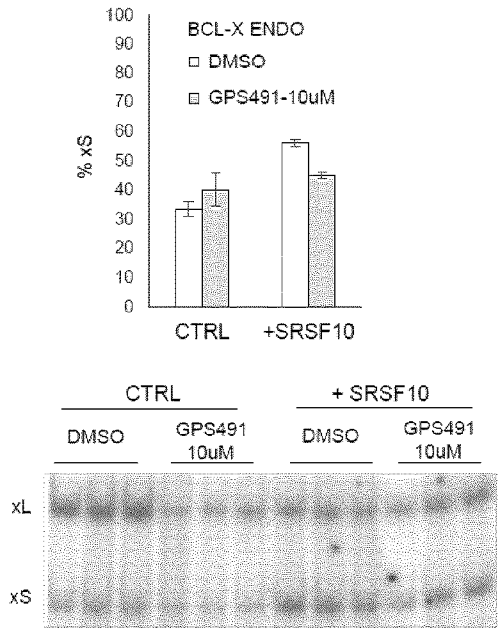
Figure 18C:
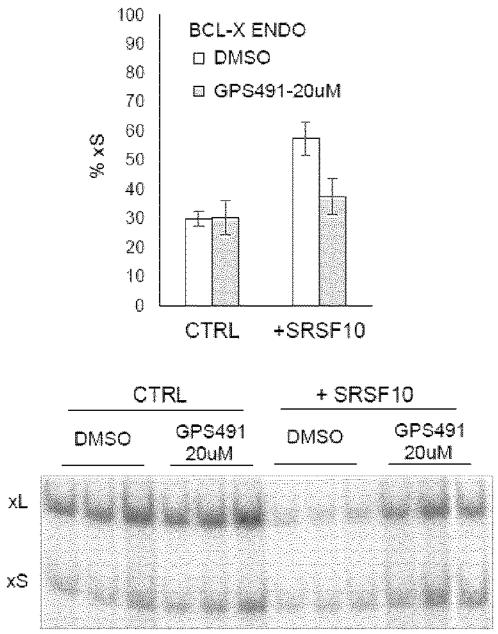

To further explore the impact of the GPS compounds on SR proteins, we tested whether GPS488 (12a) and GPS491 (12c) impacted an SR-protein induced shift in splicing of the Bcl-x transcript. Briefly, plasmids expressing either SRSF2, SRSF3, SRSF4, TRA2a, TRA2b, SRSF7 or SRSF10 were co-transfected into 293 cells with the X2.13 Bcl-x reporter mini-gene (shown in FIG. 16A), and the levels of the Bel-xL and Bel-xS splice variant transcripts were measured by RT-PCR after a 24 hour treatment with 10 μM of either GPS488 (12a) or GPS491 (12c) compound or a DMSO control. As shown in FIGS. 16B and 16C, the treatment with the GPS488 (12a) compound in conjunction with the presence of the SRSF2 resulted in an increased abundance of the Bel-xS transcript splice variant, whereas the presence of the SRSF7 protein resulted in a decreased abundance of the Bel-xS transcript splice variant. As shown in FIGS. 17A and 17B, the treatment of the transfected 293 cells with GPS491 (12c) compound in conjunction with the SRSF10 protein led to a reduction in the Bel-x-S splice variant. The effect of the GPS491 (12c) compound on splicing mediated by SRSF10 was confirmed in Bcl-X endo reporter, as shown in FIG. 18 when cells were treated with either 10 μM or 20 μM of the GPS491 (12c) compound.

Figure 19A:
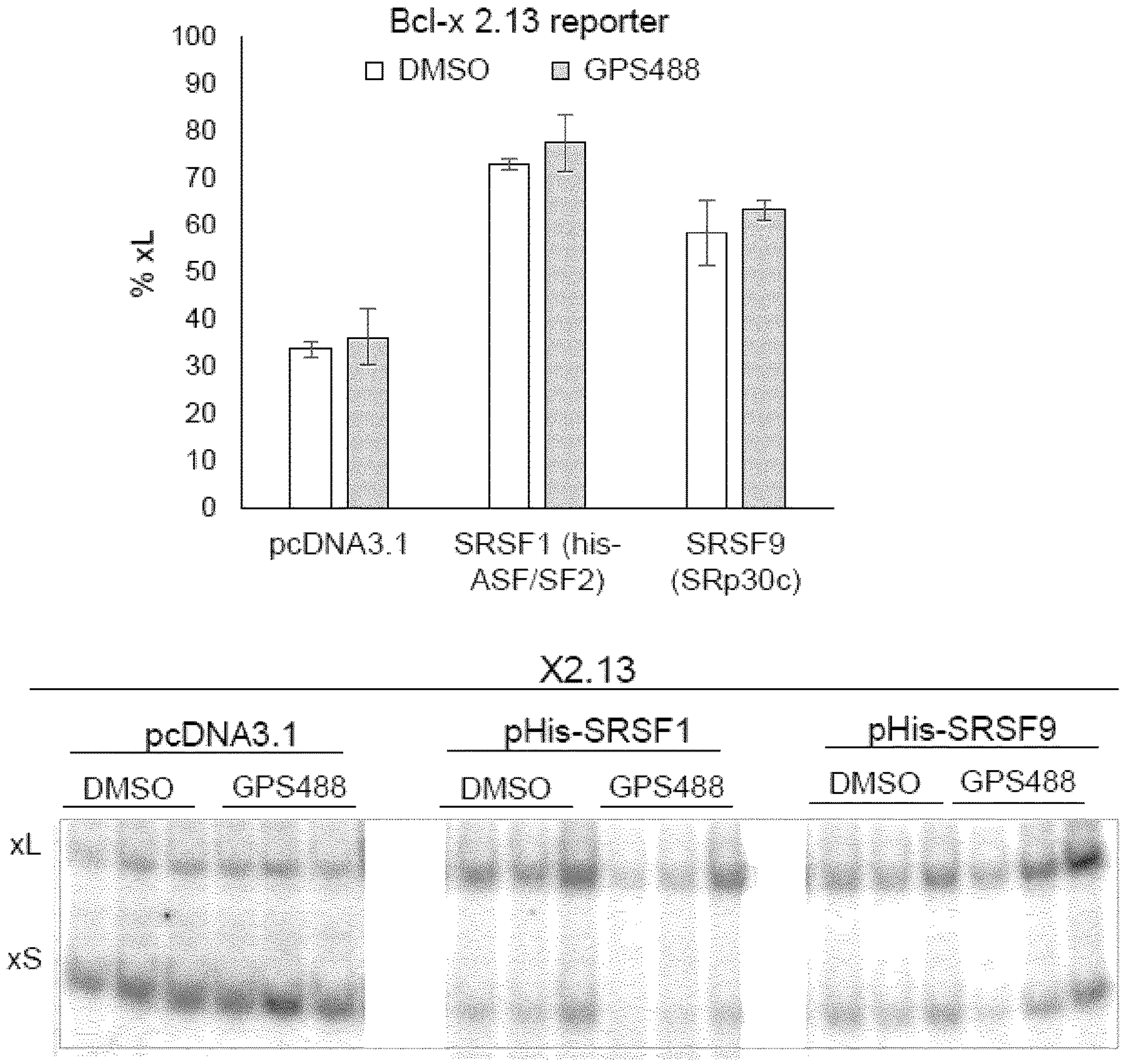
FIG. 19: (A) The addition of the GPS488 (12a) at 10 μM or GPS491 (12c) at 10 μM (B) did not alter the shift in splice site use induced by the overexpression of SRSF1 or SRSF9 as compared to the DMSO control.
Figure 19B:
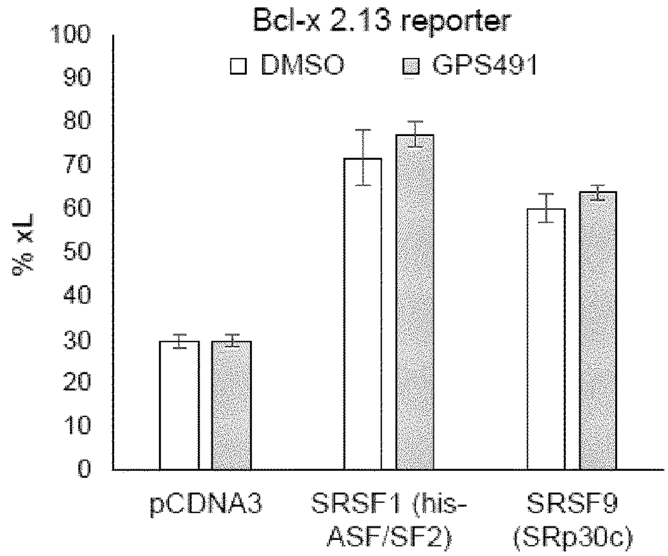
Figure 19B:
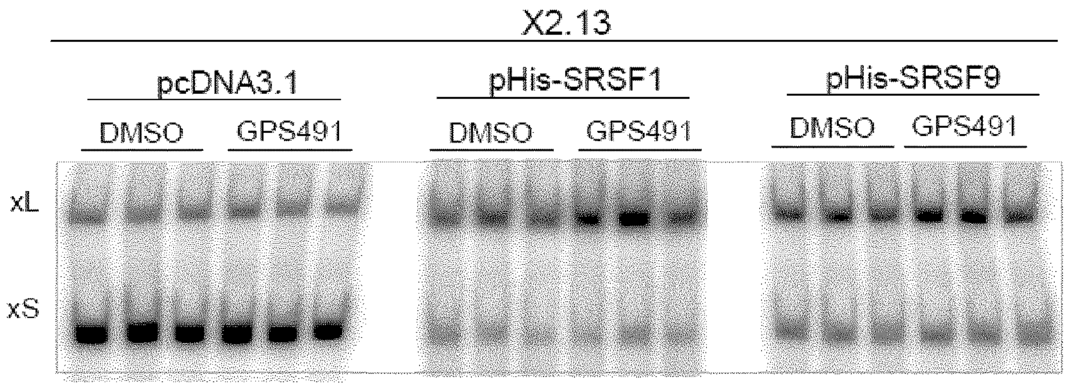

The SRSF1 and SRSF9 proteins are known to shift the Bcl-x splicing in favor the Bel-xL transcript variant. As shown in FIG. 19, the addition of 10 μM of GPS488 (12a) (FIG. 19A) or 10 μM GPS491 (12c) (FIG. 19B) did not have any impact on the generation of the Bel-xL splicing variant.

Example 6: Impact the GPS491 Compound on the Replication of Adenovirus

Figure 14A:
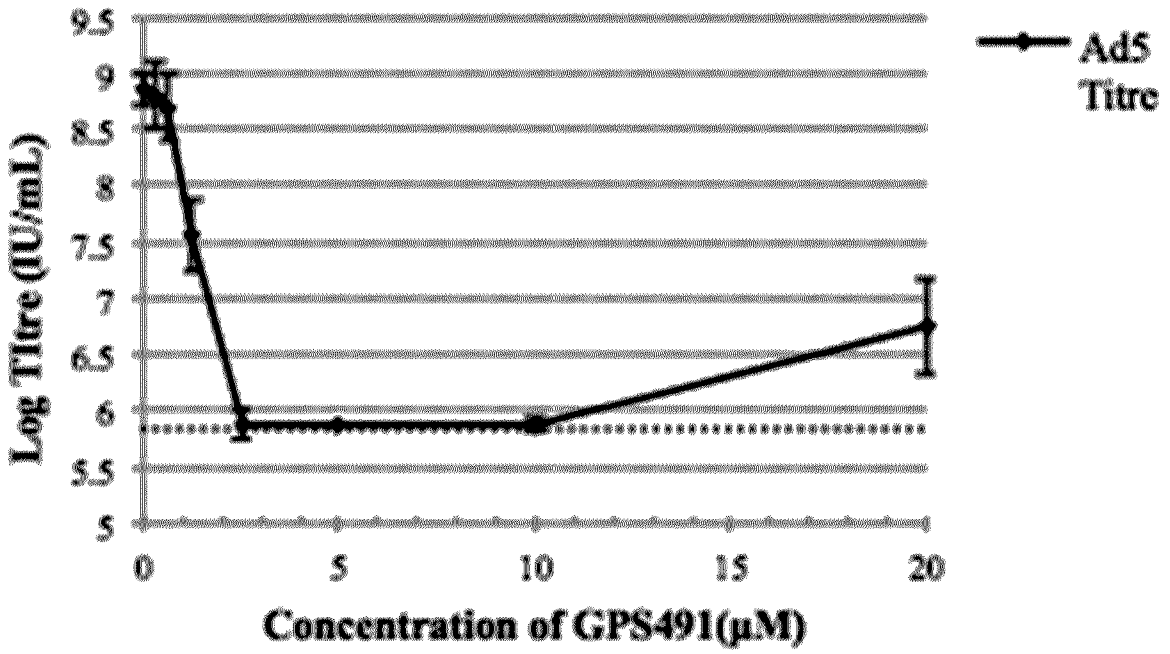
FIG. 14: (A) GPS 491 (12c) inhibits adenovirus (Ad5) replication in A549 cells. To (dotted line) is a sample harvested immediately after the 1 hr adsorption period to measure residual virus from the inoculum. Data points represent the average of duplicate samples. Error bars represent the standard deviation of three experiments. (B) GPS 491 (12c) induced minimal toxicity in A549 cells at increasing concentrations of compound.
Figure 14B:
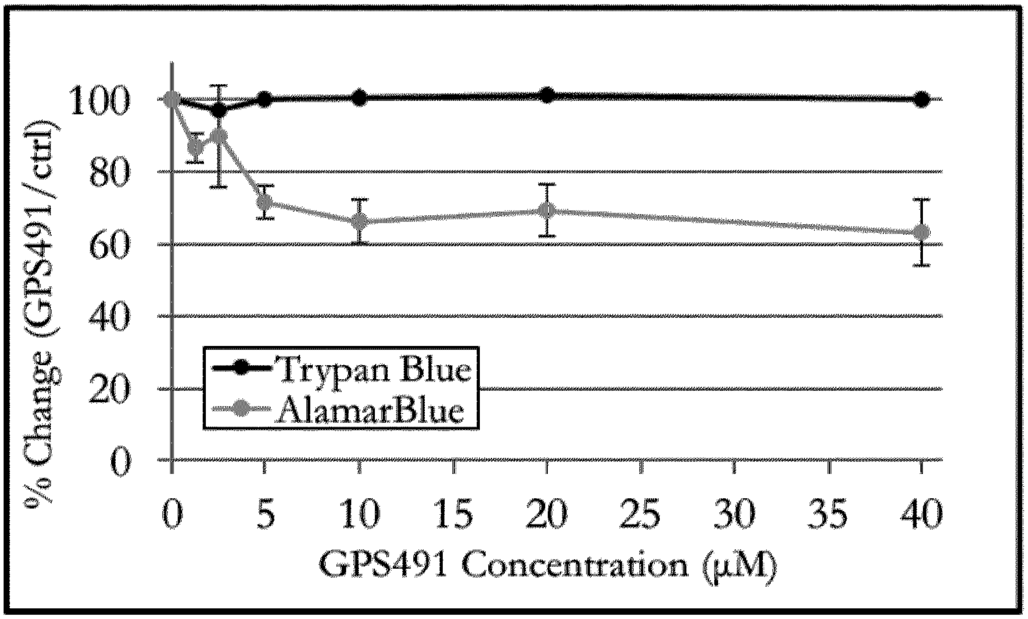
Figure 15A:
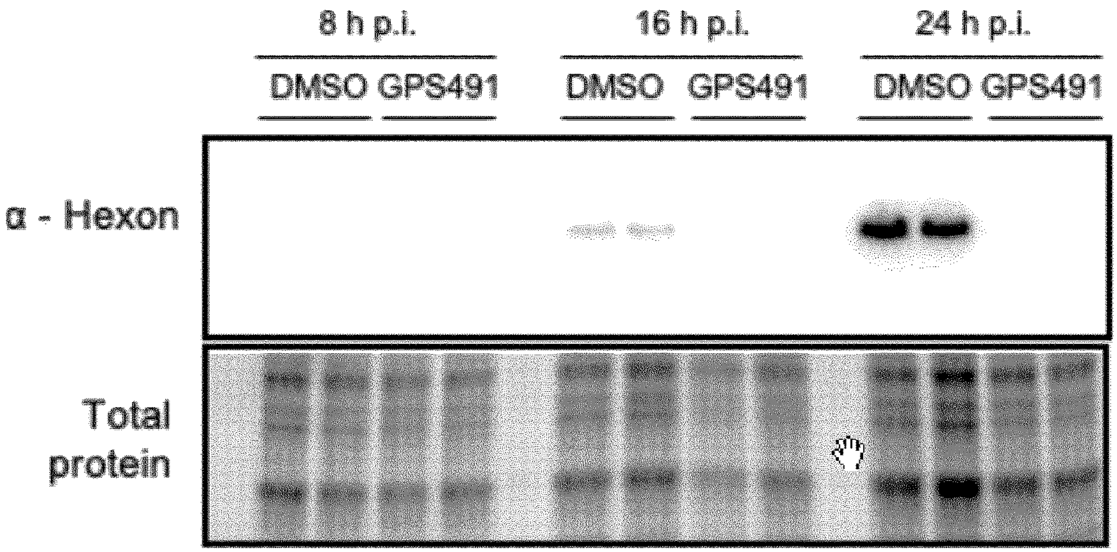
FIG. 15: (A) HAdV-C5 infected A549 cells treated with GPS 491 (12c) compound at 2.5 μM or DMSO were harvested in RIPA buffer at 8 h, 16 h and 24 h p.i. to examine hexon protein expression. (B) HAdV-C5 infected A549 cells treated with either DMSO alone, GPS 491 (12c) compound at 2.5 μM or an uninfected control and were fixed with 4% PFA after 8 h post infection and analyzed by immunofluorescence imaging for cells and stained to detect adenovirus hexon or E1A proteins. (C) HAdV-C5 infected A549 cells were harvested in RIPA buffer at 8 h and 16 h p.i to examine E1A protein expression.
Figure 15B:
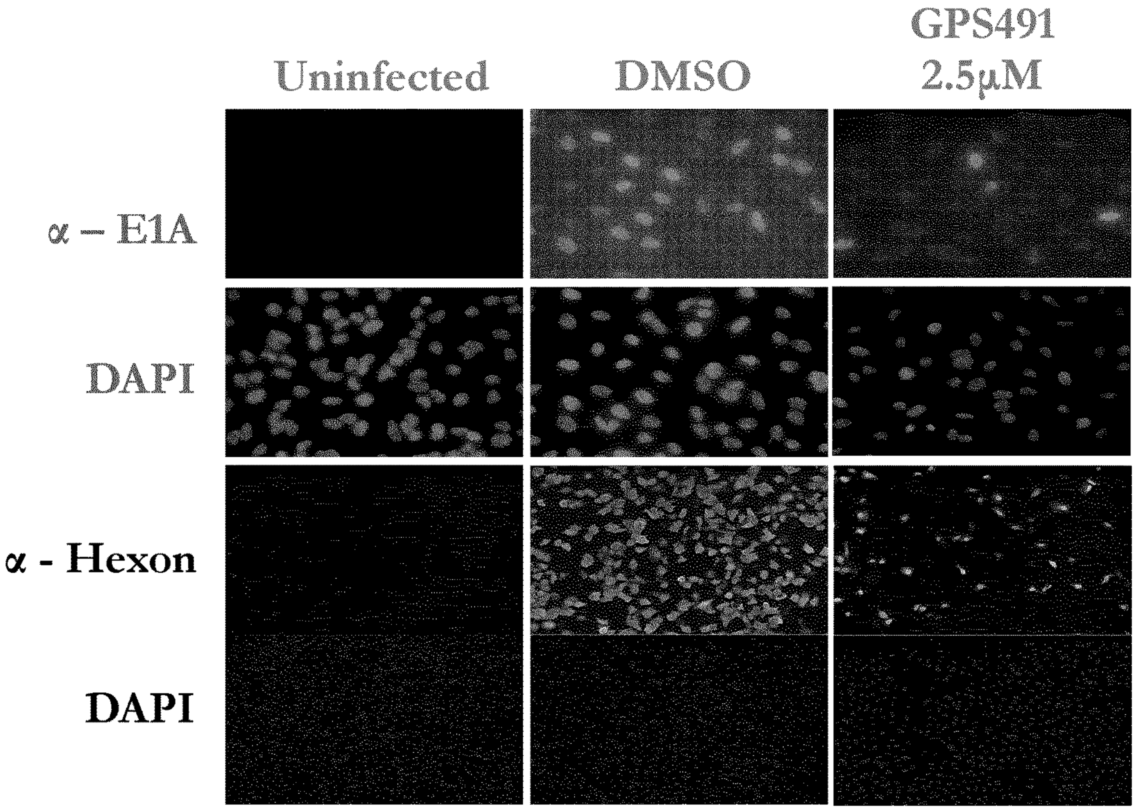
Figure 15C:
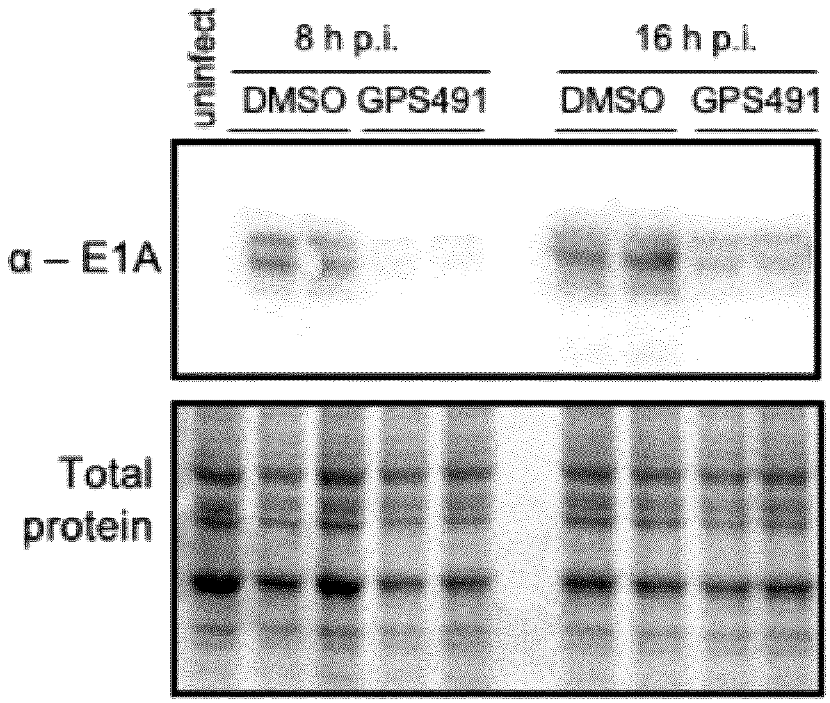

As shown in FIG. 14A, the GPS491 (12c) compound was tested for its ability to inhibit adenovirus (Ad5) replication in A549 cells. Ad5-infected cells were exposed to increasing concentrations of GPS491 (0 μM to 20 μM) for a 24 h incubation period at which point cells/media were collected to determine the viral titres. The calculated $IC_{50}$ of the GPS491 (12c) compound against adenovirus was 1 μM. The GPS491 compound showed minimal toxicity against the A549 cell line over a 24 hr period as shown by trypan blue testing and Alamar Blue™ assay (FIG. 14B). Next, the impact of the GPS491 (12c) compound on viral protein expression of adenovirus was investigated. As shown in FIG. 15, the GPS491 (12c) compound inhibited the expression of the hexon protein and delayed the expression of the E1A protein as shown by Western blot (FIGS. 15A and 15C). By immunofluorescence, the GPS491(12c) also impacted the production of the E1A viral protein and the hexon protein (FIG. 15B).

Figure 20A:
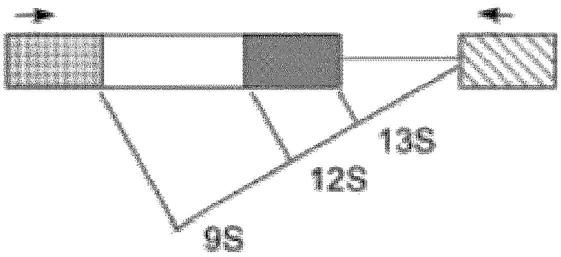
FIG. 20: (A) shows a map depicting the E1A RNA processing events to generate a 13S, 12S or 9S splice variant with arrows showing the location of the primers (B) A549 cells were infected with HAdV-C5 for 1 hr and then the HAdV-C5 infected A549 cells treated with either DMSO alone, GPS491 (12c) compound at 2.5 μM or GPS491 (12c) compound at 5 M. At 8 h, 16 h and 24 h p.i, the levels of E1A RNA isoforms (13S, 12S and 9S) were analyzed by RT-PCR. (C) HAdV-C5 infected A549 cells treated with either DMSO alone, GPS491 (12c) compound at 2.5 μM and were analyzed at 0 h, 16 h, 20 h, and 24 h p.i for the level of viral DNA replication.
Figure 20B:
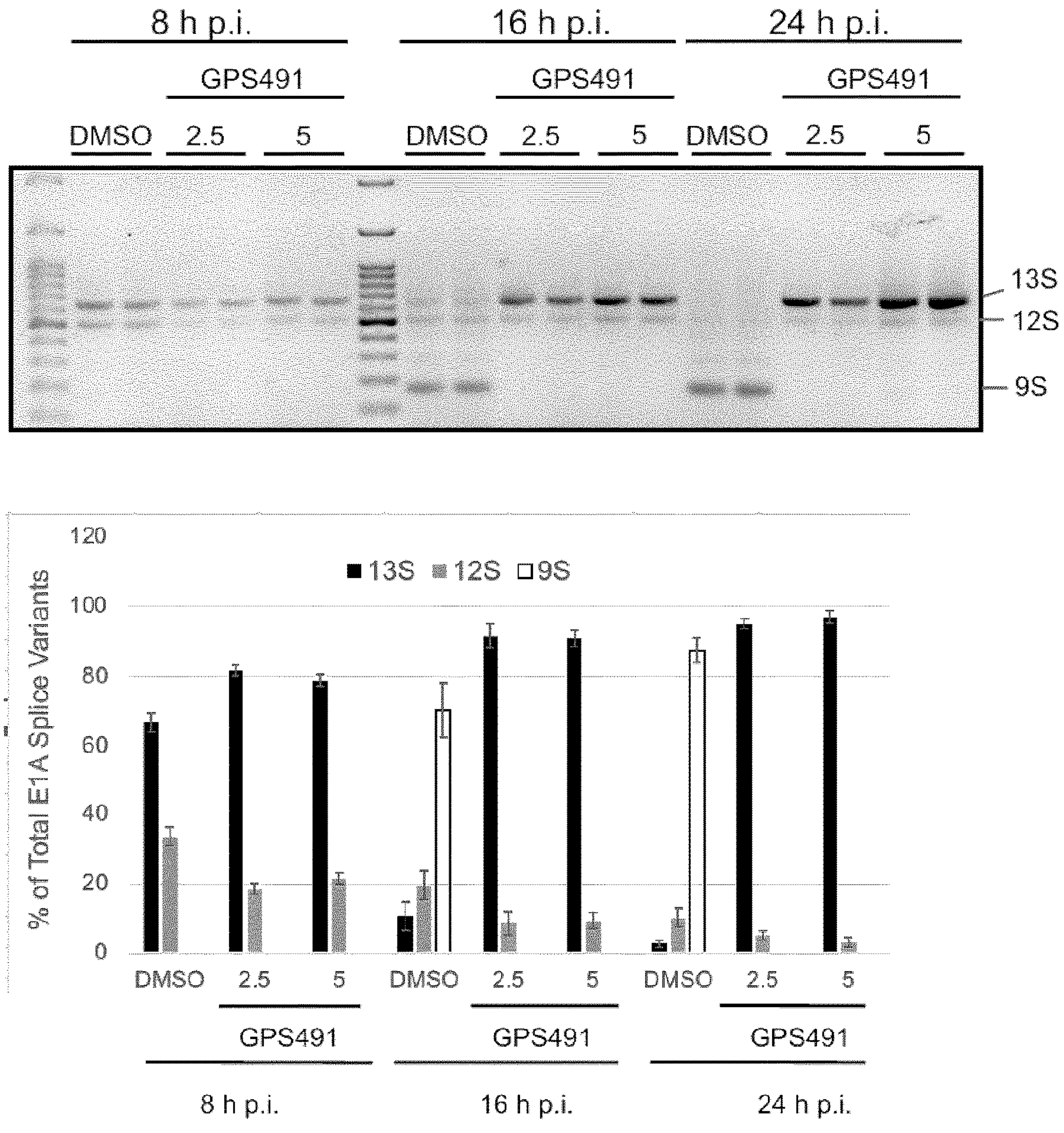
Figure 20C:
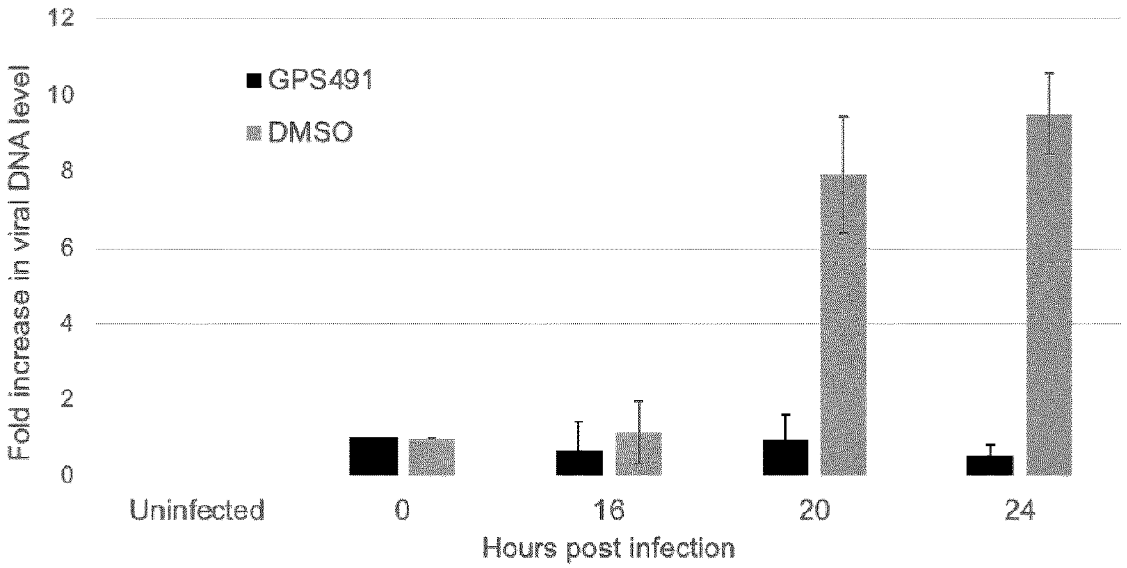

To assess whether the altered pattern of E1A expression could be attributed to changes in viral RNA accumulation or splicing, RT-PCR analysis was performed. The E1A transcript is the first viral RNA generated upon adenovirus infection and can be processed into three different mRNAs by alternative splicing; designated 13S, 12S, and 9S as shown in FIG. 20(A). The abundance of the different E1A RNA isoforms fluctuates over the course of adenovirus infection; 13S and 12S predominating at early times p.i., while 9S is the major E1A RNA at later times. As shown in FIG. 20(B), the treatment of the cells with the GPS491 (12c) compound at both concentrations induced a shift in the E1A transcript splicing which favoured the production of the 13S RNA transcript as compared to the DMSO control which favoured the production of the 9S RNA transcript. Analysis of E1A RNAs over 24 h revealed a marked alteration in E1A RNA accumulation in the presence of GPS491. As early as 8 h p.i., while 13S and 12S RNAs were the predominate isoforms in both DMSO and GPS491 treated samples, GPS491 addition increased the relative abundance of 13S RNA. At later times p.i., while DMSO treated cells shifted E1A RNA accumulation to 9S RNA, GPS491 treatment significantly increased the predominance of 13S RNA, this isoform representing >90% of all E1A RNAs by 16 h p.i. While the changes in E1A RNA processing could explain the altered kinetics of E1A protein expression, the basis for the loss of hexon remained unclear. To determine if the loss of hexon synthesis could be explained by an inhibition of viral DNA synthesis, qPCR was used to measure the abundance of the adenovirus genome in the presence of DMSO or GPS491. As shown in FIG. 20(C), consistent with the loss of late gene expression, GPS491 addition reduced viral DNA accumulation to levels comparable to that observed immediately after virus addition. Together, these observations indicate that GPS491 is affecting early events in adenoviral gene expression essential for virus genome replication.

Figure 21A:
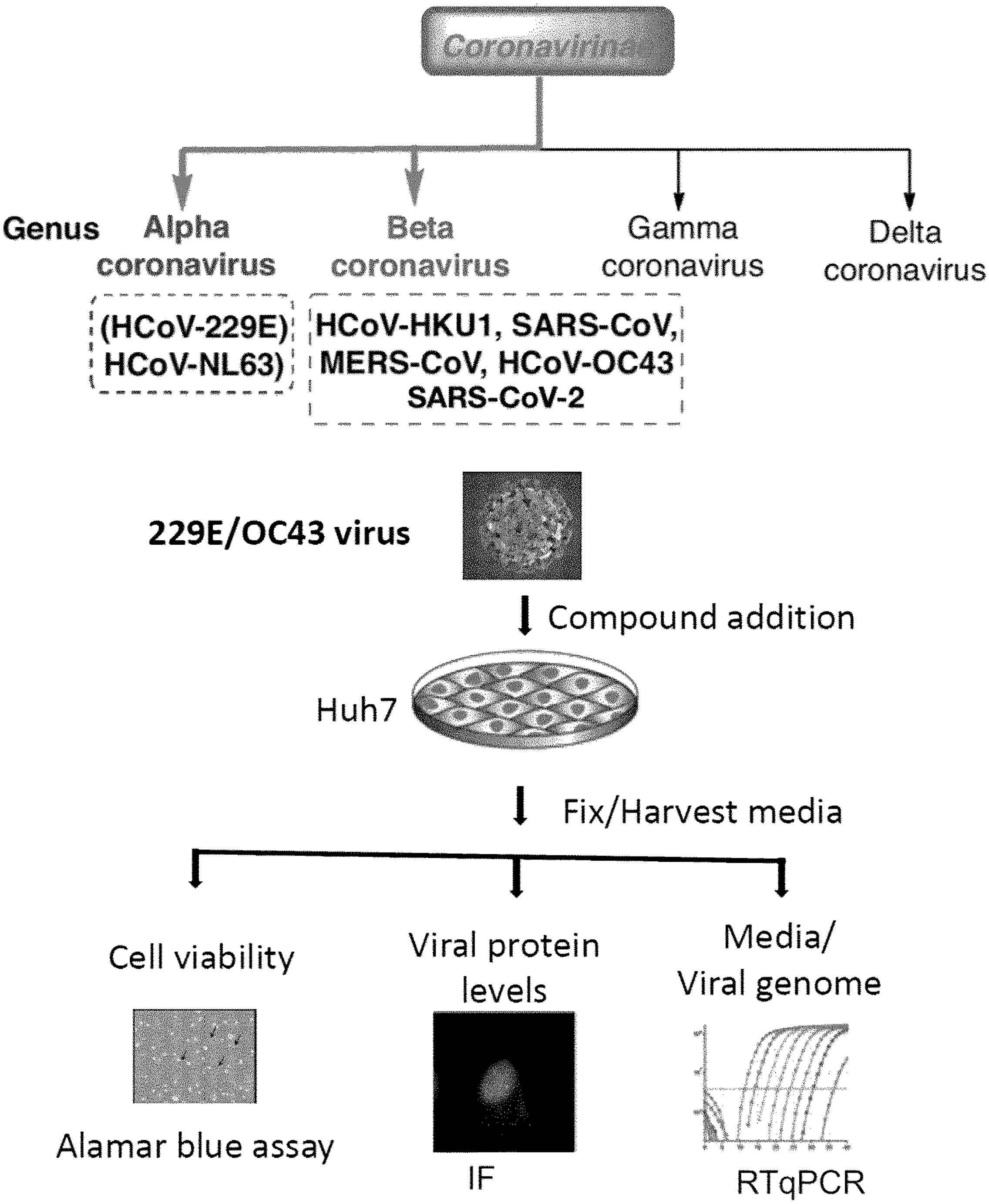
FIG. 21: (A) shows an overview of the members of the subfamily Coronavirinae and the experimental assay design to investigate the effect of the GPS491 (12c) compound on Huh7 cells infected with the 229E coronavirus (Alpha Coronavirus genus) and the OC43 coronavirus (Beta Coronavirus genus); (B) shows the RT-qPCR results showing viral RNA levels (grey bars) for Huh7 cells infected with either 229E coronavirus (grey bars) or the OC43 coronavirus (hatched bars) Also shown is the quantitation of viral proteins in infected cells by immunofluorescence (229E S protein shown as black bars, OC43 N protein shown as white bars); and (C) shows the dose response effect of treatment with GPS491 (12c) compound at increasing concentrations on 229E viral RNA (diamonds, black line) and viral spike protein levels (circles, black line). Cell viability (grey line, circles) of Huh7 cells (right hand y-axis) was determined by Alamar blue. (D) shows the RT-qPCR results of viral RNA levels released into the media from Huh7 cells infected with either 229E coronavirus or the OC43 coronavirus followed by treatment with GPS491 (12c) compound at varying doses, data shown is from 2 independent assays conducted in duplicate; (E) Shows the immunofluorescence results for the expression of the N protein and S protein from SARS-CoV2-infected Huh7 cells treated with either DMSO or increasing concentrations of GPS491 (12c) compound as compared to an uninfected Huh7 cell control, data shown is from one experiment conducted in triplicate; (F) shows the RT-qPCR results of viral RNA levels released into the media from Huh7 cells infected with SARS-CoV2 followed by treatment with GPS491 (12c) compound at increasing doses one experiment conducted in triplicate.
Figure 21B:
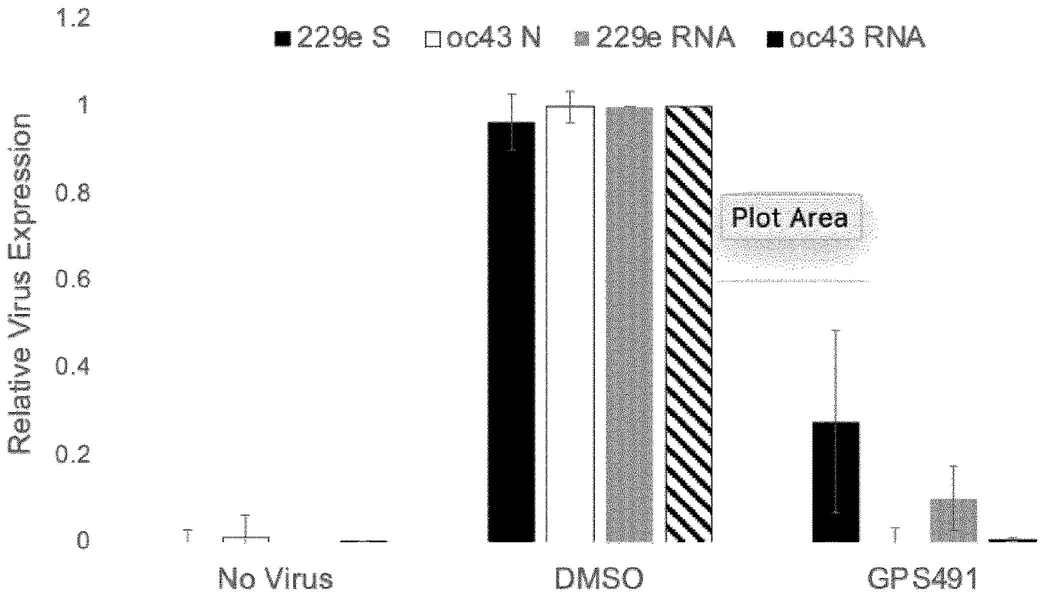
Figure 21C:
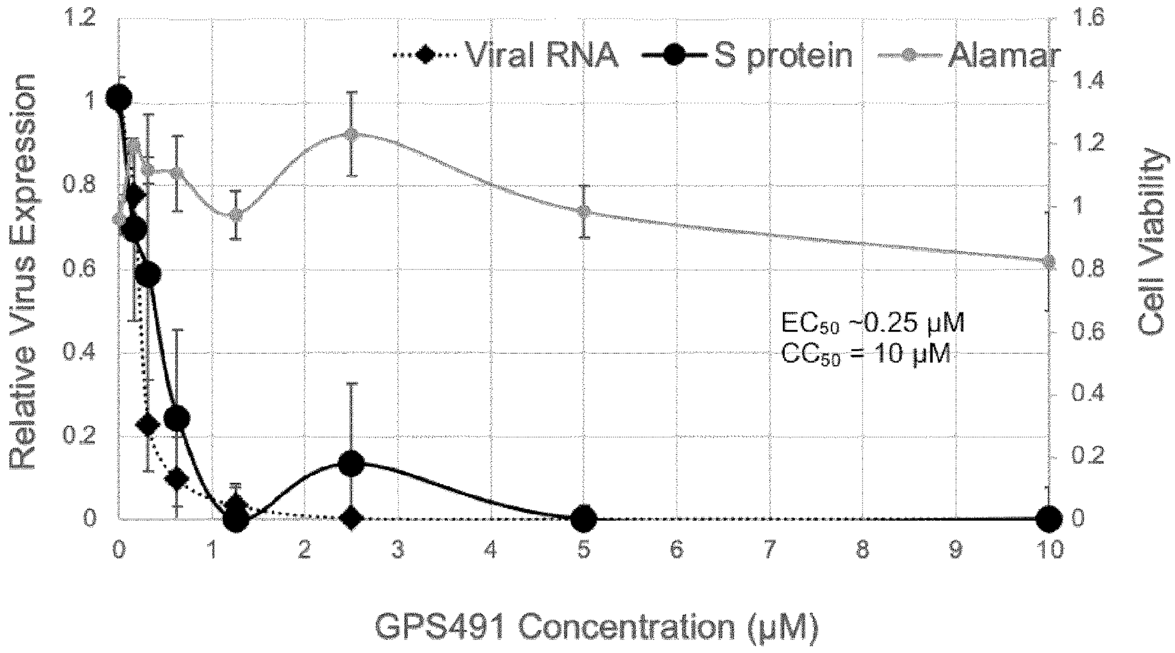
Figure 21D:
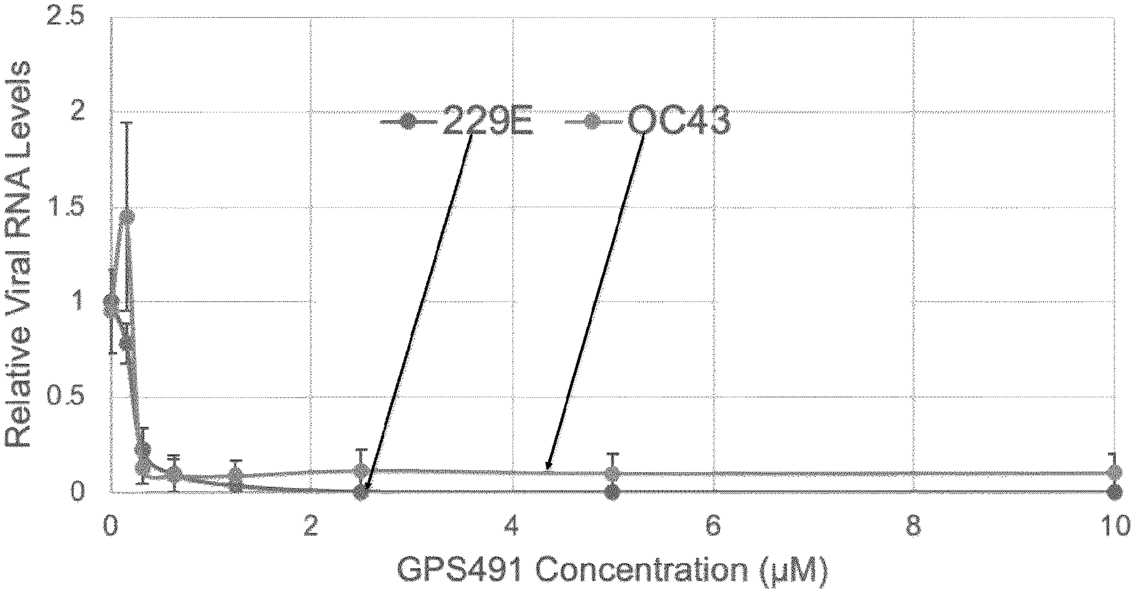
Figure 21E:
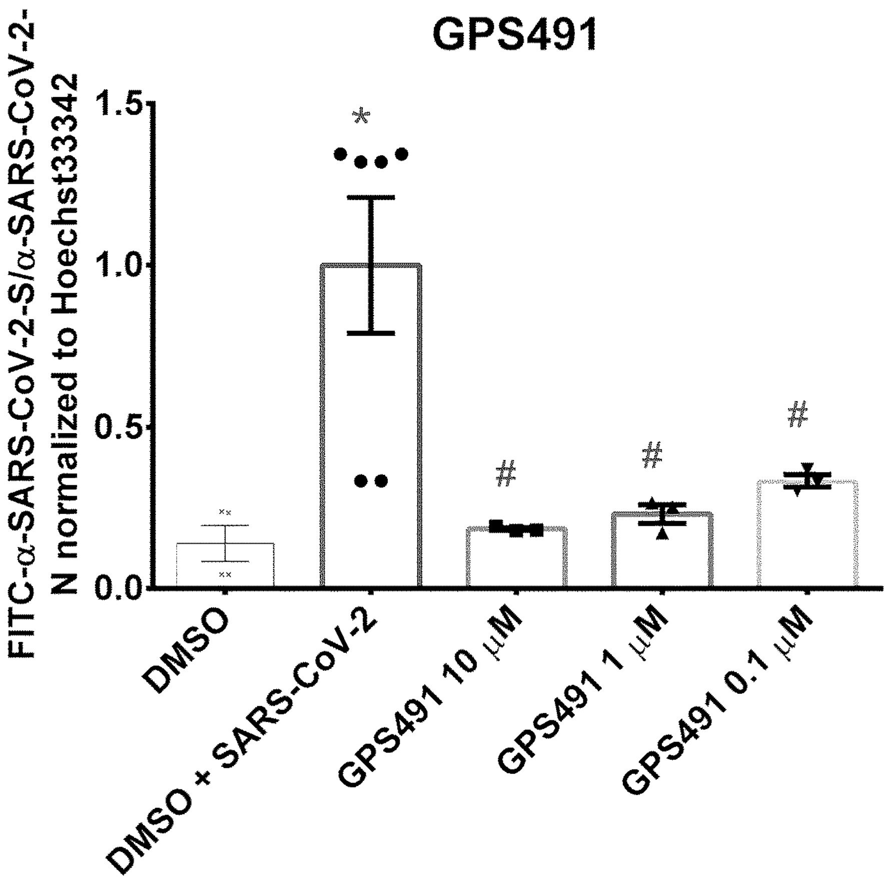
Figure 21F:
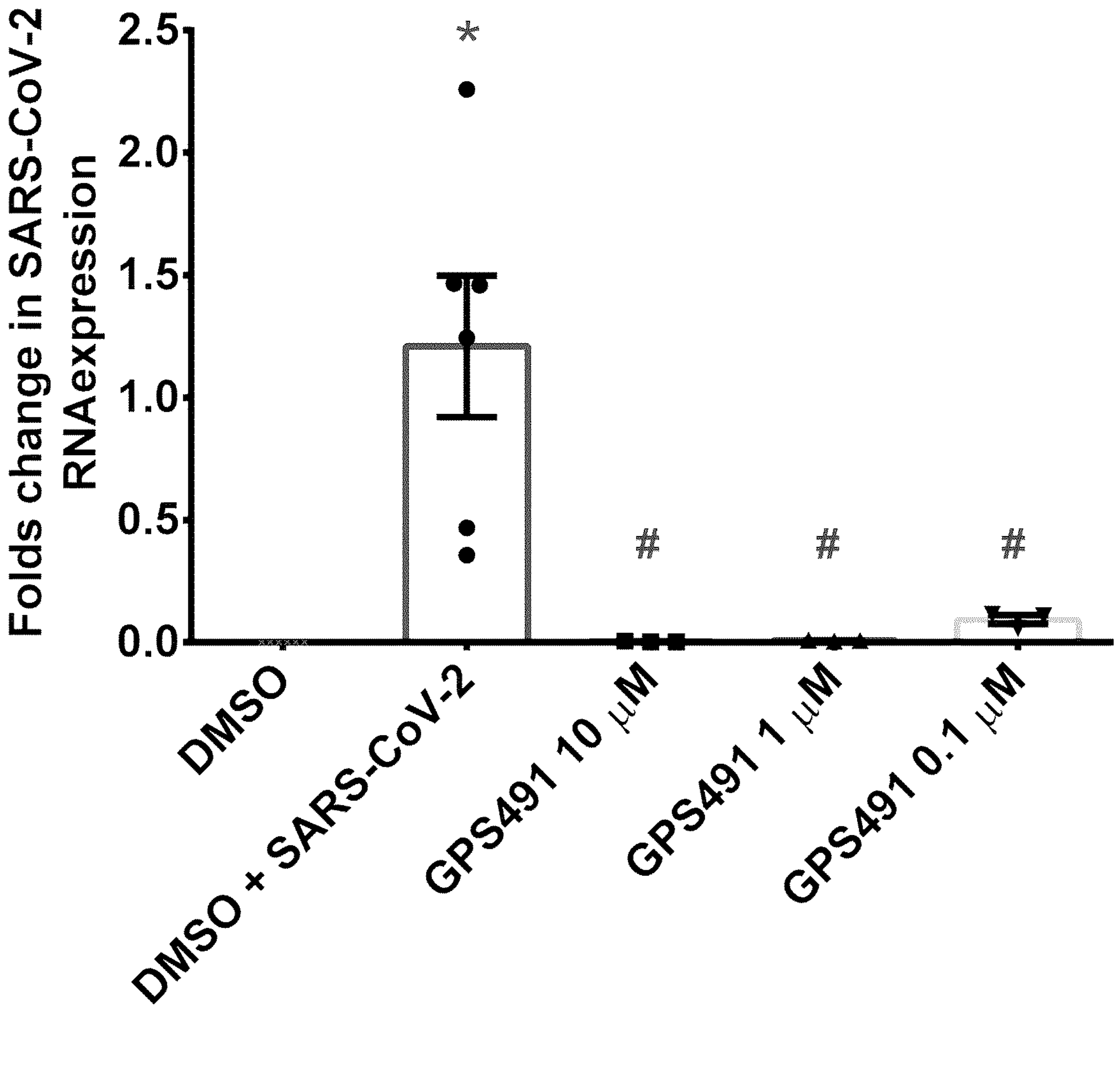

Example 7: Impact of the GPS491 Compound on the Replication of Coronaviruses The ability of GPS491 to inhibit highly unrelated viruses such as HIV-1 and adenovirus raised the question of whether this compound would be active against viruses, which were not directly dependent upon host RNA splicing machinery for their replication such as coronaviruses. As a positive strand RNA viruses whose replication cycle is restricted to the cell cytoplasm, there is no known dependence on cellular splicing. We anticipated that coronaviruses would not be affected by GPS491. However, in contrast to expectations testing of GPS491 for its effect on replication of two human seasonal coronaviruses (229E and OC43) revealed a marked inhibition of both viruses. As shown in FIG. 21A, the GPS491 (12c) compound was tested for its ability to inhibit replication of members of the Alpha and Beta genus of Coronavirus in Huh7 cells. Huh7-infected cells were exposed to increasing concentrations of GPS491 (0 μM to 10 μM) for a 24 h incubation period at which point cells where were fixed to detect viral protein levels by immunofluorescence and the media was collected to determine the viral titres by RT-qPCR. As shown in FIG. 21B, the addition of the GPS491 (12c) compound resulted in a marked reduction in coronavirus replication as evidenced by both a loss of 229E spike (S)/OC43 nucleocapsid (N) protein expression in cells and viral genomic RNA accumulation in the media (indicative of viral particle formation). As shown in FIG. 21C and FIG. 21D, dose response analysis revealed GPS491 to be a highly potent inhibitor of 229E and OC43 virus replication. For the 229E coronavirus, an $EC_{50}$~250 nM for the GPS491 (12c) compound and the 50% cytotoxic concentration ($CC_{50}$) of 10 μM was observed in the Huh7 cell line. The GPS491 compound showed minimal toxicity against the Huh7 cell line over a 24 hr period as shown by the Alamar Blue assay (FIG. 21C). Infection of Huh7 cells with the SARS-CoV2 strain of coronavirus was also investigated. Huh7 cells were infected at an input MOI of 1 with SARS-CoV2 for a 1 hr adsorption period, followed by the replacement of new media supplemented with either DMSO or the GPS491 (12c) compound at varying concentrations (0.1 μM to 10 μM). At two days post infection, cells were fixed and stained to detect the presence of intracellular SARS-CoV2 N and S proteins normalized to Hoechst™ staining (FIG. 21E) and the overlying media was harvested to detect viral RNA levels by RT-qPCR (FIG. 21F). The capacity of GPS491 to suppress replication of several coronaviruses (229E, OC43 and SARS-CoV2) suggests a possible dependence on host cell components affected by GPS491. Alternatively, accumulating evidence has revealed a role for SR kinases in the function of the viral nucleocapsid (N) protein. Sequence analysis has revealed a highly conserved region of arginine-serine repeats within the N protein (similar to those in SR proteins) whose phosphorylation by host kinases (SRPK1, GSK-3) is required for virus replication.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings.

REFERENCES

Berge S. M. et al., J. Pharm. Sci. (1977) "Pharmaceutical Salts" 66(1):1-19). Remington: the Science & Practice of Pharmacy by Alfonso Gennaro, 20th ed., Lippencott Williams & Wilkins, (2000).

McDonald et al., (2008) "Protein lysates were analyzed by 10% Stain-Free gel" Bio-Rad Laboratories, Inc. Bulletin 5782.

Grosso F. et al. (2017) "Suppression of Adenovirus Replication by Cardiotonic Steroids" J Virol. 91(3):e01623-16.

P. Peverallo et al. (2018) "2-CHLORO-N-[2-(1,3-THIAZOL-5-YL)ETHYL]-5-(5-FLUOROPYRIMIDIN-2-YL)-BENZAMIDES AND THEIR USE AS P2X7 RECEPTOR ANTAGONISTS" European Patent 3290417 (based on application number: EP20160186658 20160831).

Brockman, M. A., G. O. Tanzi, et al. (2006). "Use of a novel GFP reporter cell line to examine replication capacity of CXCR4- and CCR5-tropic HIV-1 by flow cytometry." J Virol Methods 131(2): 134-142.

Cheung, P. K., D. Horhant, et al. (2016). "A Parallel Synthesis Approach to the Identification of Novel Diheteroarylamide-Based Compounds Blocking HIV Replication: Potential Inhibitors of HIV-1 Pre-mRNA Alternative Splicing." *J Med Chem* 59(5): 1869-1879.

Duffy, S., Cochrane, A. (2012). Analysis of HIV-1 RNA splicing. *Alternative pre-mRNA splicing*. S. Stamm, Smith, C. W. J., Luhrmann, R., Wiley-VCH Verlag GmbH & Co. KGaA: 438-448.

Wong, R., A. Balachandran, et al. (2011). "Differential effect of CLK SR Kinases on HIV-1 gene expression: potential novel targets for therapy." *Retrovirology* 8(47): 1742-4690.

Wong, R. W., A. Balachandran, et al. (2013). "Characterization of novel inhibitors of HIV-1 replication that function via alteration of viral RNA processing and rev function." *Nucleic acids research* 41(20): 9471-9483.

Zamiri, M. and D. S. Grierson (2017). "A Trimethylsilylamine-Acyl Fluoride Amide Bond Forming Protocol for Weakly Nucleophilic Amines that is Amenable to the Parallel Synthesis of Di(hetero)arylamides." *Synthesis* 49(03): 571-578.

What is claimed is:

1. A compound, the compound having the structure of Formula I:

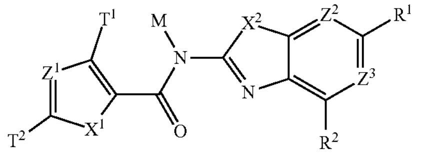

I wherein, $X^1$ is selected from S and O;

$X^2$ is selected from S and O;

$Z^1$ is selected from CH and N;

$Z^2$ is selected from CH, N and $CR^4$;

$Z^3$ is selected from CH, N and $CR^3$;

$T^1$ is selected from H, $CH_2OH$, $CH_2OJ^4$, and $CH_2CH_2OJ^4$;

$T^2$ is selected from $NO_2$, $CF_3$, $OCF_3$, CN, and $CH_2OH$ $CO_2J^5$;

M is H;

$R^1$ is selected from H, $CH_3$, $CH_2OH$, $CH_2CH_2OJ^7$, $CO_2J^7$, $CON(J^7)_2$, $NO_2$, CN, F, Cl, Br, I, $CF_3$, $OCF_3$, $SO_2J^7$, $NJ^7J^7$ and $N_3$;

$R^2$ is selected from H, $CH_3$, $CH_2OH$, $CH_2CH_2OJ^7$, $CO_2J^7$, $CON(J^7)_2$, $NO_2$, CN, F, Cl, Br, I, $CF_3$, $OCF_3$, $SO_2J^7$, $NJ^7J^7$ and $N_3$;

$R^3$ is selected from H, $NO_2$, CN, F, Cl, Br, I, $CF_3$, $N J^7J^7$ and $N_3$;

$R^4$ is selected from H, $NO_2$, CN, F, Cl, Br, I, $CF_3$, $N J^7J^7$ and $N_3$;

$J^4$ is selected from H, and a 1-6 carbon linear, branched or cyclic alkyl;

$J^5$ is 1-6 carbon linear, branched or cyclic alkyl; and $J^7$ is selected from H, and a 1-6 carbon linear, branched or cyclic alkyl.

2. The compound of claim 1, wherein the compound has the structure of Formula II:

II

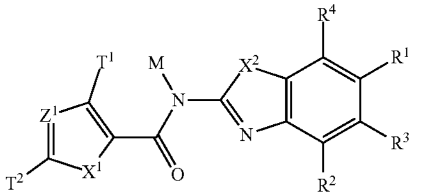

wherein, $X^1$ is selected from S and O;

$X^2$ is selected from S and O;

$Z^1$ is selected from CH and N;

$T^1$ is selected from H, $CH_2OH$, $CH_2OJ^4$, and $CH_2CH_2OJ^4$;

$T^2$ is selected from $NO_2$, $CF_3$, $OCF_3$, CN, and $CH_2OH$ $CO_2J^5$;

M is H;

$R^1$ is selected from H, $CH_2OH$, $CH_2CH_2OJ^7$, $CO_2J^7$, $CON(J^7)_2$, $NO_2$, CN, F, Cl, Br, I, $CF_3$, $OCF_3$, $SO_2J^7$, N $J^7J^7$ and $N_3$;

$R^2$ is selected from H, $CH_2OH$, $CH_2CH_2OJ^7$, $CO_2J^7$, $CON(J^7)_2$, $NO_2$, CN, F, Cl, Br, I, $CF_3$, $OCF_3$, $SO_2J^7$, N $J^7J^7$ and $N_3$;

$R^3$ is selected from H, $NO_2$, CN, F, Cl, Br, I, $CF_3$, N $J^7J^7$ and $N_3$;

$R^4$ is selected from H, $NO_2$, CN, F, Cl, Br, I, $CF_3$, N $J^7J^7$ and $N_3$;

$J^4$ is selected from H, and a 1-6 carbon linear, branched or cyclic alkyl;

$J^5$ is 1-6 carbon linear, branched or cyclic alkyl; and $J^7$ is selected from H, and a 1-6 carbon linear, branched or cyclic alkyl.

3. The compound of claim 1, wherein $X^1$ is S;

$X^2$ is S; and $Z^1$ is N.

4. The compound of claim 1, wherein $T^1$ is selected from H and $CH_2OJ^4$; and $T^2$ is selected from $NO_2$, $CF_3$ and CN.

5. The compound of claim 1, wherein $R^1$ is selected from H, $CO_2J^7$, $NO_2$, CN, F, Cl, Br, $CF_3$, $OCF_3$, $SO_2J^7$ and $N_3$;

$R^2$ is selected from H, $CH_2OH$, $NO_2$, CN, F, Cl, Br, $CF_3$, and $N_3$;

$R^3$ is selected from H, $NO_2$, CN, F, Cl, Br, $CF_3$, and $N_3$; and $R^4$ is selected from H, $NO_2$, CN, F, Cl, Br, $CF_3$, and $N_3$.

6. The compound of claim 1, wherein the compound is selected from one or more of:

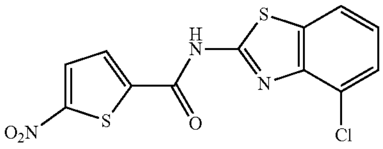

;

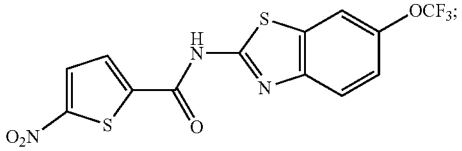

-continued

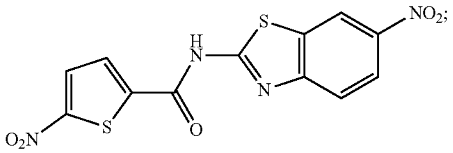

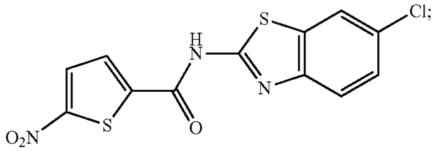

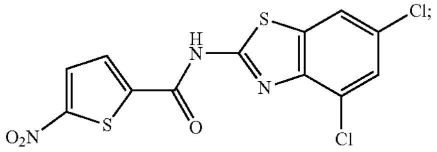

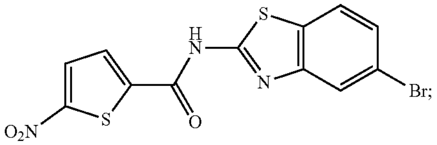

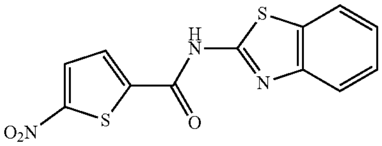

;

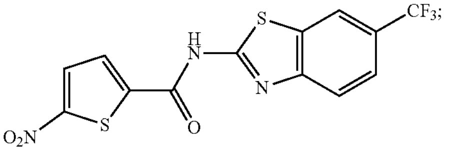

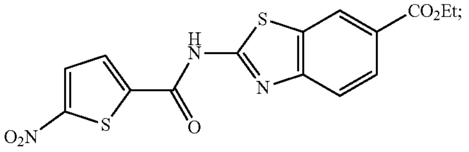

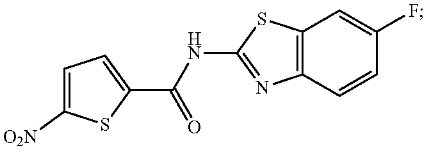

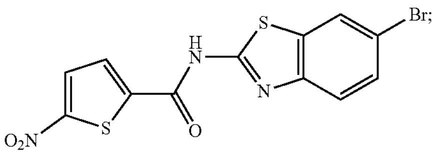

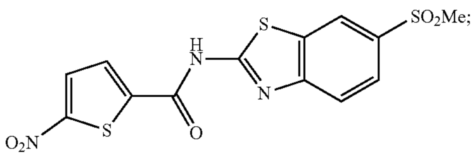

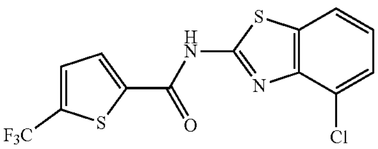

;

-continued
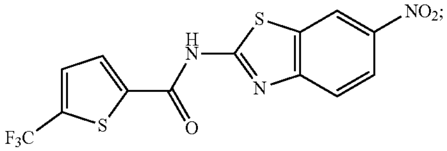
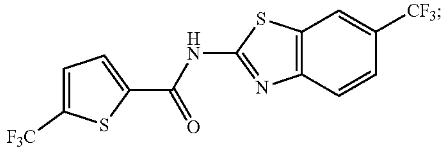
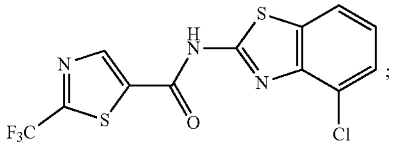
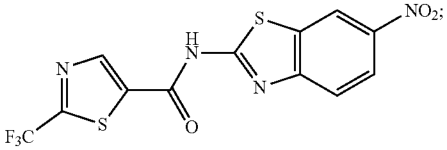
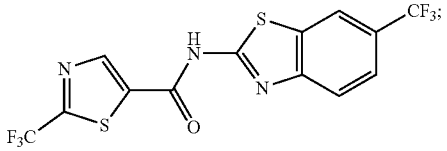
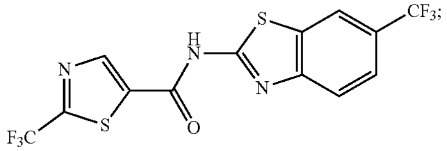
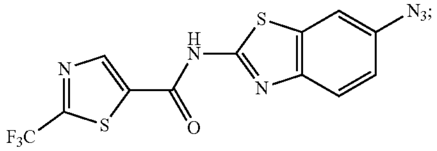
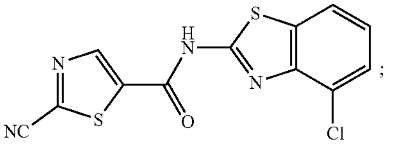
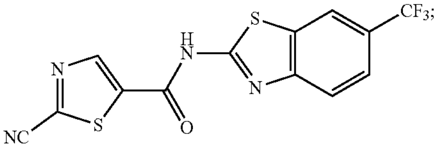
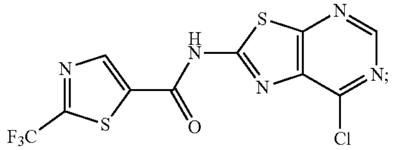
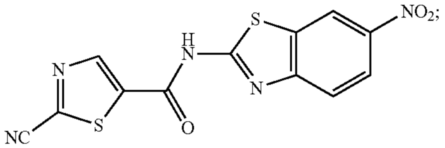
-continued
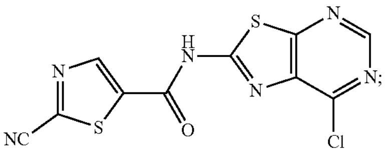
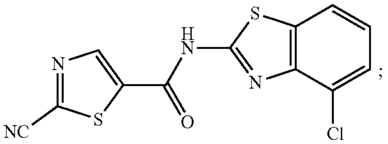
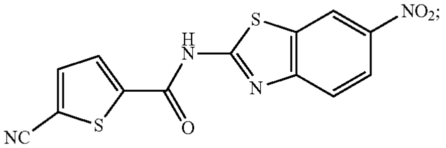
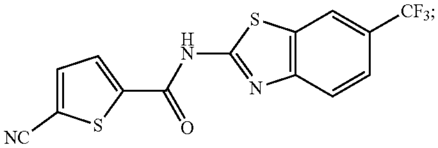
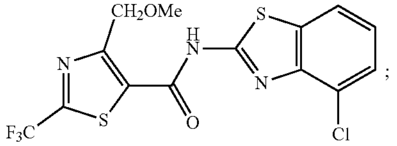
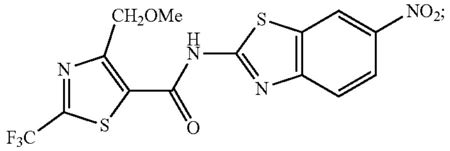
and
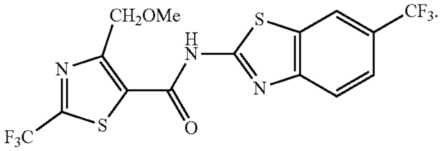
7. The compound claim 1, wherein the compound is selected from one or more of:
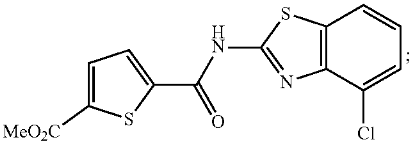
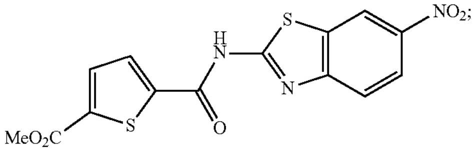
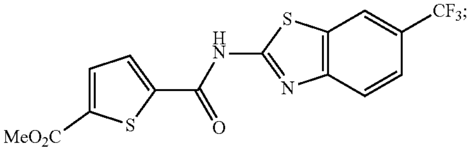
and -continued

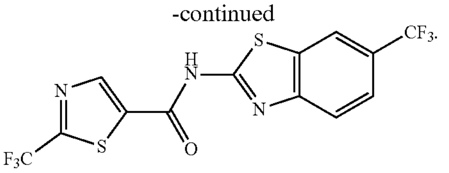

8. The compound of claim 2, wherein $X^1$ is S;

$X^2$ is S; and $Z^1$ is N.

9. The compound of claim 2, wherein $T^1$ is selected from H and $CH_2OJ^4$; and $T^2$ is selected from $NO_2$, $CF_3$, and CN.

10. The compound of claim 2, wherein $R^1$ is selected from H, $CO_2J^7$, $NO_2$, F, Cl, Br, $CF_3$, $OCF_3$, $SO_2J^7$ and $N_3$;

$R^2$ is selected from H, $NO_2$, CN, F, Cl, and Br;

$R^3$ is selected from H, F, Cl, and Br; and $R^4$ is selected from H.

11. The compound of claim 2, wherein the compound is selected from one or more of:

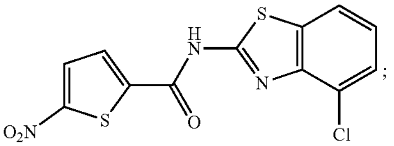

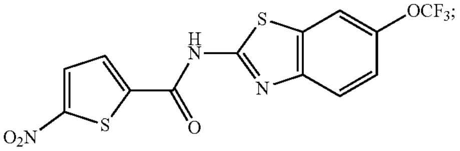

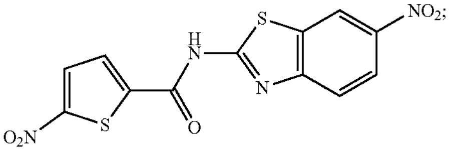

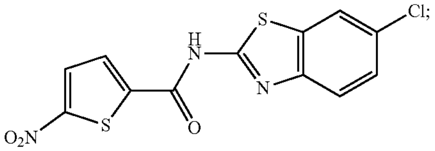

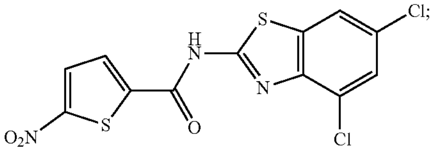

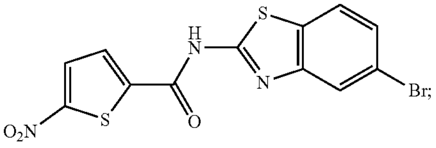

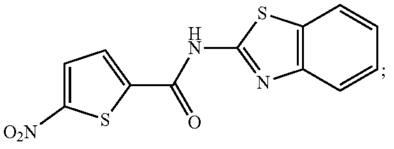

-continued

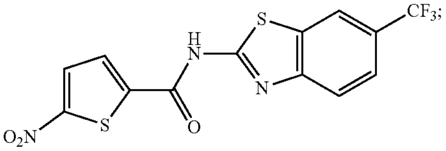

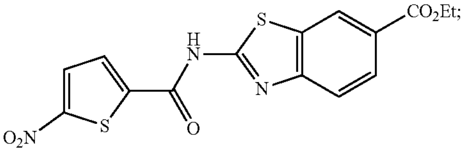

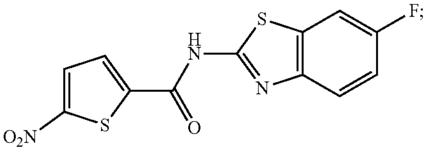

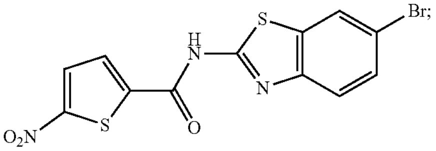

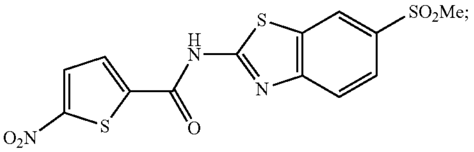

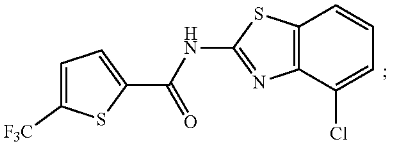

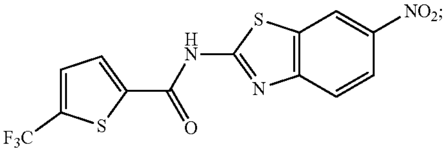

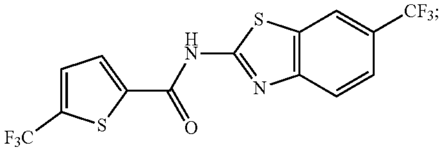

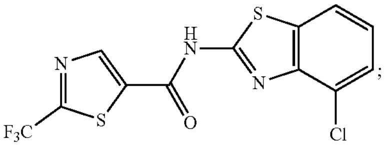

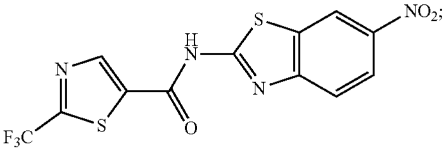

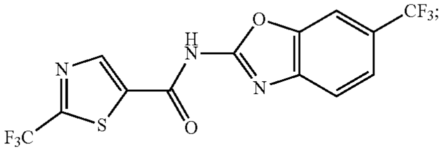

-continued
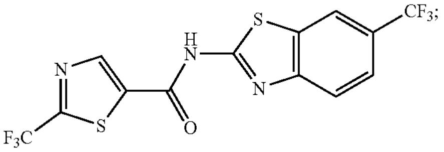
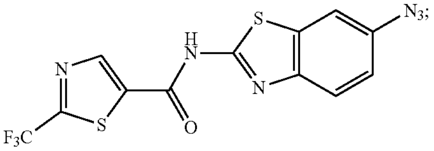
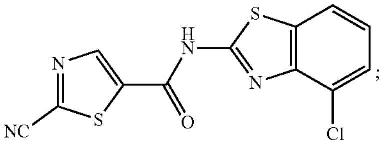
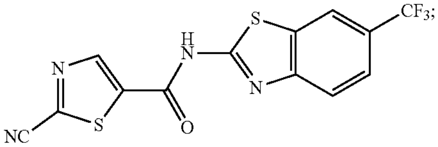
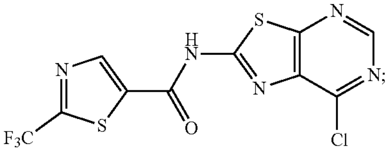
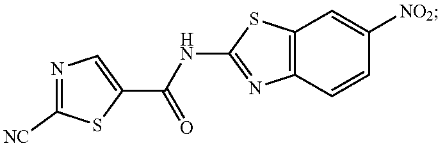
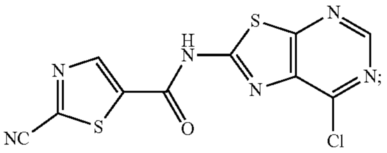
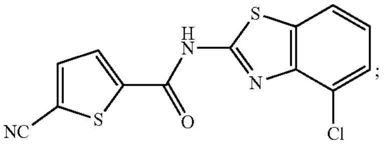
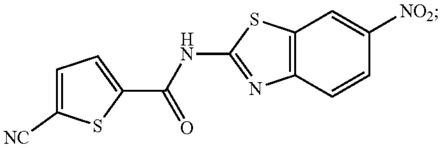
-continued
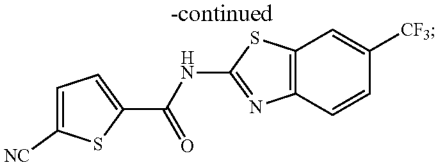
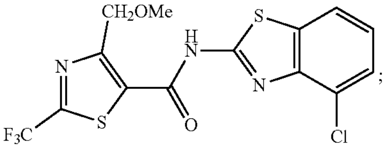
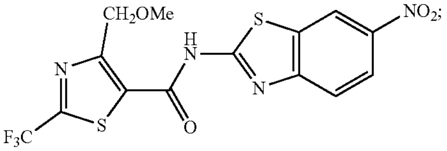
and
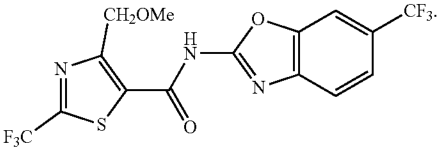
12. The compound of claim 2, wherein the compound is selected from one or more of:
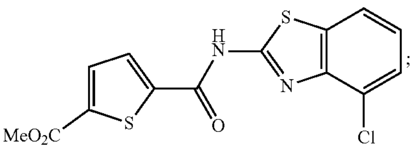
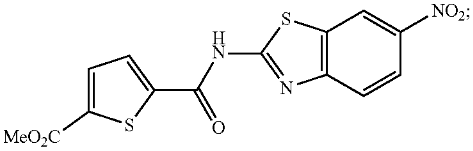
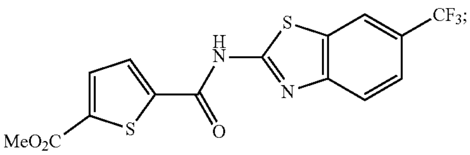
and
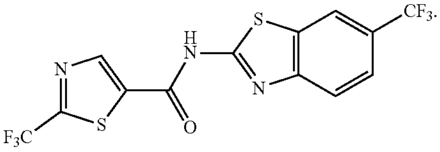
* * * * *